United States Patent
Potter et al.

(10) Patent No.: US 7,258,992 B2
(45) Date of Patent: Aug. 21, 2007

(54) **IMMUNIZATION OF DAIRY CATTLE WITH CHIMERIC GAPC PROTEIN AGAINST *STREPTOCOCCUS* INFECTION**

(75) Inventors: Andrew A. Potter, Saskatoon (CA); Jose Perez-Casal, Saskatoon (CA); Michael Fontaine, Saskatoon (CA)

(73) Assignee: University of Saskatchewan, Saskatoon, Saskatchewan (CA)

( * ) Notice: Subject to any disclaimer, the term of this patent is extended or adjusted under 35 U.S.C. 154(b) by 129 days.

(21) Appl. No.: 11/066,594

(22) Filed: Feb. 25, 2005

(65) Prior Publication Data

US 2005/0142615 A1  Jun. 30, 2005

Related U.S. Application Data

(63) Continuation of application No. 10/650,369, filed on Aug. 27, 2003, now Pat. No. 6,875,853, which is a continuation of application No. 09/878,766, filed on Jun. 11, 2001, now Pat. No. 6,660,270.

(60) Provisional application No. 60/211,247, filed on Jun. 12, 2000.

(51) Int. Cl.
| G01N 33/53 | (2006.01) |
| G01N 33/569 | (2006.01) |
| A61K 39/00 | (2006.01) |
| A61K 39/09 | (2006.01) |
| C07K 14/06 | (2006.01) |
| C07K 14/315 | (2006.01) |

(52) U.S. Cl. ............... 435/7.34; 435/7.1; 435/7.2; 424/184.1; 424/192.1; 424/244.1; 530/300; 530/350

(58) Field of Classification Search ............ None
See application file for complete search history.

(56) References Cited

U.S. PATENT DOCUMENTS

| 4,954,618 A | 9/1990 | Fahnestock |
| 4,977,082 A | 12/1990 | Boyle et al. |
| 5,108,894 A | 4/1992 | Bjorck et al. |
| 5,198,215 A | 3/1993 | De Cueninck |
| 5,237,050 A | 8/1993 | Boyle et al. |
| 5,328,996 A | 7/1994 | Boyle et al. |
| 5,721,339 A | 2/1998 | Boyle et al. |
| 5,753,463 A | 5/1998 | Briles et al. |
| 5,863,543 A | 1/1999 | Jiang et al. |
| 6,063,386 A | 5/2000 | Dale et al. |
| 6,391,316 B1 | 5/2002 | Potter et al. |
| 2001/0014335 A1 | 8/2001 | Saitoh et al. |

FOREIGN PATENT DOCUMENTS

| EP | 0 887 410 | 12/1998 |
| WO | WO93/14198 | 7/1993 |
| WO | WO96/40928 | 12/1996 |
| WO | WO96/41879 | 12/1996 |
| WO | WO98/18930 | 5/1998 |
| WO | WO99/42588 | 8/1999 |
| WO | WO 00/39299 | 7/2000 |

OTHER PUBLICATIONS

Chien et al., "Use of a novel hepatitis C virus (HCV) major-epitope chimeric polypeptide for diagnosis of HCV infection," Journal of Clinical Microbiology, vol. 37 No. 5, apges 1393-1397 (May 1999).*

Baird et al., "Epitopes of Group A Streptococcal M Protein Shared With Antigens of Articular Cartilage and Synovium," *The Journal of Immunology* 146(9):3132-3137 (1991).

Bisno, Alan. L., "Group A Streptococcal Infections and Acute Rheumatic Fever," *New Eng J. Med.* 325:783-793 (1991).

Bowie et al., "Deciphering the message in protein sequences: tolerances to amino acid substitutions," *Science* 247:1306-1310, 1990.

Bronze et al., "Epitopes of Streptococcal M Proteins that Evoke Antibodies That Cross-React with Human Brain," *The Journal of Immunology* 151(5):2820-2828 (1993).

Cunningham et al., "Study of Heart-Reactive Antibody in Antisera and Hybridoma Culture Fluids Against Group A *Strepatococci*," *Infection and Immunity* 42(2):531-538 (1983).

Dale, J. L., "Multivalent Group A Streptooccal Vaccine Designed to Optimize the Immunogenicity of Six Tandem M Protein Fragments," *Vaccine* 17(2):193-200 (1999).

Dale, J. L. and Beachy, G. H., "Multiple, Heart-Cross Reactive Epitopes of Streptococcal M Proteins," *J. Exp. Med.* 161:113-122 (1995).

Dale, J. L. and Beach, G. H., "Protective Antigenic Determinant of Streptococcal M Protein Shared With Sarcolemmal Membrane Protein of Human Heart," *J. Exp. Med.* 156:1165-1176 (1985).

Finch et al., "Further Studies on the Efficacy of a Live Vaccine Against Mastitis Caused by *Streptococcus uberis*," *Vaccine* 15(10):1138-1143 (1997).

Froude et al., "Cross-Reactivity Between *Streptococcus* and Human Tissue: A Model of Molecular Mimicry and Autoimmunity," *Microbiology and Immunology* 145:5-26 (1989).

(Continued)

*Primary Examiner*—Bruce R. Campell
*Assistant Examiner*—Zachariah Lucas
(74) *Attorney, Agent, or Firm*—Robins & Pasternak LLP

(57) ABSTRACT

The recombinant production of Gap4, a chimeric GapC plasmin binding protein comprising the entire amino acid sequence of the *Streptococcus dysgalactiae* GapC protein in addition to unique amino acid sequences from the *Streptococcus parauberis* and *Streptococcus agalactiae* GapC proteins, is described. Also described is the use of Gap4 chimeric GapC protein in vaccine compositions to prevent or treat streptococcal infections in general and mastitis in particular.

12 Claims, 38 Drawing Sheets

OTHER PUBLICATIONS

Gase et al., "Cloning Sequencing and Functional Overexpression of the *Streptococcus* Equismilis H46A gapC Gene Encoding a Glyceraldehyde-3-Phosphate Dehydrogenase that also Functions as a Plasmin(ogen)-Binding Protein. Purification and Biochemical Characterization of the Protein," *European Journal of Biochemistry* 239(1):42-51 (1996).

Hafid et al., "Glyceraldehyde-3-phosphate dehydrogenase from tetrahymena pyriformis: enzyme purification and characterization of a gapC gene with primitive eukayrotic features," *Comparative Biochemistry and Physiology B* 119:493-503, 1998.

Kehoe, Michael A., "Group A Streptococcal Antigens and Vaccine Potential," *Vaccine* 9797:806 (1991).

Lancefield, Rebecca C., "Current Knowledge of Type-Specific M Antigens of Group A *Streptococci*," *J. of Immunology* 89:307-313 (1962).

Langone, John J., "Protein A of *Staphylococcus aureus* and Related Immunoglobulin Receptors Produced by *Streptococci* and *Pneumonococci*," *Advances in Immunology* 32:167 (1982).

Liljeqvist et al., "Surface Display of Functional Fibronectin-Binding Domains on *Staphylococcus camosus*," *FEBS Letters* 446:299-304 (1999).

Stolleman, G. H., "Rheumatogenic *Streptococci* and Autoimmunity," *Clin. Immunol. Immunopathology*, 61:131-142 (1991).

* cited by examiner

```
atg gta gtt aaa gtt ggt att aac ggt ttc ggt cgt atc gga cgt ctt    48
Met Val Val Lys Val Gly Ile Asn Gly Phe Gly Arg Ile Gly Arg Leu
 1           5                      10                      15 gca ttc cgt cgt att caa aat gtt gaa ggt gtt gaa gta act cgt atc    96
Ala Phe Arg Arg Ile Gln Asn Val Glu Gly Val Glu Val Thr Arg Ile
             20                  25                  30 aac gac ctt aca gat cca aac atg ctt gca cac ttg ttg aaa tac gat   144
Asn Asp Leu Thr Asp Pro Asn Met Leu Ala His Leu Leu Lys Tyr Asp
         35                  40                  45 aca act caa gga cgt ttt gac gga act gtt gaa gtt aaa gaa ggt gga   192
Thr Thr Gln Gly Arg Phe Asp Gly Thr Val Glu Val Lys Glu Gly Gly
     50                  55                  60 ttt gaa gta aac gga aac ttc atc aaa gtt tct gct gaa cgt gat cca   240
Phe Glu Val Asn Gly Asn Phe Ile Lys Val Ser Ala Glu Arg Asp Pro
 65                  70                  75                  80 gaa aac atc gac tgg gca act gac ggt gtt gaa atc gtt ctg gaa gca   288
Glu Asn Ile Asp Trp Ala Thr Asp Gly Val Glu Ile Val Leu Glu Ala
                 85                  90                  95 act ggt ttc ttt gct aaa aaa gaa gct gct gaa aaa cac tta cat gct   336
Thr Gly Phe Phe Ala Lys Lys Glu Ala Ala Glu Lys His Leu His Ala
            100                 105                 110 aac ggt gct aaa aaa gtt gtt atc aca gct cct ggt gga aac gac gtt   384
Asn Gly Ala Lys Lys Val Val Ile Thr Ala Pro Gly Gly Asn Asp Val
        115                 120                 125 aaa aca gtt gtt ttc aac act aac cac gac att ctt gac ggt act gaa   432
Lys Thr Val Val Phe Asn Thr Asn His Asp Ile Leu Asp Gly Thr Glu
    130                 135                 140 aca gtt atc tca ggt gct tca tgt act aca aac tgt tta gct cct atg   480
Thr Val Ile Ser Gly Ala Ser Cys Thr Thr Asn Cys Leu Ala Pro Met
145                 150                 155                 160 gct aaa gct ctt cac gat gca ttt ggt atc caa aaa ggt ctt atg act   528
Ala Lys Ala Leu His Asp Ala Phe Gly Ile Gln Lys Gly Leu Met Thr
                165                 170                 175 aca atc cac gct tat act ggt gac caa atg atc ctt gac gga cca cac   576
Thr Ile His Ala Tyr Thr Gly Asp Gln Met Ile Leu Asp Gly Pro His
            180                 185                 190 cgt ggt ggt gac ctt cgt cgt gct cgt gct ggt gct gca aac att gtt   624
Arg Gly Gly Asp Leu Arg Arg Ala Arg Ala Gly Ala Ala Asn Ile Val
        195                 200                 205
```

FIG. 1A

```
cct aac tca act ggt gct gct aaa gct atc ggt ctt gtt atc cca gaa    672
Pro Asn Ser Thr Gly Ala Ala Lys Ala Ile Gly Leu Val Ile Pro Glu
    210                 215                 220 ttg aat ggt aaa ctt gat ggt gct gca caa cgt gtt cct gtt cca act    720
Leu Asn Gly Lys Leu Asp Gly Ala Ala Gln Arg Val Pro Val Pro Thr
225                 230                 235                 240 gga tca gta act gag ttg gtt gta act ctt gat aaa aac gtt tct gtt    768
Gly Ser Val Thr Glu Leu Val Val Thr Leu Asp Lys Asn Val Ser Val
                245                 250                 255 gac gaa atc aac gct gct atg aaa gct gct tca aac gac agt ttc ggt    816
Asp Glu Ile Asn Ala Ala Met Lys Ala Ala Ser Asn Asp Ser Phe Gly
            260                 265                 270 tac act gaa gat cca att gtt tct tca gat atc gta ggc gtg tca tac    864
Tyr Thr Glu Asp Pro Ile Val Ser Ser Asp Ile Val Gly Val Ser Tyr
        275                 280                 285 ggt tca ttg ttt gac gca act caa act aaa gtt atg gaa gtt gac gga    912
Gly Ser Leu Phe Asp Ala Thr Gln Thr Lys Val Met Glu Val Asp Gly
    290                 295                 300 tca caa ttg gtt aaa gtt gta tca tgg tat gac aat gaa atg tct tac    960
Ser Gln Leu Val Lys Val Val Ser Trp Tyr Asp Asn Glu Met Ser Tyr
305                 310                 315                 320 act gct caa ctt gtt cgt aca ctt gag tac ttt gca aaa atc gct aaa   1008
Thr Ala Gln Leu Val Arg Thr Leu Glu Tyr Phe Ala Lys Ile Ala Lys
                325                 330                 335 taa                                                                1011
```

FIG. 1B

```
atg gta gtt aaa gtt ggt att aac ggt ttc ggt cgt atc ggt cgt ctt     48
Met Val Val Lys Val Gly Ile Asn Gly Phe Gly Arg Ile Gly Arg Leu
 1               5                  10                  15 gca ttc cgt cgc atc caa aac gta gaa ggt gtt gaa gtt act cgt atc     96
Ala Phe Arg Arg Ile Gln Asn Val Glu Gly Val Glu Val Thr Arg Ile
                 20                  25                  30 aac gac ctt aca gat cca aac atg ctt gca cac ttg ttg aaa tat gac    144
Asn Asp Leu Thr Asp Pro Asn Met Leu Ala His Leu Leu Lys Tyr Asp
             35                  40                  45 aca act caa ggt cgt ttc gac ggt act gtt gaa gtt aaa gaa ggt gga    192
Thr Thr Gln Gly Arg Phe Asp Gly Thr Val Glu Val Lys Glu Gly Gly
         50                  55                  60 ttc gaa gtt aac ggt caa ttt gtt aaa gtt tct gct gaa cgc gaa cca    240
Phe Glu Val Asn Gly Gln Phe Val Lys Val Ser Ala Glu Arg Glu Pro
 65                  70                  75                  80 gca aac att gac tgg gct act gat ggc gta gaa atc gtt ctt gaa gca    288
Ala Asn Ile Asp Trp Ala Thr Asp Gly Val Glu Ile Val Leu Glu Ala
                 85                  90                  95 act ggt ttc ttt gca tca aaa gaa aaa gct gga caa cac atc cat gaa    336
Thr Gly Phe Phe Ala Ser Lys Glu Lys Ala Gly Gln His Ile His Glu
            100                 105                 110 aat ggt gct aaa aaa gtt gtt atc aca gct cct ggt gga aac gac gtt    384
Asn Gly Ala Lys Lys Val Val Ile Thr Ala Pro Gly Gly Asn Asp Val
        115                 120                 125 aaa aca gtt gtt ttc aac act aac cac gat atc ctt gat gga act gaa    432
Lys Thr Val Val Phe Asn Thr Asn His Asp Ile Leu Asp Gly Thr Glu
130                 135                 140 aca gtt atc tca ggt gct tca tgt act aca aac tgt ctt gct cca atg    480
Thr Val Ile Ser Gly Ala Ser Cys Thr Thr Asn Cys Leu Ala Pro Met
145                 150                 155                 160 gct aaa gct tta caa gac aac ttt ggt gtt aaa caa ggt ttg atg act    528
Ala Lys Ala Leu Gln Asp Asn Phe Gly Val Lys Gln Gly Leu Met Thr
                165                 170                 175 act atc cac gca tac act ggt gac caa atg atc ctt gac gga cca cac    576
Thr Ile His Ala Tyr Thr Gly Asp Gln Met Ile Leu Asp Gly Pro His
            180                 185                 190 cgt ggt ggt gac ctt cgt cgt gct cgt gca ggt gct gca aac atc gtt    624
Arg Gly Gly Asp Leu Arg Arg Ala Arg Ala Gly Ala Ala Asn Ile Val
        195                 200                 205
```

FIG. 2A

```
cct aac tca act ggt gct gca aaa gct atc gga ctt gtt atc cca gaa      672
Pro Asn Ser Thr Gly Ala Ala Lys Ala Ile Gly Leu Val Ile Pro Glu
    210             215                 220 ttg aac ggt aaa ctt gat ggt gct gca caa cgt gtt cct gtt cca act      720
Leu Asn Gly Lys Leu Asp Gly Ala Ala Gln Arg Val Pro Val Pro Thr
225             230                 235                 240 gga tca gta act gaa ttg gtt gca act ctt gaa aaa gac gta act gtc      768
Gly Ser Val Thr Glu Leu Val Ala Thr Leu Glu Lys Asp Val Thr Val
                245                 250                 255 gaa gaa gta aat gca gct atg aaa gca gca gct aac gat tca tac ggt      816
Glu Glu Val Asn Ala Ala Met Lys Ala Ala Ala Asn Asp Ser Tyr Gly
            260                 265                 270 tat act gaa gat cca atc gta tca tct gat atc gtt ggt att tca tac      864
Tyr Thr Glu Asp Pro Ile Val Ser Ser Asp Ile Val Gly Ile Ser Tyr
        275                 280                 285 ggt tca ttg ttt gat gct act caa act aaa gtt caa act gtt gac ggt      912
Gly Ser Leu Phe Asp Ala Thr Gln Thr Lys Val Gln Thr Val Asp Gly
    290                 295                 300 aac caa ttg gtt aaa gtt gtt tca tgg tac gat aac gaa atg tca tac      960
Asn Gln Leu Val Lys Val Val Ser Trp Tyr Asp Asn Glu Met Ser Tyr
305                 310                 315                 320 act tca caa ctt gtt cgt aca ctt gag tac ttt gca aaa atc gct aaa     1008
Thr Ser Gln Leu Val Arg Thr Leu Glu Tyr Phe Ala Lys Ile Ala Lys
                325                 330                 335 taa                                                                  1011
```

FIG. 2B

```
atg gta gtt aaa gtt ggt att aac ggt ttc ggt cgt atc gga cgt ctt    48
Met Val Val Lys Val Gly Ile Asn Gly Phe Gly Arg Ile Gly Arg Leu
 1           5                  10                 15 gca ttc cgt cgt att caa aac gtt gaa ggt gtt gaa gta act cgt att    96
Ala Phe Arg Arg Ile Gln Asn Val Glu Gly Val Glu Val Thr Arg Ile
             20                  25                 30 aac gat ctt act gac cca aat atg ctt gca cac ttg ttg aaa tat gat   144
Asn Asp Leu Thr Asp Pro Asn Met Leu Ala His Leu Leu Lys Tyr Asp
         35                  40                  45 aca act caa ggt cgt ttc gac ggt aca gtt gaa gtt aaa gat ggt gga   192
Thr Thr Gln Gly Arg Phe Asp Gly Thr Val Glu Val Lys Asp Gly Gly
     50                  55                  60 ttc gaa gtt aac gga aac ttc atc aaa gtt tct gct gaa aaa gat cca   240
Phe Glu Val Asn Gly Asn Phe Ile Lys Val Ser Ala Glu Lys Asp Pro
 65                  70                  75                  80 gaa aac att gac tgg gca act gac ggt gta gaa atc gtt ctt gaa gca   288
Glu Asn Ile Asp Trp Ala Thr Asp Gly Val Glu Ile Val Leu Glu Ala
                 85                  90                  95 act ggt ttc ttt gct aaa aaa gca gct gct gaa aaa cat tta cat gct   336
Thr Gly Phe Phe Ala Lys Lys Ala Ala Ala Glu Lys His Leu His Ala
             100                 105                 110 aac ggt gct aaa aaa gtt gtt atc aca gct cct ggt gga gat gat gtt   384
Asn Gly Ala Lys Lys Val Val Ile Thr Ala Pro Gly Gly Asp Asp Val
         115                 120                 125 aaa act gtt gta ttt aac aca aac cat gac att ctt gac ggt aca gaa   432
Lys Thr Val Val Phe Asn Thr Asn His Asp Ile Leu Asp Gly Thr Glu
 130                 135                 140 act gta att tca ggt gct tca tgt act act aac tgt tta gct cca atg   480
Thr Val Ile Ser Gly Ala Ser Cys Thr Thr Asn Cys Leu Ala Pro Met
145                 150                 155                 160 gct aaa gct ttg caa gat aac ttt ggt gtt aaa caa ggt ttg atg aca   528
Ala Lys Ala Leu Gln Asp Asn Phe Gly Val Lys Gln Gly Leu Met Thr
                 165                 170                 175 act atc cac gct tac act ggt gac caa atg atc ctt gac gga cca cac   576
Thr Ile His Ala Tyr Thr Gly Asp Gln Met Ile Leu Asp Gly Pro His
             180                 185                 190 cgt ggt ggt gac ctt cgt cgt gct cgt gct ggt gca agc aac att gtt   624
Arg Gly Gly Asp Leu Arg Arg Ala Arg Ala Gly Ala Ser Asn Ile Val
         195                 200                 205
```

FIG. 3A

```
cct aac tca act ggt gct gct aaa gca atc ggt ctt gta atc cca gaa    672
Pro Asn Ser Thr Gly Ala Ala Lys Ala Ile Gly Leu Val Ile Pro Glu
    210                 215                 220 tta aat ggt aaa ctt gac ggt gct gca caa cgt gtt cct gtt cca act    720
Leu Asn Gly Lys Leu Asp Gly Ala Ala Gln Arg Val Pro Val Pro Thr
225                 230                 235                 240 gga tca gta act gaa tta gta gca gtt ctt gaa aaa gaa act tca gtt    768
Gly Ser Val Thr Glu Leu Val Ala Val Leu Glu Lys Glu Thr Ser Val
                    245                 250                 255 gaa gaa atc aac gca gca atg aaa gca gct gca aac gat tca tac gga    816
Glu Glu Ile Asn Ala Ala Met Lys Ala Ala Ala Asn Asp Ser Tyr Gly
                260                 265                 270 tac act gaa gac cca atc gta tct tct gat atc atc ggt atg gct tac    864
Tyr Thr Glu Asp Pro Ile Val Ser Ser Asp Ile Ile Gly Met Ala Tyr
            275                 280                 285 ggt tca ttg ttt gat gct act caa act aaa gta caa act gtt gat gga    912
Gly Ser Leu Phe Asp Ala Thr Gln Thr Lys Val Gln Thr Val Asp Gly
        290                 295                 300 aat caa tta gtt aaa gtt gtt tca tgg tat gac aac gaa atg tct tac    960
Asn Gln Leu Val Lys Val Val Ser Trp Tyr Asp Asn Glu Met Ser Tyr
305                 310                 315                 320 act gca caa ctt gtt cgt act ctt gag tac ttt gca aaa atc gct aaa   1008
Thr Ala Gln Leu Val Arg Thr Leu Glu Tyr Phe Ala Lys Ile Ala Lys
                    325                 330                 335 taa                                                               1011
```

FIG. 3B

```
atg gta gtt aaa gtt ggt att aac ggt ttt ggc cgt atc gga cgt ctt    48
Met Val Val Lys Val Gly Ile Asn Gly Phe Gly Arg Ile Gly Arg Leu
 1           5                  10                  15 gct ttc cgt cgt att caa aat gta gaa ggt gtt gaa gtt act cgc atc    96
Ala Phe Arg Arg Ile Gln Asn Val Glu Gly Val Glu Val Thr Arg Ile
            20                  25                  30 aac gac ctt aca gat cca aat atg ctt gca cac ttg tta aaa tac gat   144
Asn Asp Leu Thr Asp Pro Asn Met Leu Ala His Leu Leu Lys Tyr Asp
        35                  40                  45 aca act caa ggt cgt ttt gac ggt act gta gaa gtt aaa gat ggt gga   192
Thr Thr Gln Gly Arg Phe Asp Gly Thr Val Glu Val Lys Asp Gly Gly
50                  55                  60 ttt gac gtt aac gga aaa ttc att aaa gtt tct gct gaa aaa gat cca   240
Phe Asp Val Asn Gly Lys Phe Ile Lys Val Ser Ala Glu Lys Asp Pro
65                  70                  75                  80 gaa caa att gac tgg gca act gac ggt gtt gaa atc gtt ctt gaa gca   288
Glu Gln Ile Asp Trp Ala Thr Asp Gly Val Glu Ile Val Leu Glu Ala
            85                  90                  95 act ggt ttc ttt gct aaa aaa gca gct gct gaa aaa cat tta cat gaa   336
Thr Gly Phe Phe Ala Lys Lys Ala Ala Ala Glu Lys His Leu His Glu
            100                 105                 110 aat ggt gct aaa aaa gtt gtt atc act gct cct ggt gga gat gac gtg   384
Asn Gly Ala Lys Lys Val Val Ile Thr Ala Pro Gly Gly Asp Asp Val
        115                 120                 125 aaa aca gtt gta ttt aac act aac cat gat atc ctt gat gga act gaa   432
Lys Thr Val Val Phe Asn Thr Asn His Asp Ile Leu Asp Gly Thr Glu
    130                 135                 140 aca gtt att tca ggt gct tca tgt act aca aac tgt tta gct cca atg   480
Thr Val Ile Ser Gly Ala Ser Cys Thr Thr Asn Cys Leu Ala Pro Met
145                 150                 155                 160 gct aaa gct tta caa gat aac ttt ggc gta aaa caa ggt tta atg act   528
Ala Lys Ala Leu Gln Asp Asn Phe Gly Val Lys Gln Gly Leu Met Thr
            165                 170                 175 aca atc cac gct tac act ggt gat caa atg ctt ctt gat gga cct cac   576
Thr Ile His Ala Tyr Thr Gly Asp Gln Met Leu Leu Asp Gly Pro His
            180                 185                 190 cgt ggt ggt gac tta cgt cgt gcc cgt gct ggt gct aac aat att gtt   624
Arg Gly Gly Asp Leu Arg Arg Ala Arg Ala Gly Ala Asn Asn Ile Val
        195                 200                 205
```

FIG. 4A

```
cct aac tca act ggt gct gct aaa gca atc ggt ctt gtt atc cct gaa    672
Pro Asn Ser Thr Gly Ala Ala Lys Ala Ile Gly Leu Val Ile Pro Glu
    210             215                 220 tta aat ggt aaa ctt gac ggt gct gca caa cgt gta cca gtt cca aca    720
Leu Asn Gly Lys Leu Asp Gly Ala Ala Gln Arg Val Pro Val Pro Thr
225             230                 235                 240 ggt tca gta aca gaa tta gta gca gtt ctt aat aaa gaa act tca gta    768
Gly Ser Val Thr Glu Leu Val Ala Val Leu Asn Lys Glu Thr Ser Val
                245                 250                 255 gaa gaa att aac tca gta atg aaa gct gca gct aat gat tca tat ggt    816
Glu Glu Ile Asn Ser Val Met Lys Ala Ala Ala Asn Asp Ser Tyr Gly
            260                 265                 270 tac act gaa gat cca atc gta tca tct gat atc gtt ggt atg tct ttc    864
Tyr Thr Glu Asp Pro Ile Val Ser Ser Asp Ile Val Gly Met Ser Phe
        275                 280                 285 ggt tca tta ttc gat gct act caa act aaa gta caa act gtt gat gga    912
Gly Ser Leu Phe Asp Ala Thr Gln Thr Lys Val Gln Thr Val Asp Gly
    290                 295                 300 aat caa tta gtt aaa gtt gtt tca tgg tat gac aat gaa atg tct tac    960
Asn Gln Leu Val Lys Val Val Ser Trp Tyr Asp Asn Glu Met Ser Tyr
305                 310                 315                 320 act gct caa ctt gat cgt aca ctt gag tac ttt gca aaa atc gct aaa    1008
Thr Ala Gln Leu Asp Arg Thr Leu Glu Tyr Phe Ala Lys Ile Ala Lys
                325                 330                 335 taa                                                                1011
```

FIG. 4B

```
atg gta gtt aaa gtt ggt att aac ggt ttc gga cgt atc ggt cgt ctt    48
Met Val Val Lys Val Gly Ile Asn Gly Phe Gly Arg Ile Gly Arg Leu
 1               5                  10                  15 gca ttc cgt cgt att caa aat gtt gaa ggt gtt gaa gta act cgt atc    96
Ala Phe Arg Arg Ile Gln Asn Val Glu Gly Val Glu Val Thr Arg Ile
                 20                  25                  30 aat gac ctt aca gat cct aac atg ctt gca cac ttg ttg aaa tat gat   144
Asn Asp Leu Thr Asp Pro Asn Met Leu Ala His Leu Leu Lys Tyr Asp
             35                  40                  45 aca act caa ggt cgt ttt gac ggt aca gtt gaa gtt aaa gat ggt gga   192
Thr Thr Gln Gly Arg Phe Asp Gly Thr Val Glu Val Lys Asp Gly Gly
         50                  55                  60 ttc gaa gtt aac gga agc ttt gtt aaa gtt tct gca gaa cgc gaa cca   240
Phe Glu Val Asn Gly Ser Phe Val Lys Val Ser Ala Glu Arg Glu Pro
 65                  70                  75                  80 gca aac att gac tgg gct act gat ggt gta gac atc gtt ctt gaa gca   288
Ala Asn Ile Asp Trp Ala Thr Asp Gly Val Asp Ile Val Leu Glu Ala
                 85                  90                  95 aca ggt ttc ttc gct tct aaa gca gct gct gaa caa cac atc cac gct   336
Thr Gly Phe Phe Ala Ser Lys Ala Ala Ala Glu Gln His Ile His Ala
             100                 105                 110 aac ggt gcg aaa aaa gtt gtt atc aca gct cct ggt gga aat gac gtt   384
Asn Gly Ala Lys Lys Val Val Ile Thr Ala Pro Gly Gly Asn Asp Val
         115                 120                 125 aaa aca gtt gtt tac aac act aac cat gat att ctt gat gga act gaa   432
Lys Thr Val Val Tyr Asn Thr Asn His Asp Ile Leu Asp Gly Thr Glu
 130                 135                 140 aca gtt atc tca ggt gct tca tgt act aca aac tgt tta gct cca atg   480
Thr Val Ile Ser Gly Ala Ser Cys Thr Thr Asn Cys Leu Ala Pro Met
 145                 150                 155                 160 gct aaa gca tta caa gat aac ttt ggt gta aaa caa ggt tta atg act   528
Ala Lys Ala Leu Gln Asp Asn Phe Gly Val Lys Gln Gly Leu Met Thr
                 165                 170                 175 act atc cat ggt tac act ggt gac caa atg gtt ctt gac gga cca cac   576
Thr Ile His Gly Tyr Thr Gly Asp Gln Met Val Leu Asp Gly Pro His
             180                 185                 190 cgt ggt ggt gat ctt cgt cgt gct cgt gca gct gca gca aac atc gtt   624
Arg Gly Gly Asp Leu Arg Arg Ala Arg Ala Ala Ala Ala Asn Ile Val
         195                 200                 205
```

FIG. 5A

```
cct aac tca act ggt gct gct aaa gca atc ggt ctt gtt atc cca gaa    672
Pro Asn Ser Thr Gly Ala Ala Lys Ala Ile Gly Leu Val Ile Pro Glu
    210                 215                 220 tta aat ggt aaa ctt gac ggt gct gca caa cgt gtt cct gtt cca act    720
Leu Asn Gly Lys Leu Asp Gly Ala Ala Gln Arg Val Pro Val Pro Thr
225                 230                 235                 240 gga tca gta act gaa tta gta gca gtt ctt gaa aaa gat act tca gta    768
Gly Ser Val Thr Glu Leu Val Ala Val Leu Glu Lys Asp Thr Ser Val
                245                 250                 255 gaa gaa atc aat gca gct atg aaa gca gca gct aac gat tca tac ggt    816
Glu Glu Ile Asn Ala Ala Met Lys Ala Ala Ala Asn Asp Ser Tyr Gly
            260                 265                 270 tac act gaa gat gct atc gta tca tca gat atc gta ggt att tct tac    864
Tyr Thr Glu Asp Ala Ile Val Ser Ser Asp Ile Val Gly Ile Ser Tyr
        275                 280                 285 ggt tca tta ttt gat gct act caa act aaa gta caa act gtt gat gga    912
Gly Ser Leu Phe Asp Ala Thr Gln Thr Lys Val Gln Thr Val Asp Gly
    290                 295                 300 aat caa ttg gtt aaa gtt gtt tca tgg tat gac aat gaa atg tct tac    960
Asn Gln Leu Val Lys Val Val Ser Trp Tyr Asp Asn Glu Met Ser Tyr
305                 310                 315                 320 act gct caa ctt gtt cgt act ctt gag tac ttt gca aaa atc gct aaa   1008
Thr Ala Gln Leu Val Arg Thr Leu Glu Tyr Phe Ala Lys Ile Ala Lys
                325                 330                 335 taa                                                                1011
```

FIG. 5B

```
atg aaa aaa ata aca ggg att att tta ttg ctt ctt gca gtc att att    48
Met Lys Lys Ile Thr Gly Ile Ile Leu Leu Leu Leu Ala Val Ile Ile
 1               5                  10                  15 ctg tct gca tgc cag gca aac tac gga tcc ggt atg gta gtt aaa gtt    96
Leu Ser Ala Cys Gln Ala Asn Tyr Gly Ser Gly Met Val Val Lys Val
            20                  25                  30 ggt att aac ggt ttc ggt cgt atc gga cgt ctt gca ttc cgt cgt att   144
Gly Ile Asn Gly Phe Gly Arg Ile Gly Arg Leu Ala Phe Arg Arg Ile
                35                  40                  45 caa aat gtt gaa ggt gtt gaa gta act cgt atc aac gac ctt aca gat   192
Gln Asn Val Glu Gly Val Glu Val Thr Arg Ile Asn Asp Leu Thr Asp
        50                  55                  60 cca aac atg ctt gca cac ttg ttg aaa tac gat aca act caa gga cgt   240
Pro Asn Met Leu Ala His Leu Leu Lys Tyr Asp Thr Thr Gln Gly Arg
65                  70                  75                  80 ttt gac gga act gtt gaa gtt aaa gaa ggt gga ttt gaa gta aac gga   288
Phe Asp Gly Thr Val Glu Val Lys Glu Gly Gly Phe Glu Val Asn Gly
                85                  90                  95 aac ttc atc aaa gtt tct gct gaa cgt gat cca gaa aac atc gac tgg   336
Asn Phe Ile Lys Val Ser Ala Glu Arg Asp Pro Glu Asn Ile Asp Trp
                100                 105                 110 gca act gac ggt gtt gaa atc gtt ctg gaa gca ctc gag ggt act gta   384
Ala Thr Asp Gly Val Glu Ile Val Leu Glu Ala Leu Glu Gly Thr Val
            115                 120                 125 gaa gtt aaa gat ggt gga ttt gac gtt aac gga aaa ttc att aaa gtt   432
Glu Val Lys Asp Gly Gly Phe Asp Val Asn Gly Lys Phe Ile Lys Val
        130                 135                 140 tct gct gaa aaa gat cca gaa caa att gac tgg gca act gac ggt gtt   480
Ser Ala Glu Lys Asp Pro Glu Gln Ile Asp Trp Ala Thr Asp Gly Val
145                 150                 155                 160 gaa atc gtt ctt gaa atc gat ggt act gtt gaa gtt aaa gaa ggt gga   528
Glu Ile Val Leu Glu Ile Asp Gly Thr Val Glu Val Lys Glu Gly Gly
                165                 170                 175 ttc gaa gtt aac ggt caa ttt gtt aaa gtt tct gct gaa cgc gaa cca   576
Phe Glu Val Asn Gly Gln Phe Val Lys Val Ser Ala Glu Arg Glu Pro
                180                 185                 190 gca aac att gac tgg gct act gat ggc gta gaa atc gtt ctt gaa gca   624
Ala Asn Ile Asp Trp Ala Thr Asp Gly Val Glu Ile Val Leu Glu Ala
            195                 200                 205
```

FIG. 6A

```
act agt ttc ttt gct aaa aaa gaa gct gct gaa aaa cac tta cat gct    672
Thr Ser Phe Phe Ala Lys Lys Glu Ala Ala Glu Lys His Leu His Ala
    210             215             220 aac ggt gct aaa aaa gtt gtt atc aca gct cct ggt gga aac gac gtt    720
Asn Gly Ala Lys Lys Val Val Ile Thr Ala Pro Gly Gly Asn Asp Val
225             230             235             240 aaa aca gtt gtt ttc aac act aac cac gac att ctt gac ggt act gaa    768
Lys Thr Val Val Phe Asn Thr Asn His Asp Ile Leu Asp Gly Thr Glu
            245             250             255 aca gtt atc tca ggt gct tca tgt act aca aac tgt tta gct cct atg    816
Thr Val Ile Ser Gly Ala Ser Cys Thr Thr Asn Cys Leu Ala Pro Met
        260             265             270 gct aaa gct ctt cac gat gca ttt ggt atc caa aaa ggt ctt atg act    864
Ala Lys Ala Leu His Asp Ala Phe Gly Ile Gln Lys Gly Leu Met Thr
    275             280             285 aca atc cac gct tat act ggt gac caa atg atc ctt gac gga cca cac    912
Thr Ile His Ala Tyr Thr Gly Asp Gln Met Ile Leu Asp Gly Pro His
290             295             300 cgt ggt ggt gac ctt cgt cgt gct cgt gct ggt gct gca aac att gtt    960
Arg Gly Gly Asp Leu Arg Arg Ala Arg Ala Gly Ala Ala Asn Ile Val
305             310             315             320 cct aac tca act ggt gct gct aaa gct atc ggt ctt gtt atc cca gaa   1008
Pro Asn Ser Thr Gly Ala Ala Lys Ala Ile Gly Leu Val Ile Pro Glu
            325             330             335 ttg aat ggt aaa ctt gat ggt gct gca caa cgt gtt cct gtt cca act   1056
Leu Asn Gly Lys Leu Asp Gly Ala Ala Gln Arg Val Pro Val Pro Thr
        340             345             350 gga tca gta act gag ttg gtt gta act ctt gat aaa aac gtt tct gtt   1104
Gly Ser Val Thr Glu Leu Val Val Thr Leu Asp Lys Asn Val Ser Val
    355             360             365 gac gaa atc aac gct gct atg aaa gct gct tca aac gac agt ttc ggt   1152
Asp Glu Ile Asn Ala Ala Met Lys Ala Ala Ser Asn Asp Ser Phe Gly
370             375             380 tac act gaa gat cca att gtt tct tca gat atc gta ggc gtg tca tac   1200
Tyr Thr Glu Asp Pro Ile Val Ser Ser Asp Ile Val Gly Val Ser Tyr
385             390             395             400 ggt tca ttg ttt gac gca act caa act aaa gtt atg gaa gtt gac gga   1248
Gly Ser Leu Phe Asp Ala Thr Gln Thr Lys Val Met Glu Val Asp Gly
            405             410             415
```

FIG. 6B

```
tca caa ttg gtt aaa gtt gta tca tgg tat gac aat gaa atg tct tac    1296
Ser Gln Leu Val Lys Val Val Ser Trp Tyr Asp Asn Glu Met Ser Tyr
            420                 425                 430 act gct caa ctt gtt cgt aca ctt gag tat ttt gca aaa atc gct aaa    1344
Thr Ala Gln Leu Val Arg Thr Leu Glu Tyr Phe Ala Lys Ile Ala Lys
            435                 440                 445 taa                                                                1347
```

FIG. 6C

```
               1                                                    50
    DysGapC  ATGGTAGTTA AAGTTGGTAT TAACGGTTTC GGTCGTATCG GACGTCTTGC
    SpyGapC  ---------- ---------- ---------- ---------- ----------
    SeqGapC  ---------- ---------- ---------- ---------- ----------
 ParaUbGapC  ---------- ---------- ---------t --c------- ----------
    UberGapc  ---------- ---------- ---------- ---------- ----------
 AgalGapCDNA  ---------- ---------- ---------- ---------- -t--------
    SiniGapC  ---------- ---------- ---------- --a------- -t--------
    BovGapC  ---------- ---------- ---------- -----c---- -g--c--g-t 51                                                   100
    DysGapC  ATTCCGTCGT ATTCAAAATG TTGAAGGTGT TGAAGTAACT CGTATCAACG
    SpyGapC  ------c--- --------ca -c-------- ---------- --------t-
    SeqGapC  ---------- ---------- ---------- ---------- ----------
 ParaUbGapC  t--------- ---------- -a-------- ------t--- --c-------
    UberGapc  ---------- --------c- ---------- ---------- -----t----
 AgalGapCDNA  ---------c --c-----c- -a-------- ------t--- ----------
    SiniGapC  ---------- ---------- ---------- ---------- --------t-
    BovGapC  cac-a-ggc- gc-ttt---t c--gcaaa-- g--ca-cgtc gcc-----t-

101                                                  150
    DysGapC  ACC...TTAC AGATCCAAAC ATGCTTGCAC ACTTGTTGAA ATACGATACA
    SpyGapC  ---...---- --------t- ---------- ---------- ---c------
    SeqGapC  ---...---- ---------- ---------- ---------- ---c------
 ParaUbGapC  ---...---- --------t- ---------- -------a-- ---c------
    UberGapc  -t-...---- t--c-----t ---------- ---------- ---t------
 AgalGapCDNA  ---...---- ---------- ---------- ---------- ---t--c---
    SiniGapC  ---...---- ------t--- ---------- ---------- ---t------
    BovGapC  ---cct-c-t t--c-ttc-- taca-g-tct --a----cc- g--t---t-c
```

FIG. 7A

```
           151                                                          200
DysGapC ACTCAAGGAC GTTTTGACGG AACTGTTGAA GTTAAAGAAG GTGGATTTGA
SpyGapC ---------- -------t-- a--a------ ---------- -------t--
SeqGapC --------a- ---------- a--t------ ---------- -------t--
ParaUbGapC ---------- ---------- ---t--a--- --------t- -------t--
UberGapc ---------- ----c----- ---a------ --------t- -------c--
AgalGapCDNA ---------- ----c----- ---t------ ---------- -------c--
SiniGapC ---------- ---------- ---a------ --------t- -------c--
BovGapC --c--c--ca ag--ca---- c--a--ca-g -cag-ga-c- -gaagc-c-t 201                                                          250
DysGapC AGTAAACGGA AACTTCATCA AAGTTTCTGC TGAACGTGAT CCAGAAAACA
SpyGapC ---a------ ---------- ---------- ------t--- ----------
SeqGapC ---a------ ---------- ---------- ------t--- ----------
ParaUbGapC c--------- --a-----t- ---------- ----aaa--- ------c-a-
UberGapc ---------- ---------- ---------- ----aaa--- ----------
AgalGapCDNA --------t c-a--tg-t- ---------- ------c--a ----c-----
SiniGapC ---------- -g---tg-t- ---------- a-----c--a ----c-----
BovGapC ca-c--t--- --ggc----- cca-c-tcca g--g--a--- --t-cc----

251                                                          300
DysGapC TCGACTGGGC AACTGACGGT GTTGAAATCG TTCTGGAAGC AACTGGTTTC
SpyGapC -c-------- ------t--g ---------- ---------- ----------
SeqGapC -c-------- ------c--- ---------- ---------- ----------
ParaUbGapC -t-------- ------c--- ---------- ---------- ----------
UberGapc -t-------- ------c--- --a------- ---------- ----------
AgalGapCDNA -t-------- t-----t--c --a------- ---------- ----------
SiniGapC -t-------- t-----t--- --a--c---- ---------- ---a------
BovGapC -ca-g----g tga--ct---- -c---gtat- -ag-g--gt- c-----gg--

301                                                          350
DysGapC TTTGCTAAAA AAGAAGCTGC TGAAAAACAC TTACATGCTA ACGGTGCTAA
SpyGapC ---------- -------a-- ---------- ---------- ----------
SeqGapC ---------- ---------- -------c-- ---------- ----------
ParaUbGapC ---------- ---c------ ---------t ------aa- -t--------
UberGapc ---------- ---c------ ---------t ---------- ----------
AgalGapCDNA -----atc-- -----aaa-- --g-c----- a-c----aa- -t--------
SiniGapC --c---tct- ---c------ ----c----- a-t--c---- -------g--
BovGapC --ca---cc- tg--gaag-- --gggct--- --ga-g-g-. ..---c--c--

351                                                          400
DysGapC AAAAGTTGTT ATCACAGCTC CTGGTGGAAA CGACGTTAAA ACAGTTGTTT
SpyGapC ---------- ---------- ---------- ---t------ ---------.
SeqGapC ---------- ---------- ---------- -------.-- ----------
ParaUbGapC ---------- -----t---- --------g- t-----g--- --------a-
UberGapc ---------- ---------- --------g- t--t------ --t-----a-
AgalGapCDNA ---------- ---------- ---------- ---------- ----------
SiniGapC ---------- ---------- ---------- t--------- ----------
BovGapC g-gg--ca-c ---t-t--a- --tc--...c ---t-ccccc -tgt----ga
```

FIG. 7B

```
            401                                                        450
DysGapC  TCAACACTAA CCACGA.CAT TCTTGACGGT ACTGAAACAG TTATCTCAGG
SpyGapC  ---------- ------.--- ---------- ---------- ----------
SeqGapC  ---------- ---------- ---------- ---------- ----------
ParaUbGapC -t-------- ---t--.t-- c-----t--a ---------- ----t-----
UberGapc -t-----a-- ---t--.--- ---------- --a-----t- -a--t-----
AgalGapCDNA ---------- ------.t-- c-----t--a ---------- ----------
SiniGapC a--------- ---t--.t-- ------t--a ---------- ----------
BovGapC  -ggg-gtg-- -------a-g -.a-a--aac --cctc-aga --g--agcaa 451                                                        500
DysGapC  TGCTTCATGT ACTACAAACT GTTTAGCTCC TATGGCTAAA GCTCTTCACG
SpyGapC  ---------- ---------- ---------- t--------- ---c-t--c-
SeqGapC  ---------- ---------- ---------- t--------- ---c-t--c-
ParaUbGapC ---------- ---------- ---------- ---------- -----a----
UberGapc ---------- ----t----- ---------- ---------- -----g----
AgalGapCDNA ---------- ---------- --c-t----- ---------- -----a----
SiniGapC ---------- ---------- ---------- ---------- --a--a----
BovGapC  ---c--c--c --c--c---- -c--g--c-- cc----c--g -tca-c--t-

501                                                        550
DysGapC  ATGCATTTGG TATCCAAAAA GGTCTTATGA CTACAATCCA CGCTTATACT
SpyGapC  --gca--c-- -a--c--a-- ---c------ ----a----- ----------
SeqGapC  --gca----- -a--c--a-- ---c------ ----a----- ----------
ParaUbGapC ---------- cg-a------ ---t-a---- ----a----- ----------
UberGapc ---------- -g-------- ---t-g---- -a--t----- ----------
AgalGapCDNA -c-------- -g-------- ---t-g---- ----t----- ---a------
SiniGapC ---------- -g-a------ ---t-a---- ----t----- t-g-------
BovGapC  -cc------- ca-cgtgg-g --ac------ -c--tg---- ---cat----

551                                                        600
DysGapC  GGTGACCAAA TGATCCTTGA CGGACCACAC CGTGGTGGTG ACCTTCGTCG
SpyGapC  ---------- ---------- ---------- ---------- ----------
SeqGapC  ---------- -----g---- t----ac-gt g--------- -t--------
ParaUbGapC -----t---- --c-t----- t-----t--- ---------- --t-a-----
UberGapc ---------- ---------- ---------- ---------- ----------
AgalGapCDNA ---------- ---------- ---------- ---------- ----------
SiniGapC ---------- --g-t----- ---------- ---------- -t--------
BovGapC  -ccac---g- a--ctg-g-- t--c--ctc- ...--gaagc tgtgg---ga 601                                                        650
DysGapC  TGCTCGTGCT GGTGCTGCAA ACATTGTTCC TAACTCAACT GGTGCTGCTA
SpyGapC  ---a--c--- ---------- ---------- ---------- ----------
SeqGapC  ---------- ---------- ---------- ---------- ------cg--
ParaUbGapC ---c------ ------aac- -t--t----- ---------- ----------
UberGapc ---------- -----aagc- ----t----- ---------- ----------
AgalGapCDNA ---------a ---------- ---------- ---------- ---------a-
SiniGapC ---------a -c---a---- ---------- ---------- ----------
BovGapC  c-gc--a-gg -c---ccag- -t---a-c-- -gct--t--- --c-----c-
```

FIG. 7C

```
             651                                                           700
DysGapC   AAGCTATCGG TCTTGTTATC CCAGAATTGA ATGGTAAACT TGATGGTGCT
SpyGapC   ---------- ---------- ------c-t- -c-------- ----------
SeqGapC   ---------- ---------- --------g- -c-------- ----------
ParaUbGapC ----a----- ---------- --t------a -t-------- ----------
UberGapc  ---a----- ------a--- ---------a- -t-------- ----------
AgalGapCDNA ---------- a--------- --------g- -c-------- ---t------
SiniGapC  ----a----- ---------- --------a- -t-------- ----------
BovGapC   -g--cg-g-- caag--c--- --t--gc-c- -c--g--g-- cact--catg 701                                                           750
DysGapC   GCACAACGTG TTCCTGTTCC AACTGGATCA GTAACTGAGT TGGTTGTAAC
SpyGapC   ---------- ---------- ---------- --------g- ------t---
SeqGapC   ---------- ---------- ---------- --------g- ------t---
ParaUbGapC ---------- -a--a----- ---a--t--- -----a---- -a--a---gt
UberGapc  ---------- ---------- ---------- ---------- -a--a---gt
AgalGapCDNA ---------- ---------- ---------- ---------- ----------
SiniGapC  ---------- ---------- ---------- ---------- -a--a---gt
BovGapC   --cttc--c- -c--cac--- c-ac-tg--t --tgtg--tc --acctgccg 751                                                           800
DysGapC   TCTTGATAAA AACGTTTCTG TTGACGAAAT CAACGCTGCT ATGAAAGCTG
SpyGapC   ------c--- a---t----- ----c----- ----t-t--- ----------
SeqGapC   ------c--- a---t----- ----c----- ------t--- ----------
ParaUbGapC ----a-t--- --aac---a- -a-------- t---t---ta ----------
UberGapc  ---------- --aac---a- ---------- ---------a --------a-
AgalGapCDNA ---------- ----taa--- -c------g- a--t------ --------a-
SiniGapC  ---------- --tac---a- -a-------- ---t------ --------a-
BovGapC   c--g--g--- cct-ccaagt a---t--g-- ---gaag-tg g----gcag- 801                                                           850
DysGapC   CTTCAAACGA CAGTTTCGGT TACACTGAAG ATCCAATTGT TTCTTCAGAT
SpyGapC   --t------- -agc-t---- ---------- ---------- t---------
SeqGapC   --t------- -agc-t---- ---------- ---------- t---------
ParaUbGapC -ag-t--t-- -----at--- ---------- ---------- ---a--t---
UberGapc  --g------- -----a---a ---------- -c-------- ------t---
AgalGapCDNA -ag-t----- -----a---- --t------- ---------- ---a--t---
SiniGapC  -ag-t----- -----a---- ---------- --g-t----- ---a------
BovGapC   -gt--g-g-g cc-tct-aag gg--t-ct-- gctac-ct-a ggaccag-t-

851                                                           900
DysGapC   ATCGTAGGCG TGTCATA... CGGTTCATTG TTTGACGCAA CTCAAACTAA
SpyGapC   --------cg -a-----... ---------- -----c-a-- ----------
SeqGapC   --------cg -a-----... ---------- -----c-a-- ----------
ParaUbGapC -----t--ta ----t-t... ---------a --c------- ----------
UberGapc  ---a-c-ta --g-t--... ---------- ---------- ----------
AgalGapCDNA -----t--ta -t-----... ---------- ---------- ----------
SiniGapC  --------ta -t-t---... ---------a ---------- ----------
BovGapC   g--tcct-cg ac-tca-cag --a-a-tcac -c-tc-a-ct tcg-tg--gg
```

FIG. 7D

```
                901                                                           950
DysGapC   AGTTATGGAA GTTGACGGAT CACAATTGGT TAAAGTTGTA TCATGGTATG
SpyGapC   ---aatggaa -----c---t ca-------- ---------a ----------
SeqGapC   ---tatggaa -----t---t ca-------- ---------a ----------
ParaUbGapC ---a------ -----t---- -t-----a-- ---------- ----------
UberGapc  ---a------ -----t---- -t-----a-- ---------- ----------
AgalGapCDNA ---t------ -----c--t- -c-------- ---------- --------c-
SiniGapC  ---a------ -----t---- -t-------- ---------- ----------
BovGapC   g-ctggc-t- -ccctcaacg -c--c--t-- c--gc-ca-- --c-----c-

951                                                          1000
DysGapC   ACAATGAAAT GTCTTACACT GCTCAACTTG TTCGTACACT TGAGTATTTT
SpyGapC   ----c----- ---------- ---------- -a-----t-- ---------c
SeqGapC   ----c----- ---------- ---------- ---------- ----------
ParaUbGapC ----t----- ---------- ---------- a--------- ----------
UberGapc  ----c----- ---------- --a------- -------t-- ----------
AgalGapCDNA -t--c----- ---a------ t-a------- ---------- ----------
SiniGapC  ----t----- ---------- ---------- -------t-- ----------
BovGapC   ----t---t- tggc----gc aaa--gg--- ---------- ----------

1001         1018
DysGapC   GCAAAAATCG CTAAATAA
SpyGapC   --------t- --------
SeqGapC   ---------- --------
ParaUbGapC ---------- --------
UberGapc  ---------- --------
AgalGapCDNA ---------- --------
SiniGapC  ---------- --------
BovGapC   ---------- --------
```

FIG. 7E

```
           1                                                         50
polyGap4   MKKITGIILL LLAVIILSAC QANYGSGMVV KVGINGFGRI GRLAFRRIQN
  SpyGapC  ---------- ---------- ---------- ---------- ----------
  SeqGapC  ---------- ---------- ---------- ---------- ----------
  DysGapC  ---------- ---------- ---------- ---------- ----------
PUberGapC  ---------- ---------- ---------- ---------- ----------
 UberGapC  ---------- ---------- ---------- ---------- ----------
 AgalGapC  ---------- ---------- ---------- ---------- ----------
IniaeGapC  ---------- ---------- ---------- ---------- ----------
  BovGapC  ---------- ---------- ---------- ---------- ----------

51                                                        100
polyGap4   VEGVEVTRIN DLTDPNMLAH LLKYDTTQGR FDGTVEVKEG GFEVNGNFIK
  DysGapC  ---------- ---------- ---------- ---------- ----------
  SpyGapC  i--------- ---------- ---------- ---------- ----------
  SeqGapC  ---------- ---------- ---------- ---------- ----------
PUberGapC  ---------- ---------- ---------- --------d- --d---k---
 UberGapC  ---------- ---------- ---------- --------d- ----------
 AgalGapC  ---------- ---------- ---------- ---------- ------q-v-
IniaeGapC  ---------- ---------- ---------- --------d- ------s-v-
  BovGapC  ---------- ---------- ---------- ---------- ----------
```

FIG. 8A

```
             101                                                           150
polyGap4    VSAERDPENI DWATDGVEIV LEALEGTVEV KDGGFDVNGK FIKVSAEKDP
  DysGapC   ---------. .......... .......... .......... ..........
  SpyGapC   ---------. .......... .......... .......... ..........
  SeqGapC   ---------. .......... .......... .......... ..........
 PUberGapC  ----k----. .......... .......... .......... ..........
  UberGapC  ----k----. .......... .......... .......... ..........
  AgalGapC  -----e-a-. .......... .......... .......... ..........
 IniaeGapC  -----e-a-. .......... .......... .......... ..........
  BovGapC   ---------- ---------- --rigrl-tr aafnsgkvdi vaindpfi-l 151                                                           200
polyGap4    EQIDWATDGV EIVLEIDGTV EVKEGGFEVN GQFVKVSAER EPANIDWATD
  DysGapC   .......... .......... .......... .........- ------
  SpyGapC   .......... .......... .......... .........- ------
  SeqGapC   .......... .......... .......... .........- ------
 PUberGapC  .......... .......... .......... ....q----- ------
  UberGapC  .......... .......... .......... .......... ------
  AgalGapC  .......... .......... .......... ......... - ------
 IniaeGapC  .......... .......... .......... .......... ------
  BovGapC   hymvymfqyd sthgkfn--- kaen-klvi- -kaitifq-- d----k-gda 201                                                           250
polyGap4    GVEIVLEATS FFAKKEAAEK HLHANGAKKV VITAPGGNDV KTVVFNTNHD
  DysGapC   ---------- ---------- ---------- ---------- ----------
  SpyGapC   ---------- ---------- ---------- ---------- ----------
  SeqGapC   ---------- ---------- p--------- ---------- -qlfstltts
 PUberGapC  ---------- -----a---- ---e------ -------d-- ----------
  UberGapC  ---------- -----a---- ---------- -------d-- ----------
  AgalGapC  ---------- ---s--k-gq -i-e------ ---------- ----------
 IniaeGapC  --d------- ---s-a---q -i-------- ---------- ----y-----
  BovGapC   -a-y-v-s-- v-ttm-k-ga --.kg---r- i-s--sa.-a pmf-mgv--e 251                                                           300
polyGap4    ILDGTETVIS GASCTTNCLA PMAKALHDAF GIQKGLMTTI HAYTGDQMIL
  DysGapC   ---------- ---------- ---------- ---------- ----------
  SpyGapC   ---------- ---------- ---------- ---------- ----------
  SeqGapC   ---------- ---------- ---------- ---------- ---------v
 PUberGapC  ---------- ---------- ------q-n- -vkq------ --------l-
  UberGapC  ---------- ---------- ------q-n- -vkq------ ----------
  AgalGapC  ---------- ---------- ------q-n- -vkq------ ----------
 IniaeGapC  ---------- ---------- ------q-n- -vkq------ -g------v-
  BovGapC   kynn-lkiv- n--------- -l--vi--h- --ve-----v --i-at-ktv
```

FIG. 8B

```
              301                                                        350
 polyGap4  DGPHRGGDLR  RARAGAANIV  PNSTGAAKAI  GLVIPELNGK  LDGAAQRVPV
  DysGapC  ----------  ----------  ----------  ----------  ----------
  SpyGapC  ----------  ----------  ----------  ----------  ----------
  SeqGapC  --hrg-----  ----------  ------r---  ----------  ----------
PUberGapC  ----------  ------n---  ----------  ----------  ----------
 UberGapC  ----------  ------s---  ----------  ----------  ----------
 AgalGapC  ----------  ----------  ----------  ----------  ----------
IniaeGapC  ----------  ----a-----  ----------  ----------  ----------
  BovGapC  ----.s-klw-  dg-ga-q--i  -a-------v  -k--------  -t-m-f---t 351                                                        400
 polyGap4  PTGSVTELVV  TLDKNVSVDE  INAAMKAASN  DS....FGYT  EDPIVSSDIV
  DysGapC  ----------  ----------  ----------  --....----  ----------
  SpyGapC  ----------  ----------  --s-------  --....----  ----------
  SeqGapC  ----------  ----------  ----------  --....----  ----------
PUberGapC  ---------a  v-n-et--e-  --sv----a-  --....y---  ----------
 UberGapC  ---------a  v-e-et--e-  --------a-  --....y---  ---------i
 AgalGapC  ---------a  --e-d-t-e-  v-------a-  --....y---  ----------
IniaeGapC  ---------a  v-e-dt--e-  --------a-  --....y---  --a-------
  BovGapC  -nv--vd-tc  r-e-paky--  -kkvv-q--e  gplkgil---  --qv--c-fn 401                                                        450
 polyGap4  GVSYGSLFDA  TQTKVMEVDG  SQLVKVVSWY  DNEMSYTAQL  VRTLEYFAKI
  DysGapC  ----------  ----------  ----------  ----------  ----------
  SpyGapC  ----------  ----------  ----------  ----------  ----------
  SeqGapC  ----------  ----------  ----------  ----------  ----------
PUberGapC  -m-f------  -----qt---  n---------  ----------  d---------
 UberGapC  -ma-------  -----qt---  n---------  ----------  ----------
 AgalGapC  -i--------  -----qt---  n---------  -------s--  ----------
IniaeGapC  -i--------  -----qt---  n---------  ----------  ----------
  BovGapC  sdths-t---  gagial...n  dhf--li---  ---fg-sk--  ----------

451
 polyGap4  AK
  DysGapC  --
  SpyGapC  --
  SeqGapC  --
PUberGapC  --
 UberGapC  --
 AgalGapC  --
IniaeGapC  --
  BovGapC  --
```

FIG. 8C

SEQUENCE LISTING

```
<160> NUMBER OF SEQ ID NOS: 22

<210> SEQ ID NO 1
<211> LENGTH: 37
<212> TYPE: DNA
<213> ORGANISM: Artificial Sequence
<220> FEATURE:
<223> OTHER INFORMATION: Description of Artificial Sequence: primer
      gapC1

<400> SEQUENCE: 1
ggcggcggca tatggtagtt aaagttggta ttaacgg                              37

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: primer
      gapC1r

<400> SEQUENCE: 2
gcggatcctt atttagcgat ttttgcaaag tactc                                35

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence: primer
      gap-1

<400> SEQUENCE: 3
aaaaaaggat ccggtatggt agttaaagtt gg                                   32

<210> SEQ ID NO 4
<211> LENGTH: 39
```

```
<212> TYPE: DNA
<213> ORGANISM: Artificial Sequence
<220> FEATURE:
<223> OTHER INFORMATION: Description of Artificial Sequence: primer
      Gap-2

<400> SEQUENCE: 4
aaaaaaccat ggttactcga gtgcttccag aacgatttc                              39

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: primer
      Gap-3

<400> SEQUENCE: 5
aaaaaactcg agggtactgt agaagttaaa g                                      31

<210> SEQ ID NO 6
<211> LENGTH: 45
<212> TYPE: DNA
<213> ORGANISM: Artificial Sequence
<220> FEATURE:
<223> OTHER INFORMATION: Description of Artificial Sequence: primer
      Gap-4

<400> SEQUENCE: 6
aaaaaaccat ggttaatcga tttcaagaac gatttcaaca ccgtc                       45

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence: primer
      Gap-5

<400> SEQUENCE: 7
aaaaaaatcg atggtactgt tgaagttaaa gaag                                   34

<210> SEQ ID NO 8
<211> LENGTH: 45
<212> TYPE: DNA
<213> ORGANISM: Artificial Sequence
<220> FEATURE:
<223> OTHER INFORMATION: Description of Artificial Sequence: primer
      Gap-6

<400> SEQUENCE: 8
aaaaaaccat ggttaactag ttgcttcaag aacgatttct acgcc                       45

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence: primer
      Gap-7

<400> SEQUENCE: 9
aaaaaaacta gtttctttgc taaaaagaa gctgc                                   35

<210> SEQ ID NO 10
<211> LENGTH: 42
<212> TYPE: DNA
```

<213> ORGANISM: Artificial Sequence
<220> FEATURE:
<223> OTHER INFORMATION: Description of Artificial Sequence: primer Gap-8

<400> SEQUENCE: 10
aaaaaaccat ggctattatt tagcgatttt tgcaaaatac tc    42

<210> SEQ ID NO 11
<211> LENGTH: 1011
<212> TYPE: DNA
<213> ORGANISM: Streptococcus dysgalactiae
<220> FEATURE:
<221> NAME/KEY: CDS
<222> LOCATION: (1)..(1011)

<400> SEQUENCE: 11

| | | | | | | | | | | | | | | | | |
|---|---|---|---|---|---|---|---|---|---|---|---|---|---|---|---|---|
| atg | gta | gtt | aaa | gtt | ggt | att | aac | ggt | ttc | ggt | cgt | atc | gga | cgt | ctt | 48 |
| Met | Val | Val | Lys | Val | Gly | Ile | Asn | Gly | Phe | Gly | Arg | Ile | Gly | Arg | Leu | |
| 1 | | | 5 | | | | | 10 | | | | | 15 | | | |
| gca | ttc | cgt | cgt | att | caa | aat | gtt | gaa | ggt | gtt | gaa | gta | act | cgt | atc | 96 |
| Ala | Phe | Arg | Arg | Ile | Gln | Asn | Val | Glu | Gly | Val | Glu | Val | Thr | Arg | Ile | |
| | | | 20 | | | | | 25 | | | | | 30 | | | |
| aac | gac | ctt | aca | gat | cca | aac | atg | ctt | gca | cac | ttg | ttg | aaa | tac | gat | 144 |
| Asn | Asp | Leu | Thr | Asp | Pro | Asn | Met | Leu | Ala | His | Leu | Leu | Lys | Tyr | Asp | |
| | | 35 | | | | | 40 | | | | | 45 | | | | |
| aca | act | caa | gga | cgt | ttt | gac | gga | act | gtt | gaa | gtt | aaa | gaa | ggt | gga | 192 |
| Thr | Thr | Gln | Gly | Arg | Phe | Asp | Gly | Thr | Val | Glu | Val | Lys | Glu | Gly | Gly | |
| | 50 | | | | | 55 | | | | | 60 | | | | | |
| ttt | gaa | gta | aac | gga | aac | ttc | atc | aaa | gtt | tct | gct | gaa | cgt | gat | cca | 240 |
| Phe | Glu | Val | Asn | Gly | Asn | Phe | Ile | Lys | Val | Ser | Ala | Glu | Arg | Asp | Pro | |
| 65 | | | | | 70 | | | | | 75 | | | | | 80 | |
| gaa | aac | atc | gac | tgg | gca | act | gac | ggt | gtt | gaa | atc | gtt | ctg | gaa | gca | 288 |
| Glu | Asn | Ile | Asp | Trp | Ala | Thr | Asp | Gly | Val | Glu | Ile | Val | Leu | Glu | Ala | |
| | | | | 85 | | | | | 90 | | | | | 95 | | |
| act | ggt | ttc | ttt | gct | aaa | aaa | gaa | gct | gct | gaa | aaa | cac | tta | cat | gct | 336 |
| Thr | Gly | Phe | Phe | Ala | Lys | Lys | Glu | Ala | Ala | Glu | Lys | His | Leu | His | Ala | |
| | | | 100 | | | | | 105 | | | | | 110 | | | |
| aac | ggt | gct | aaa | aaa | gtt | gtt | atc | aca | gct | cct | ggt | gga | aac | gac | gtt | 384 |
| Asn | Gly | Ala | Lys | Lys | Val | Val | Ile | Thr | Ala | Pro | Gly | Gly | Asn | Asp | Val | |
| | | 115 | | | | | 120 | | | | | 125 | | | | |
| aaa | aca | gtt | gtt | ttc | aac | act | aac | cac | gac | att | ctt | gac | ggt | act | gaa | 432 |
| Lys | Thr | Val | Val | Phe | Asn | Thr | Asn | His | Asp | Ile | Leu | Asp | Gly | Thr | Glu | |
| | 130 | | | | | 135 | | | | | 140 | | | | | |
| aca | gtt | atc | tca | ggt | gct | tca | tgt | act | aca | aac | tgt | tta | gct | cct | atg | 480 |
| Thr | Val | Ile | Ser | Gly | Ala | Ser | Cys | Thr | Thr | Asn | Cys | Leu | Ala | Pro | Met | |
| 145 | | | | | 150 | | | | | 155 | | | | | 160 | |
| gct | aaa | gct | ctt | cac | gat | gca | ttt | ggt | atc | caa | aaa | ggt | ctt | atg | act | 528 |
| Ala | Lys | Ala | Leu | His | Asp | Ala | Phe | Gly | Ile | Gln | Lys | Gly | Leu | Met | Thr | |
| | | | | 165 | | | | | 170 | | | | | 175 | | |
| aca | atc | cac | gct | tat | act | ggt | gac | caa | atg | atc | ctt | gac | gga | cca | cac | 576 |
| Thr | Ile | His | Ala | Tyr | Thr | Gly | Asp | Gln | Met | Ile | Leu | Asp | Gly | Pro | His | |
| | | | 180 | | | | | 185 | | | | | 190 | | | |
| cgt | ggt | ggt | gac | ctt | cgt | cgt | gct | cgt | gct | ggt | gct | gca | aac | att | gtt | 624 |
| Arg | Gly | Gly | Asp | Leu | Arg | Arg | Ala | Arg | Ala | Gly | Ala | Ala | Asn | Ile | Val | |
| | | 195 | | | | | 200 | | | | | 205 | | | | |
| cct | aac | tca | act | ggt | gct | gct | aaa | gct | atc | ggt | ctt | gtt | atc | cca | gaa | 672 |
| Pro | Asn | Ser | Thr | Gly | Ala | Ala | Lys | Ala | Ile | Gly | Leu | Val | Ile | Pro | Glu | |
| | 210 | | | | | 215 | | | | | 220 | | | | | |
| ttg | aat | ggt | aaa | ctt | gat | ggt | gct | gca | caa | cgt | gtt | cct | gtt | cca | act | 720 |
| Leu | Asn | Gly | Lys | Leu | Asp | Gly | Ala | Ala | Gln | Arg | Val | Pro | Val | Pro | Thr | |
| 225 | | | | | 230 | | | | | 235 | | | | | 240 | |

```
gga tca gta act gag ttg gtt gta act ctt gat aaa aac gtt tct gtt     768
Gly Ser Val Thr Glu Leu Val Val Thr Leu Asp Lys Asn Val Ser Val
            245                 250                 255 gac gaa atc aac gct gct atg aaa gct gct tca aac gac agt ttc ggt     816
Asp Glu Ile Asn Ala Ala Met Lys Ala Ala Ser Asn Asp Ser Phe Gly
            260                 265                 270 tac act gaa gat cca att gtt tct tca gat atc gta ggc gtg tca tac     864
Tyr Thr Glu Asp Pro Ile Val Ser Ser Asp Ile Val Gly Val Ser Tyr
        275                 280                 285 ggt tca ttg ttt gac gca act caa act aaa gtt atg gaa gtt gac gga     912
Gly Ser Leu Phe Asp Ala Thr Gln Thr Lys Val Met Glu Val Asp Gly
    290                 295                 300 tca caa ttg gtt aaa gtt gta tca tgg tat gac aat gaa atg tct tac     960
Ser Gln Leu Val Lys Val Val Ser Trp Tyr Asp Asn Glu Met Ser Tyr
305                 310                 315                 320 act gct caa ctt gtt cgt aca ctt gag tac ttt gca aaa atc gct aaa    1008
Thr Ala Gln Leu Val Arg Thr Leu Glu Tyr Phe Ala Lys Ile Ala Lys
                325                 330                 335 taa                                                                 1011

<210> SEQ ID NO 12
<211> LENGTH: 336
<212> TYPE: PRT
<213> ORGANISM: Streptococcus dysgalactiae

<400> SEQUENCE: 12

Met Val Val Lys Val Gly Ile Asn Gly Phe Gly Arg Ile Gly Arg Leu
 1               5                  10                  15

Ala Phe Arg Arg Ile Gln Asn Val Glu Gly Val Glu Val Thr Arg Ile
             20                  25                  30

Asn Asp Leu Thr Asp Pro Asn Met Leu Ala His Leu Leu Lys Tyr Asp
         35                  40                  45

Thr Thr Gln Gly Arg Phe Asp Gly Thr Val Glu Val Lys Glu Gly Gly
     50                  55                  60

Phe Glu Val Asn Gly Asn Phe Ile Lys Val Ser Ala Glu Arg Asp Pro
65                  70                  75                  80

Glu Asn Ile Asp Trp Ala Thr Asp Gly Val Glu Ile Val Leu Glu Ala
                85                  90                  95

Thr Gly Phe Phe Ala Lys Lys Glu Ala Ala Glu Lys His Leu His Ala
            100                 105                 110

Asn Gly Ala Lys Lys Val Val Ile Thr Ala Pro Gly Gly Asn Asp Val
        115                 120                 125

Lys Thr Val Val Phe Asn Thr Asn His Asp Ile Leu Asp Gly Thr Glu
    130                 135                 140

Thr Val Ile Ser Gly Ala Ser Cys Thr Thr Asn Cys Leu Ala Pro Met
145                 150                 155                 160

Ala Lys Ala Leu His Asp Ala Phe Gly Ile Gln Lys Gly Leu Met Thr
                165                 170                 175

Thr Ile His Ala Tyr Thr Gly Asp Gln Met Ile Leu Asp Gly Pro His
            180                 185                 190

Arg Gly Gly Asp Leu Arg Arg Ala Arg Ala Gly Ala Ala Asn Ile Val
        195                 200                 205

Pro Asn Ser Thr Gly Ala Ala Lys Ala Ile Gly Leu Val Ile Pro Glu
    210                 215                 220

Leu Asn Gly Lys Leu Asp Gly Ala Ala Gln Arg Val Pro Val Pro Thr
225                 230                 235                 240
```

-continued

```
Gly Ser Val Thr Glu Leu Val Val Thr Leu Asp Lys Asn Val Ser Val
            245                 250                 255

Asp Glu Ile Asn Ala Ala Met Lys Ala Ala Ser Asn Asp Ser Phe Gly
            260                 265                 270

Tyr Thr Glu Asp Pro Ile Val Ser Ser Asp Ile Val Gly Val Ser Tyr
            275                 280                 285

Gly Ser Leu Phe Asp Ala Thr Gln Thr Lys Val Met Glu Val Asp Gly
            290                 295                 300

Ser Gln Leu Val Lys Val Val Ser Trp Tyr Asp Asn Glu Met Ser Tyr
305                 310                 315                 320

Thr Ala Gln Leu Val Arg Thr Leu Glu Tyr Phe Ala Lys Ile Ala Lys
            325                 330                 335

<210> SEQ ID NO 13
<211> LENGTH: 1011
<212> TYPE: DNA
<213> ORGANISM: Streptococcus agalactiae
<220> FEATURE:
<221> NAME/KEY: CDS
<222> LOCATION: (1)..(1011)

<400> SEQUENCE: 13 atg gta gtt aaa gtt ggt att aac ggt ttc ggt cgt atc ggt cgt ctt     48
Met Val Val Lys Val Gly Ile Asn Gly Phe Gly Arg Ile Gly Arg Leu
  1               5                  10                  15 gca ttc cgt cgc atc caa aac gta gaa ggt gtt gaa gtt act cgt atc     96
Ala Phe Arg Arg Ile Gln Asn Val Glu Gly Val Glu Val Thr Arg Ile
             20                  25                  30 aac gac ctt aca gat cca aac atg ctt gca cac ttg ttg aaa tat gac    144
Asn Asp Leu Thr Asp Pro Asn Met Leu Ala His Leu Leu Lys Tyr Asp
         35                  40                  45 aca act caa ggt cgt ttc gac ggt act gtt gaa gtt aaa gaa ggt gga    192
Thr Thr Gln Gly Arg Phe Asp Gly Thr Val Glu Val Lys Glu Gly Gly
     50                  55                  60 ttc gaa gtt aac ggt caa ttt gtt aaa gtt tct gct gaa cgc gaa cca    240
Phe Glu Val Asn Gly Gln Phe Val Lys Val Ser Ala Glu Arg Glu Pro
 65                  70                  75                  80 gca aac att gac tgg gct act gat ggc gta gaa atc gtt ctt gaa gca    288
Ala Asn Ile Asp Trp Ala Thr Asp Gly Val Glu Ile Val Leu Glu Ala
                 85                  90                  95 act ggt ttc ttt gca tca aaa gaa aaa gct gga caa cac atc cat gaa    336
Thr Gly Phe Phe Ala Ser Lys Glu Lys Ala Gly Gln His Ile His Glu
            100                 105                 110 aat ggt gct aaa aaa gtt gtt atc aca gct cct ggt gga aac gac gtt    384
Asn Gly Ala Lys Lys Val Val Ile Thr Ala Pro Gly Gly Asn Asp Val
        115                 120                 125 aaa aca gtt gtt ttc aac act aac cac gat atc ctt gat gga act gaa    432
Lys Thr Val Val Phe Asn Thr Asn His Asp Ile Leu Asp Gly Thr Glu
    130                 135                 140 aca gtt atc tca ggt gct tca tgt act aca aac tgt ctt gct cca atg    480
Thr Val Ile Ser Gly Ala Ser Cys Thr Thr Asn Cys Leu Ala Pro Met
145                 150                 155                 160 gct aaa gct tta caa gac aac ttt ggt gtt aaa caa ggt ttg atg act    528
Ala Lys Ala Leu Gln Asp Asn Phe Gly Val Lys Gln Gly Leu Met Thr
                165                 170                 175 act atc cac gca tac act ggt gac caa atg atc ctt gac gga cca cac    576
Thr Ile His Ala Tyr Thr Gly Asp Gln Met Ile Leu Asp Gly Pro His
            180                 185                 190 cgt ggt ggt gac ctt cgt cgt gct cgt gca ggt gct gca aac atc gtt    624
```

```
                                                                                    -continued Arg Gly Gly Asp Leu Arg Arg Ala Arg Ala Gly Ala Ala Asn Ile Val
            195                 200                 205 cct aac tca act ggt gct gca aaa gct atc gga ctt gtt atc cca gaa           672
Pro Asn Ser Thr Gly Ala Ala Lys Ala Ile Gly Leu Val Ile Pro Glu
210                 215                 220 ttg aac ggt aaa ctt gat ggt gct gca caa cgt gtt cct gtt cca act           720
Leu Asn Gly Lys Leu Asp Gly Ala Ala Gln Arg Val Pro Val Pro Thr
225                 230                 235                 240 gga tca gta act gaa ttg gtt gca act ctt gaa aaa gac gta act gtc           768
Gly Ser Val Thr Glu Leu Val Ala Thr Leu Glu Lys Asp Val Thr Val
            245                 250                 255 gaa gaa gta aat gca gct atg aaa gca gca gct aac gat tca tac ggt           816
Glu Glu Val Asn Ala Ala Met Lys Ala Ala Ala Asn Asp Ser Tyr Gly
            260                 265                 270 tat act gaa gat cca atc gta tca tct gat atc gtt ggt att tca tac           864
Tyr Thr Glu Asp Pro Ile Val Ser Ser Asp Ile Val Gly Ile Ser Tyr
            275                 280                 285 ggt tca ttg ttt gat gct act caa act aaa gtt caa act gtt gac ggt           912
Gly Ser Leu Phe Asp Ala Thr Gln Thr Lys Val Gln Thr Val Asp Gly
            290                 295                 300 aac caa ttg gtt aaa gtt gtt tca tgg tac gat aac gaa atg tca tac           960
Asn Gln Leu Val Lys Val Val Ser Trp Tyr Asp Asn Glu Met Ser Tyr
305                 310                 315                 320 act tca caa ctt gtt cgt aca ctt gag tac ttt gca aaa atc gct aaa          1008
Thr Ser Gln Leu Val Arg Thr Leu Glu Tyr Phe Ala Lys Ile Ala Lys
            325                 330                 335 taa                                                                      1011
```

<210> SEQ ID NO 14
<211> LENGTH: 336
<212> TYPE: PRT
<213> ORGANISM: Streptococcus agalactiae

<400> SEQUENCE: 14

```
Met Val Val Lys Val Gly Ile Asn Gly Phe Gly Arg Ile Gly Arg Leu
1               5                   10                  15

Ala Phe Arg Arg Ile Gln Asn Val Glu Gly Val Glu Val Thr Arg Ile
            20                  25                  30

Asn Asp Leu Thr Asp Pro Asn Met Leu Ala His Leu Leu Lys Tyr Asp
        35                  40                  45

Thr Thr Gln Gly Arg Phe Asp Gly Thr Val Glu Val Lys Glu Gly Gly
    50                  55                  60

Phe Glu Val Asn Gly Gln Phe Val Lys Val Ser Ala Glu Arg Glu Pro
65                  70                  75                  80

Ala Asn Ile Asp Trp Ala Thr Asp Gly Val Glu Ile Val Leu Glu Ala
                85                  90                  95

Thr Gly Phe Phe Ala Ser Lys Glu Lys Ala Gly Gln His Ile His Glu
            100                 105                 110

Asn Gly Ala Lys Lys Val Val Ile Thr Ala Pro Gly Gly Asn Asp Val
        115                 120                 125

Lys Thr Val Val Phe Asn Thr Asn His Asp Ile Leu Asp Gly Thr Glu
    130                 135                 140

Thr Val Ile Ser Gly Ala Ser Cys Thr Thr Asn Cys Leu Ala Pro Met
145                 150                 155                 160

Ala Lys Ala Leu Gln Asp Asn Phe Gly Val Lys Gln Gly Leu Met Thr
                165                 170                 175

Thr Ile His Ala Tyr Thr Gly Asp Gln Met Ile Leu Asp Gly Pro His
```

-continued

```
                    180                 185                 190
Arg Gly Gly Asp Leu Arg Arg Ala Arg Ala Gly Ala Ala Asn Ile Val
                195                 200                 205

Pro Asn Ser Thr Gly Ala Ala Lys Ala Ile Gly Leu Val Ile Pro Glu
            210                 215                 220

Leu Asn Gly Lys Leu Asp Gly Ala Ala Gln Arg Val Pro Val Pro Thr
225                 230                 235                 240

Gly Ser Val Thr Glu Leu Val Ala Thr Leu Glu Lys Asp Val Thr Val
                    245                 250                 255

Glu Glu Val Asn Ala Ala Met Lys Ala Ala Asn Asp Ser Tyr Gly
                260                 265                 270

Tyr Thr Glu Asp Pro Ile Val Ser Asp Ile Val Gly Ile Ser Tyr
            275                 280                 285

Gly Ser Leu Phe Asp Ala Thr Gln Thr Lys Val Gln Thr Val Asp Gly
                290                 295                 300

Asn Gln Leu Val Lys Val Ser Trp Tyr Asp Asn Glu Met Ser Tyr
305                 310                 315                 320

Thr Ser Gln Leu Val Arg Thr Leu Glu Tyr Phe Ala Lys Ile Ala Lys
                    325                 330                 335
```

<210> SEQ ID NO 15
<211> LENGTH: 1011
<212> TYPE: DNA
<213> ORGANISM: Streptococcus uberis
<220> FEATURE:
<221> NAME/KEY: CDS
<222> LOCATION: (1)..(1011)

<400> SEQUENCE: 15

```
atg gta gtt aaa gtt ggt att aac ggt ttc ggt cgt atc gga cgt ctt     48
Met Val Val Lys Val Gly Ile Asn Gly Phe Gly Arg Ile Gly Arg Leu
  1               5                  10                  15 gca ttc cgt cgt att caa aac gtt gaa ggt gtt gaa gta act cgt att     96
Ala Phe Arg Arg Ile Gln Asn Val Glu Gly Val Glu Val Thr Arg Ile
                 20                  25                  30 aac gat ctt act gac cca aat atg ctt gca cac ttg ttg aaa tat gat    144
Asn Asp Leu Thr Asp Pro Asn Met Leu Ala His Leu Leu Lys Tyr Asp
             35                  40                  45 aca act caa ggt cgt ttc gac ggt aca gtt gaa gtt aaa gat ggt gga    192
Thr Thr Gln Gly Arg Phe Asp Gly Thr Val Glu Val Lys Asp Gly Gly
         50                  55                  60 ttc gaa gtt aac gga aac ttc atc aaa gtt tct gct gaa aaa gat cca    240
Phe Glu Val Asn Gly Asn Phe Ile Lys Val Ser Ala Glu Lys Asp Pro
 65                  70                  75                  80 gaa aac att gac tgg gca act gac ggt gta gaa atc gtt ctt gaa gca    288
Glu Asn Ile Asp Trp Ala Thr Asp Gly Val Glu Ile Val Leu Glu Ala
                     85                  90                  95 act ggt ttc ttt gct aaa aaa gca gct gct gaa aaa cat tta cat gct    336
Thr Gly Phe Phe Ala Lys Lys Ala Ala Ala Glu Lys His Leu His Ala
                100                 105                 110 aac ggt gct aaa aaa gtt gtt atc aca gct cct ggt gga gat gat gtt    384
Asn Gly Ala Lys Lys Val Val Ile Thr Ala Pro Gly Gly Asp Asp Val
            115                 120                 125 aaa act gtt gta ttt aac aca aac cat gac att ctt gac ggt aca gaa    432
Lys Thr Val Val Phe Asn Thr Asn His Asp Ile Leu Asp Gly Thr Glu
        130                 135                 140 act gta att tca ggt gct tca tgt act act aac tgt tta gct cca atg    480
Thr Val Ile Ser Gly Ala Ser Cys Thr Thr Asn Cys Leu Ala Pro Met
145                 150                 155                 160
```

```
gct aaa gct ttg caa gat aac ttt ggt gtt aaa caa ggt ttg atg aca    528
Ala Lys Ala Leu Gln Asp Asn Phe Gly Val Lys Gln Gly Leu Met Thr
            165                 170                 175 act atc cac gct tac act ggt gac caa atg atc ctt gac gga cca cac    576
Thr Ile His Ala Tyr Thr Gly Asp Gln Met Ile Leu Asp Gly Pro His
        180                 185                 190 cgt ggt ggt gac ctt cgt cgt gct cgt gct ggt gca agc aac att gtt    624
Arg Gly Gly Asp Leu Arg Arg Ala Arg Ala Gly Ala Ser Asn Ile Val
    195                 200                 205 cct aac tca act ggt gct gct aaa gca atc ggt ctt gta atc cca gaa    672
Pro Asn Ser Thr Gly Ala Ala Lys Ala Ile Gly Leu Val Ile Pro Glu
210                 215                 220 tta aat ggt aaa ctt gac ggt gct gca caa cgt gtt cct gtt cca act    720
Leu Asn Gly Lys Leu Asp Gly Ala Ala Gln Arg Val Pro Val Pro Thr
225                 230                 235                 240 gga tca gta act gaa tta gta gca gtt ctt gaa aaa gaa act tca gtt    768
Gly Ser Val Thr Glu Leu Val Ala Val Leu Glu Lys Glu Thr Ser Val
                245                 250                 255 gaa gaa atc aac gca gca atg aaa gca gct gca aac gat tca tac gga    816
Glu Glu Ile Asn Ala Ala Met Lys Ala Ala Ala Asn Asp Ser Tyr Gly
            260                 265                 270 tac act gaa gac cca atc gta tct tct gat atc atc ggt atg gct tac    864
Tyr Thr Glu Asp Pro Ile Val Ser Ser Asp Ile Ile Gly Met Ala Tyr
        275                 280                 285 ggt tca ttg ttt gat gct act caa act aaa gta caa act gtt gat gga    912
Gly Ser Leu Phe Asp Ala Thr Gln Thr Lys Val Gln Thr Val Asp Gly
    290                 295                 300 aat caa tta gtt aaa gtt gtt tca tgg tat gac aac gaa atg tct tac    960
Asn Gln Leu Val Lys Val Val Ser Trp Tyr Asp Asn Glu Met Ser Tyr
305                 310                 315                 320 act gca caa ctt gtt cgt act ctt gag tac ttt gca aaa atc gct aaa   1008
Thr Ala Gln Leu Val Arg Thr Leu Glu Tyr Phe Ala Lys Ile Ala Lys
                325                 330                 335 taa                                                               1011

<210> SEQ ID NO 16
<211> LENGTH: 336
<212> TYPE: PRT
<213> ORGANISM: Streptococcus uberis

<400> SEQUENCE: 16

Met Val Val Lys Val Gly Ile Asn Gly Phe Gly Arg Ile Gly Arg Leu
 1               5                  10                  15

Ala Phe Arg Arg Ile Gln Asn Val Glu Gly Val Glu Val Thr Arg Ile
                20                  25                  30

Asn Asp Leu Thr Asp Pro Asn Met Leu Ala His Leu Leu Lys Tyr Asp
            35                  40                  45

Thr Thr Gln Gly Arg Phe Asp Gly Thr Val Glu Val Lys Asp Gly Gly
        50                  55                  60

Phe Glu Val Asn Gly Asn Phe Ile Lys Val Ser Ala Glu Lys Asp Pro
65                  70                  75                  80

Glu Asn Ile Asp Trp Ala Thr Asp Gly Val Glu Ile Val Leu Glu Ala
                85                  90                  95

Thr Gly Phe Phe Ala Lys Lys Ala Ala Glu Lys His Leu His Ala
            100                 105                 110

Asn Gly Ala Lys Lys Val Val Ile Thr Ala Pro Gly Gly Asp Asp Val
        115                 120                 125
```

```
Lys Thr Val Val Phe Asn Thr Asn His Asp Ile Leu Asp Gly Thr Glu
    130                 135                 140

Thr Val Ile Ser Gly Ala Ser Cys Thr Thr Asn Cys Leu Ala Pro Met
145                 150                 155                 160

Ala Lys Ala Leu Gln Asp Asn Phe Gly Val Lys Gln Gly Leu Met Thr
                165                 170                 175

Thr Ile His Ala Tyr Thr Gly Asp Gln Met Ile Leu Asp Gly Pro His
            180                 185                 190

Arg Gly Gly Asp Leu Arg Arg Ala Arg Ala Gly Ala Ser Asn Ile Val
        195                 200                 205

Pro Asn Ser Thr Gly Ala Ala Lys Ala Ile Gly Leu Val Ile Pro Glu
    210                 215                 220

Leu Asn Gly Lys Leu Asp Gly Ala Ala Gln Arg Val Pro Val Pro Thr
225                 230                 235                 240

Gly Ser Val Thr Glu Leu Val Ala Val Leu Glu Lys Glu Thr Ser Val
                245                 250                 255

Glu Glu Ile Asn Ala Ala Met Lys Ala Ala Ala Asn Asp Ser Tyr Gly
            260                 265                 270

Tyr Thr Glu Asp Pro Ile Val Ser Ser Asp Ile Ile Gly Met Ala Tyr
        275                 280                 285

Gly Ser Leu Phe Asp Ala Thr Gln Thr Lys Val Gln Thr Val Asp Gly
    290                 295                 300

Asn Gln Leu Val Lys Val Val Ser Trp Tyr Asp Asn Glu Met Ser Tyr
305                 310                 315                 320

Thr Ala Gln Leu Val Arg Thr Leu Glu Tyr Phe Ala Lys Ile Ala Lys
                325                 330                 335

<210> SEQ ID NO 17
<211> LENGTH: 1011
<212> TYPE: DNA
<213> ORGANISM: Streptococcus parauberis
<220> FEATURE:
<221> NAME/KEY: CDS
<222> LOCATION: (1)..(1011)

<400> SEQUENCE: 17 atg gta gtt aaa gtt ggt att aac ggt ttt ggc cgt atc gga cgt ctt    48
Met Val Val Lys Val Gly Ile Asn Gly Phe Gly Arg Ile Gly Arg Leu
  1               5                  10                  15 gct ttc cgt cgt att caa aat gta gaa ggt gtt gaa gtt act cgc atc    96
Ala Phe Arg Arg Ile Gln Asn Val Glu Gly Val Glu Val Thr Arg Ile
                 20                  25                  30 aac gac ctt aca gat cca aat atg ctt gca cac ttg tta aaa tac gat   144
Asn Asp Leu Thr Asp Pro Asn Met Leu Ala His Leu Leu Lys Tyr Asp
             35                  40                  45 aca act caa ggt cgt ttt gac ggt act gta gaa gtt aaa gat ggt gga   192
Thr Thr Gln Gly Arg Phe Asp Gly Thr Val Glu Val Lys Asp Gly Gly
         50                  55                  60 ttt gac gtt aac gga aaa ttc att aaa gtt tct gct gaa aaa gat cca   240
Phe Asp Val Asn Gly Lys Phe Ile Lys Val Ser Ala Glu Lys Asp Pro
 65                  70                  75                  80 gaa caa att gac tgg gca act gac ggt gtt gaa atc gtt ctt gaa gca   288
Glu Gln Ile Asp Trp Ala Thr Asp Gly Val Glu Ile Val Leu Glu Ala
                 85                  90                  95 act ggt ttc ttt gct aaa aaa gca gct gct gaa aaa cat tta cat gaa   336
Thr Gly Phe Phe Ala Lys Lys Ala Ala Ala Glu Lys His Leu His Glu
                100                 105                 110 aat ggt gct aaa aaa gtt gtt atc act gct cct ggt gga gat gac gtg   384
```

-continued

```
                Asn Gly Ala Lys Lys Val Val Ile Thr Ala Pro Gly Gly Asp Asp Val
                            115                 120                 125 aaa aca gtt gta ttt aac act aac cat gat atc ctt gat gga act gaa       432
Lys Thr Val Val Phe Asn Thr Asn His Asp Ile Leu Asp Gly Thr Glu
130                 135                 140 aca gtt att tca ggt gct tca tgt act aca aac tgt tta gct cca atg       480
Thr Val Ile Ser Gly Ala Ser Cys Thr Thr Asn Cys Leu Ala Pro Met
145                 150                 155                 160 gct aaa gct tta caa gat aac ttt ggc gta aaa caa ggt tta atg act       528
Ala Lys Ala Leu Gln Asp Asn Phe Gly Val Lys Gln Gly Leu Met Thr
                165                 170                 175 aca atc cac gct tac act ggt gat caa atg ctt ctt gat gga cct cac       576
Thr Ile His Ala Tyr Thr Gly Asp Gln Met Leu Leu Asp Gly Pro His
            180                 185                 190 cgt ggt ggt gac tta cgt cgt gcc cgt gct ggt gct aac aat att gtt       624
Arg Gly Gly Asp Leu Arg Arg Ala Arg Ala Gly Ala Asn Asn Ile Val
        195                 200                 205 cct aac tca act ggt gct gct aaa gca atc ggt ctt gtt atc cct gaa       672
Pro Asn Ser Thr Gly Ala Ala Lys Ala Ile Gly Leu Val Ile Pro Glu
    210                 215                 220 tta aat ggt aaa ctt gac ggt gct gca caa cgt gta cca gtt cca aca       720
Leu Asn Gly Lys Leu Asp Gly Ala Ala Gln Arg Val Pro Val Pro Thr
225                 230                 235                 240 ggt tca gta aca gaa tta gta gca gtt ctt aat aaa gaa act tca gta       768
Gly Ser Val Thr Glu Leu Val Ala Val Leu Asn Lys Glu Thr Ser Val
                245                 250                 255 gaa gaa att aac tca gta atg aaa gct gca gct aat gat tca tat ggt       816
Glu Glu Ile Asn Ser Val Met Lys Ala Ala Ala Asn Asp Ser Tyr Gly
                260                 265                 270 tac act gaa gat cca atc gta tca tct gat atc gtt ggt atg tct ttc       864
Tyr Thr Glu Asp Pro Ile Val Ser Ser Asp Ile Val Gly Met Ser Phe
            275                 280                 285 ggt tca tta ttc gat gct act caa act aaa gta caa act gtt gat gga       912
Gly Ser Leu Phe Asp Ala Thr Gln Thr Lys Val Gln Thr Val Asp Gly
        290                 295                 300 aat caa tta gtt aaa gtt gtt tca tgg tat gac aat gaa atg tct tac       960
Asn Gln Leu Val Lys Val Val Ser Trp Tyr Asp Asn Glu Met Ser Tyr
305                 310                 315                 320 act gct caa ctt gat cgt aca ctt gag tac ttt gca aaa atc gct aaa      1008
Thr Ala Gln Leu Asp Arg Thr Leu Glu Tyr Phe Ala Lys Ile Ala Lys
                325                 330                 335 taa                                                                  1011
```

<210> SEQ ID NO 18
<211> LENGTH: 336
<212> TYPE: PRT
<213> ORGANISM: Streptococcus parauberis

<400> SEQUENCE: 18

```
Met Val Val Lys Val Gly Ile Asn Gly Phe Gly Arg Ile Gly Arg Leu
1               5                   10                  15

Ala Phe Arg Arg Ile Gln Asn Val Glu Gly Val Glu Val Thr Arg Ile
            20                  25                  30

Asn Asp Leu Thr Asp Pro Asn Met Leu Ala His Leu Leu Lys Tyr Asp
        35                  40                  45

Thr Thr Gln Gly Arg Phe Asp Gly Thr Val Glu Val Lys Asp Gly Gly
    50                  55                  60

Phe Asp Val Asn Gly Lys Phe Ile Lys Val Ser Ala Glu Lys Asp Pro
65                  70                  75                  80
```

```
Glu Gln Ile Asp Trp Ala Thr Asp Gly Val Glu Ile Val Leu Glu Ala
                85                  90                  95

Thr Gly Phe Phe Ala Lys Lys Ala Ala Glu Lys His Leu His Glu
            100                 105                 110

Asn Gly Ala Lys Lys Val Val Ile Thr Ala Pro Gly Gly Asp Asp Val
            115                 120                 125

Lys Thr Val Val Phe Asn Thr Asn His Asp Ile Leu Asp Gly Thr Glu
130                 135                 140

Thr Val Ile Ser Gly Ala Ser Cys Thr Thr Asn Cys Leu Ala Pro Met
145                 150                 155                 160

Ala Lys Ala Leu Gln Asp Asn Phe Gly Val Lys Gln Gly Leu Met Thr
                165                 170                 175

Thr Ile His Ala Tyr Thr Gly Asp Gln Met Leu Leu Asp Gly Pro His
                180                 185                 190

Arg Gly Gly Asp Leu Arg Arg Ala Arg Ala Gly Ala Asn Asn Ile Val
            195                 200                 205

Pro Asn Ser Thr Gly Ala Ala Lys Ala Ile Gly Leu Val Ile Pro Glu
210                 215                 220

Leu Asn Gly Lys Leu Asp Gly Ala Ala Gln Arg Val Pro Val Pro Thr
225                 230                 235                 240

Gly Ser Val Thr Glu Leu Val Ala Val Leu Asn Lys Glu Thr Ser Val
                245                 250                 255

Glu Glu Ile Asn Ser Val Met Lys Ala Ala Asn Asp Ser Tyr Gly
            260                 265                 270

Tyr Thr Glu Asp Pro Ile Val Ser Ser Asp Ile Val Gly Met Ser Phe
            275                 280                 285

Gly Ser Leu Phe Asp Ala Thr Gln Thr Lys Val Gln Thr Val Asp Gly
            290                 295                 300

Asn Gln Leu Val Lys Val Val Ser Trp Tyr Asp Asn Glu Met Ser Tyr
305                 310                 315                 320

Thr Ala Gln Leu Asp Arg Thr Leu Glu Tyr Phe Ala Lys Ile Ala Lys
                325                 330                 335

<210> SEQ ID NO 19
<211> LENGTH: 1011
<212> TYPE: DNA
<213> ORGANISM: Streptococcus iniae
<220> FEATURE:
<221> NAME/KEY: CDS
<222> LOCATION: (1)..(1011)

<400> SEQUENCE: 19 atg gta gtt aaa gtt ggt att aac ggt ttc gga cgt atc ggt cgt ctt    48
Met Val Val Lys Val Gly Ile Asn Gly Phe Gly Arg Ile Gly Arg Leu
  1               5                  10                  15 gca ttc cgt cgt att caa aat gtt gaa ggt gtt gaa gta act cgt atc    96
Ala Phe Arg Arg Ile Gln Asn Val Glu Gly Val Glu Val Thr Arg Ile
                20                  25                  30 aat gac ctt aca gat cct aac atg ctt gca cac ttg ttg aaa tat gat   144
Asn Asp Leu Thr Asp Pro Asn Met Leu Ala His Leu Leu Lys Tyr Asp
            35                  40                  45 aca act caa ggt cgt ttt gac ggt aca gtt gaa gtt aaa gat ggt gga   192
Thr Thr Gln Gly Arg Phe Asp Gly Thr Val Glu Val Lys Asp Gly Gly
        50                  55                  60 ttc gaa gtt aac gga agc ttt gtt aaa gtt tct gca gaa cgc gaa cca   240
Phe Glu Val Asn Gly Ser Phe Val Lys Val Ser Ala Glu Arg Glu Pro
65                  70                  75                  80
```

```
gca aac att gac tgg gct act gat ggt gta gac atc gtt ctt gaa gca      288
Ala Asn Ile Asp Trp Ala Thr Asp Gly Val Asp Ile Val Leu Glu Ala
             85                  90                  95 aca ggt ttc ttc gct tct aaa gca gct gct gaa caa cac att cac gct      336
Thr Gly Phe Phe Ala Ser Lys Ala Ala Ala Glu Gln His Ile His Ala
        100                 105                 110 aac ggt gcg aaa aaa gtt gtt atc aca gct cct ggt gga aat gac gtt      384
Asn Gly Ala Lys Lys Val Val Ile Thr Ala Pro Gly Gly Asn Asp Val
            115                 120                 125 aaa aca gtt gtt tac aac act aac cat gat att ctt gat gga act gaa      432
Lys Thr Val Val Tyr Asn Thr Asn His Asp Ile Leu Asp Gly Thr Glu
130                 135                 140 aca gtt atc tca ggt gct tca tgt act aca aac tgt tta gct cca atg      480
Thr Val Ile Ser Gly Ala Ser Cys Thr Thr Asn Cys Leu Ala Pro Met
145                 150                 155                 160 gct aaa gca tta caa gat aac ttt ggt gta aaa caa ggt tta atg act      528
Ala Lys Ala Leu Gln Asp Asn Phe Gly Val Lys Gln Gly Leu Met Thr
                165                 170                 175 act atc cat ggt tac act ggt gac caa atg gtt ctt gac gga cca cac      576
Thr Ile His Gly Tyr Thr Gly Asp Gln Met Val Leu Asp Gly Pro His
            180                 185                 190 cgt ggt ggt gat ctt cgt cgt gct cgt gca gct gca gca aac atc gtt      624
Arg Gly Gly Asp Leu Arg Arg Ala Arg Ala Ala Ala Ala Asn Ile Val
        195                 200                 205 cct aac tca act ggt gct gct aaa gca atc ggt ctt gtt atc cca gaa      672
Pro Asn Ser Thr Gly Ala Ala Lys Ala Ile Gly Leu Val Ile Pro Glu
    210                 215                 220 tta aat ggt aaa ctt gac ggt gct gca caa cgt gtt cct gtt cca act      720
Leu Asn Gly Lys Leu Asp Gly Ala Ala Gln Arg Val Pro Val Pro Thr
225                 230                 235                 240 gga tca gta act gaa tta gta gca gtt ctt gaa aaa gat act tca gta      768
Gly Ser Val Thr Glu Leu Val Ala Val Leu Glu Lys Asp Thr Ser Val
                245                 250                 255 gaa gaa atc aat gca gct atg aaa gca gca gct aac gat tca tac ggt      816
Glu Glu Ile Asn Ala Ala Met Lys Ala Ala Ala Asn Asp Ser Tyr Gly
            260                 265                 270 tac act gaa gat gct atc gta tca tca gat atc gta ggt att tct tac      864
Tyr Thr Glu Asp Ala Ile Val Ser Ser Asp Ile Val Gly Ile Ser Tyr
        275                 280                 285 ggt tca tta ttt gat gct act caa act aaa gta caa act gtt gat gga      912
Gly Ser Leu Phe Asp Ala Thr Gln Thr Lys Val Gln Thr Val Asp Gly
    290                 295                 300 aat caa ttg gtt aaa gtt gtt tca tgg tat gac aat gaa atg tct tac      960
Asn Gln Leu Val Lys Val Val Ser Trp Tyr Asp Asn Glu Met Ser Tyr
305                 310                 315                 320 act gct caa ctt gtt cgt act ctt gag tac ttt gca aaa atc gct aaa     1008
Thr Ala Gln Leu Val Arg Thr Leu Glu Tyr Phe Ala Lys Ile Ala Lys
                325                 330                 335 taa                                                                 1011

<210> SEQ ID NO 20
<211> LENGTH: 336
<212> TYPE: PRT
<213> ORGANISM: Streptococcus iniae

<400> SEQUENCE: 20

Met Val Val Lys Val Gly Ile Asn Gly Phe Gly Arg Ile Gly Arg Leu
  1               5                  10                  15

Ala Phe Arg Arg Ile Gln Asn Val Glu Gly Val Glu Val Thr Arg Ile
```

```
                  20                  25                  30
Asn Asp Leu Thr Asp Pro Asn Met Leu Ala His Leu Leu Lys Tyr Asp
         35                  40                  45

Thr Thr Gln Gly Arg Phe Asp Gly Thr Val Glu Val Lys Asp Gly Gly
     50                  55                  60

Phe Glu Val Asn Gly Ser Phe Val Lys Val Ser Ala Glu Arg Glu Pro
 65                  70                  75                  80

Ala Asn Ile Asp Trp Ala Thr Asp Gly Val Asp Ile Val Leu Glu Ala
                 85                  90                  95

Thr Gly Phe Phe Ala Ser Lys Ala Ala Glu Gln His Ile His Ala
            100                 105                 110

Asn Gly Ala Lys Lys Val Val Ile Thr Ala Pro Gly Gly Asn Asp Val
        115                 120                 125

Lys Thr Val Val Tyr Asn Thr Asn His Asp Ile Leu Asp Gly Thr Glu
130                 135                 140

Thr Val Ile Ser Gly Ala Ser Cys Thr Thr Asn Cys Leu Ala Pro Met
145                 150                 155                 160

Ala Lys Ala Leu Gln Asp Asn Phe Gly Val Lys Gln Gly Leu Met Thr
                165                 170                 175

Thr Ile His Gly Tyr Thr Gly Asp Gln Met Val Leu Asp Gly Pro His
            180                 185                 190

Arg Gly Gly Asp Leu Arg Arg Ala Arg Ala Ala Ala Asn Ile Val
        195                 200                 205

Pro Asn Ser Thr Gly Ala Ala Lys Ala Ile Gly Leu Val Ile Pro Glu
    210                 215                 220

Leu Asn Gly Lys Leu Asp Gly Ala Ala Gln Arg Val Pro Val Pro Thr
225                 230                 235                 240

Gly Ser Val Thr Glu Leu Val Ala Val Leu Glu Lys Asp Thr Ser Val
                245                 250                 255

Glu Glu Ile Asn Ala Ala Met Lys Ala Ala Asn Asp Ser Tyr Gly
            260                 265                 270

Tyr Thr Glu Asp Ala Ile Val Ser Ser Asp Ile Val Gly Ile Ser Tyr
        275                 280                 285

Gly Ser Leu Phe Asp Ala Thr Gln Thr Lys Val Gln Thr Val Asp Gly
    290                 295                 300

Asn Gln Leu Val Lys Val Ser Trp Tyr Asp Asn Glu Met Ser Tyr
305                 310                 315                 320

Thr Ala Gln Leu Val Arg Thr Leu Glu Tyr Phe Ala Lys Ile Ala Lys
                325                 330                 335

<210> SEQ ID NO 21
<211> LENGTH: 1347
<212> TYPE: DNA
<213> ORGANISM: Artificial Sequence
<220> FEATURE:
<223> OTHER INFORMATION: Description of Artificial Sequence: primer Gap4
      chimeric GapC protein
<220> FEATURE:
<221> NAME/KEY: CDS
<222> LOCATION: (1)..(1347)

<400> SEQUENCE: 21 atg aaa aaa ata aca ggg att att tta ttg ctt ctt gca gtc att att      48
Met Lys Lys Ile Thr Gly Ile Ile Leu Leu Leu Leu Ala Val Ile Ile
  1               5                  10                  15 ctg tct gca tgc cag gca aac tac gga tcc ggt atg gta gtt aaa gtt     96
Leu Ser Ala Cys Gln Ala Asn Tyr Gly Ser Gly Met Val Val Lys Val
```

-continued

|  |  |  |  |  |  |  |  |  |  |  |  |  |  |  |  |
|---|---|---|---|---|---|---|---|---|---|---|---|---|---|---|---|
|  |  | 20 |  |  |  | 25 |  |  |  | 30 |  |  |  |  |  |

```
ggt att aac ggt ttc ggt cgt atc gga cgt ctt gca ttc cgt cgt att      144
Gly Ile Asn Gly Phe Gly Arg Ile Gly Arg Leu Ala Phe Arg Arg Ile
         35                  40                  45 caa aat gtt gaa ggt gtt gaa gta act cgt atc aac gac ctt aca gat      192
Gln Asn Val Glu Gly Val Glu Val Thr Arg Ile Asn Asp Leu Thr Asp
 50                  55                  60 cca aac atg ctt gca cac ttg ttg aaa tac gat aca act caa gga cgt      240
Pro Asn Met Leu Ala His Leu Leu Lys Tyr Asp Thr Thr Gln Gly Arg
 65                  70                  75                  80 ttt gac gga act gtt gaa gtt aaa gaa ggt gga ttt gaa gta aac gga      288
Phe Asp Gly Thr Val Glu Val Lys Glu Gly Gly Phe Glu Val Asn Gly
                 85                  90                  95 aac ttc atc aaa gtt tct gct gaa cgt gat cca gaa aac atc gac tgg      336
Asn Phe Ile Lys Val Ser Ala Glu Arg Asp Pro Glu Asn Ile Asp Trp
            100                 105                 110 gca act gac ggt gtt gaa atc gtt ctg gaa gca ctc gag ggt act gta      384
Ala Thr Asp Gly Val Glu Ile Val Leu Glu Ala Leu Glu Gly Thr Val
        115                 120                 125 gaa gtt aaa gat ggt gga ttt gac gtt aac gga aaa ttc att aaa gtt      432
Glu Val Lys Asp Gly Gly Phe Asp Val Asn Gly Lys Phe Ile Lys Val
    130                 135                 140 tct gct gaa aaa gat cca gaa caa att gac tgg gca act gac ggt gtt      480
Ser Ala Glu Lys Asp Pro Glu Gln Ile Asp Trp Ala Thr Asp Gly Val
145                 150                 155                 160 gaa atc gtt ctt gaa atc gat ggt act gtt gaa gtt aaa gaa ggt gga      528
Glu Ile Val Leu Glu Ile Asp Gly Thr Val Glu Val Lys Glu Gly Gly
                165                 170                 175 ttc gaa gtt aac ggt caa ttt gtt aaa gtt tct gct gaa cgc gaa cca      576
Phe Glu Val Asn Gly Gln Phe Val Lys Val Ser Ala Glu Arg Glu Pro
            180                 185                 190 gca aac att gac tgg gct act gat ggc gta gaa atc gtt ctt gaa gca      624
Ala Asn Ile Asp Trp Ala Thr Asp Gly Val Glu Ile Val Leu Glu Ala
        195                 200                 205 act agt ttc ttt gct aaa aaa gaa gct gct gaa aaa cac tta cat gct      672
Thr Ser Phe Phe Ala Lys Lys Glu Ala Ala Glu Lys His Leu His Ala
    210                 215                 220 aac ggt gct aaa aaa gtt gtt atc aca gct cct ggt gga aac gac gtt      720
Asn Gly Ala Lys Lys Val Val Ile Thr Ala Pro Gly Gly Asn Asp Val
225                 230                 235                 240 aaa aca gtt gtt ttc aac act aac cac gac att ctt gac ggt act gaa      768
Lys Thr Val Val Phe Asn Thr Asn His Asp Ile Leu Asp Gly Thr Glu
                245                 250                 255 aca gtt atc tca ggt gct tca tgt act aca aac tgt tta gct cct atg      816
Thr Val Ile Ser Gly Ala Ser Cys Thr Thr Asn Cys Leu Ala Pro Met
            260                 265                 270 gct aaa gct ctt cac gat gca ttt ggt atc caa aaa ggt ctt atg act      864
Ala Lys Ala Leu His Asp Ala Phe Gly Ile Gln Lys Gly Leu Met Thr
        275                 280                 285 aca atc cac gct tat act ggt gac caa atg atc ctt gac gga cca cac      912
Thr Ile His Ala Tyr Thr Gly Asp Gln Met Ile Leu Asp Gly Pro His
    290                 295                 300 cgt ggt ggt gac ctt cgt cgt gct cgt gct ggt gct gca aac att gtt      960
Arg Gly Gly Asp Leu Arg Arg Ala Arg Ala Gly Ala Ala Asn Ile Val
305                 310                 315                 320 cct aac tca act ggt gct gct aaa gct atc ggt ctt gtt atc cca gaa     1008
Pro Asn Ser Thr Gly Ala Ala Lys Ala Ile Gly Leu Val Ile Pro Glu
                325                 330                 335 ttg aat ggt aaa ctt gat ggt gct gca caa cgt gtt cct gtt cca act     1056
Leu Asn Gly Lys Leu Asp Gly Ala Ala Gln Arg Val Pro Val Pro Thr
```

-continued

| | | | | | | | | | | | | |
|---|---|---|---|---|---|---|---|---|---|---|---|---|
| Leu | Asn | Gly | Lys | Leu | Asp | Gly | Ala | Ala | Gln | Arg | Val | Pro | Val | Pro | Thr |
| | | | 340 | | | | | 345 | | | | 350 | | | |

| gga | tca | gta | act | gag | ttg | gtt | gta | act | ctt | gat | aaa | aac | gtt | tct | gtt | 1104 |
|---|---|---|---|---|---|---|---|---|---|---|---|---|---|---|---|---|
| Gly | Ser | Val | Thr | Glu | Leu | Val | Val | Thr | Leu | Asp | Lys | Asn | Val | Ser | Val | |
| | | 355 | | | | | 360 | | | | | 365 | | | | |

| gac | gaa | atc | aac | gct | gct | atg | aaa | gct | gct | tca | aac | gac | agt | ttc | ggt | 1152 |
|---|---|---|---|---|---|---|---|---|---|---|---|---|---|---|---|---|
| Asp | Glu | Ile | Asn | Ala | Ala | Met | Lys | Ala | Ala | Ser | Asn | Asp | Ser | Phe | Gly | |
| 370 | | | | | 375 | | | | | 380 | | | | | | |

| tac | act | gaa | gat | cca | att | gtt | tct | tca | gat | atc | gta | ggc | gtg | tca | tac | 1200 |
|---|---|---|---|---|---|---|---|---|---|---|---|---|---|---|---|---|
| Tyr | Thr | Glu | Asp | Pro | Ile | Val | Ser | Ser | Asp | Ile | Val | Gly | Val | Ser | Tyr | |
| 385 | | | | | 390 | | | | | 395 | | | | | 400 | |

| ggt | tca | ttg | ttt | gac | gca | act | caa | act | aaa | gtt | atg | gaa | gtt | gac | gga | 1248 |
|---|---|---|---|---|---|---|---|---|---|---|---|---|---|---|---|---|
| Gly | Ser | Leu | Phe | Asp | Ala | Thr | Gln | Thr | Lys | Val | Met | Glu | Val | Asp | Gly | |
| | | | 405 | | | | | 410 | | | | | 415 | | | |

| tca | caa | ttg | gtt | aaa | gtt | gta | tca | tgg | tat | gac | aat | gaa | atg | tct | tac | 1296 |
|---|---|---|---|---|---|---|---|---|---|---|---|---|---|---|---|---|
| Ser | Gln | Leu | Val | Lys | Val | Val | Ser | Trp | Tyr | Asp | Asn | Glu | Met | Ser | Tyr | |
| | | | 420 | | | | | 425 | | | | | 430 | | | |

| act | gct | caa | ctt | gtt | cgt | aca | ctt | gag | tat | ttt | gca | aaa | atc | gct | aaa | 1344 |
|---|---|---|---|---|---|---|---|---|---|---|---|---|---|---|---|---|
| Thr | Ala | Gln | Leu | Val | Arg | Thr | Leu | Glu | Tyr | Phe | Ala | Lys | Ile | Ala | Lys | |
| | | 435 | | | | | 440 | | | | | 445 | | | | |

| taa | 1347 |
|---|---|

<210> SEQ ID NO 22
<211> LENGTH: 448
<212> TYPE: PRT
<213> ORGANISM: Artificial Sequence
<220> FEATURE:
<223> OTHER INFORMATION: Description of Artificial Sequence: GapC
   multiple epitope fusion protein

<400> SEQUENCE: 22

| Met | Lys | Lys | Ile | Thr | Gly | Ile | Ile | Leu | Leu | Leu | Ala | Val | Ile | Ile |
|---|---|---|---|---|---|---|---|---|---|---|---|---|---|---|
| 1 | | | | 5 | | | | | 10 | | | | | 15 |

| Leu | Ser | Ala | Cys | Gln | Ala | Asn | Tyr | Gly | Ser | Gly | Met | Val | Val | Lys | Val |
|---|---|---|---|---|---|---|---|---|---|---|---|---|---|---|---|
| | | | 20 | | | | | 25 | | | | | 30 | | |

| Gly | Ile | Asn | Gly | Phe | Gly | Arg | Ile | Gly | Arg | Leu | Ala | Phe | Arg | Arg | Ile |
|---|---|---|---|---|---|---|---|---|---|---|---|---|---|---|---|
| | | 35 | | | | | 40 | | | | | 45 | | | |

| Gln | Asn | Val | Glu | Gly | Val | Glu | Val | Thr | Arg | Ile | Asn | Asp | Leu | Thr | Asp |
|---|---|---|---|---|---|---|---|---|---|---|---|---|---|---|---|
| | 50 | | | | | 55 | | | | | 60 | | | | |

| Pro | Asn | Met | Leu | Ala | His | Leu | Leu | Lys | Tyr | Asp | Thr | Thr | Gln | Gly | Arg |
|---|---|---|---|---|---|---|---|---|---|---|---|---|---|---|---|
| 65 | | | | | 70 | | | | | 75 | | | | | 80 |

| Phe | Asp | Gly | Thr | Val | Glu | Val | Lys | Glu | Gly | Gly | Phe | Glu | Val | Asn | Gly |
|---|---|---|---|---|---|---|---|---|---|---|---|---|---|---|---|
| | | | | 85 | | | | | 90 | | | | | 95 | |

| Asn | Phe | Ile | Lys | Val | Ser | Ala | Glu | Arg | Asp | Pro | Glu | Asn | Ile | Asp | Trp |
|---|---|---|---|---|---|---|---|---|---|---|---|---|---|---|---|
| | | | 100 | | | | | 105 | | | | | 110 | | |

| Ala | Thr | Asp | Gly | Val | Glu | Ile | Val | Leu | Glu | Ala | Leu | Glu | Gly | Thr | Val |
|---|---|---|---|---|---|---|---|---|---|---|---|---|---|---|---|
| | | 115 | | | | | 120 | | | | | 125 | | | |

| Glu | Val | Lys | Asp | Gly | Gly | Phe | Asp | Val | Asn | Gly | Lys | Phe | Ile | Lys | Val |
|---|---|---|---|---|---|---|---|---|---|---|---|---|---|---|---|
| | 130 | | | | | 135 | | | | | 140 | | | | |

| Ser | Ala | Glu | Lys | Asp | Pro | Glu | Gln | Ile | Asp | Trp | Ala | Thr | Asp | Gly | Val |
|---|---|---|---|---|---|---|---|---|---|---|---|---|---|---|---|
| 145 | | | | | 150 | | | | | 155 | | | | | 160 |

| Glu | Ile | Val | Leu | Glu | Ile | Asp | Gly | Thr | Val | Glu | Val | Lys | Glu | Gly | Gly |
|---|---|---|---|---|---|---|---|---|---|---|---|---|---|---|---|
| | | | | 165 | | | | | 170 | | | | | 175 | |

| Phe | Glu | Val | Asn | Gly | Gln | Phe | Val | Lys | Val | Ser | Ala | Glu | Arg | Glu | Pro |
|---|---|---|---|---|---|---|---|---|---|---|---|---|---|---|---|
| | | | 180 | | | | | 185 | | | | | 190 | | |

| Ala | Asn | Ile | Asp | Trp | Ala | Thr | Asp | Gly | Val | Glu | Ile | Val | Leu | Glu | Ala |
|---|---|---|---|---|---|---|---|---|---|---|---|---|---|---|---|
| | | 195 | | | | | 200 | | | | | 205 | | | |

-continued

```
Thr Ser Phe Phe Ala Lys Lys Glu Ala Ala Glu Lys His Leu His Ala
    210             215             220
Asn Gly Ala Lys Lys Val Val Ile Thr Ala Pro Gly Gly Asn Asp Val
225             230             235             240
Lys Thr Val Val Phe Asn Thr Asn His Asp Ile Leu Asp Gly Thr Glu
                245             250             255
Thr Val Ile Ser Gly Ala Ser Cys Thr Thr Asn Cys Leu Ala Pro Met
            260             265             270
Ala Lys Ala Leu His Asp Ala Phe Gly Ile Gln Lys Gly Leu Met Thr
        275             280             285
Thr Ile His Ala Tyr Thr Gly Asp Gln Met Ile Leu Asp Gly Pro His
    290             295             300
Arg Gly Gly Asp Leu Arg Arg Ala Arg Ala Gly Ala Ala Asn Ile Val
305             310             315             320
Pro Asn Ser Thr Gly Ala Ala Lys Ala Ile Gly Leu Val Ile Pro Glu
                325             330             335
Leu Asn Gly Lys Leu Asp Gly Ala Ala Gln Arg Val Pro Val Pro Thr
            340             345             350
Gly Ser Val Thr Glu Leu Val Val Thr Leu Asp Lys Asn Val Ser Val
        355             360             365
Asp Glu Ile Asn Ala Ala Met Lys Ala Ala Ser Asn Asp Ser Phe Gly
    370             375             380
Tyr Thr Glu Asp Pro Ile Val Ser Ser Asp Ile Val Gly Val Ser Tyr
385             390             395             400
Gly Ser Leu Phe Asp Ala Thr Gln Thr Lys Val Met Glu Val Asp Gly
                405             410             415
Ser Gln Leu Val Lys Val Val Ser Trp Tyr Asp Asn Glu Met Ser Tyr
            420             425             430
Thr Ala Gln Leu Val Arg Thr Leu Glu Tyr Phe Ala Lys Ile Ala Lys
        435             440             445
```

IMMUNIZATION OF DAIRY CATTLE WITH CHIMERIC GAPC PROTEIN AGAINST *STREPTOCOCCUS* INFECTION

CROSS-REFERENCE TO RELATED APPLICATION

This application is a continuation of U.S. patent application Ser. No. 10/650,369, filed Aug. 27, 2003, now U.S. Pat. No. 6,875,853, which is a continuation of U.S. patent application Ser. No. 09/878,766, filed Jun. 11, 2001, now U.S. Pat. No. 6,660,270, from which applications priority is claimed under 35 USC §120. U.S. patent application Ser. No. 09/878,766 claims the benefit under 35 USC §119(e)(1) of U.S. Provisional Application No. 60/211,247, filed Jun. 12, 2000. The foregoing applications are incorporated herein by reference in their entireties.

TECHNICAL FIELD

The present invention relates generally to bacterial antigens and genes encoding the same. More particularly, the present invention pertains to the construction of a chimeric plasmin binding protein gene comprising the entire *S. dysgalactiae* gapC coding sequence as well as coding sequences for unique regions from several *Streptococcus* bacteria species, and the use of the same in vaccine compositions.

BACKGROUND

Mastitis, an infection of the mammary gland usually caused by bacteria or fungus, results in major economic losses to the dairy industry yearly. Among the bacterial species most commonly associated with mastitis are various species of the genus *Streptococcus*, including *S. aureus, S. uberis*, (untypeable), *S. agalactiae* (Lancefield group B), *S. dysgalactiae* (Lancefield group C), *S. zooepidemicus*, and the Lancefield groups D, G., L and N *streptococci*. Some of those species are contagions (e.g. *S. agalactiae*), while others are considered environmental pathogens (e.g. *S. dysgalactiae* and *S. uberis*). The environmental pathogen *S. uberis* is responsible for about 20% of all clinical cases of mastitis (Bramley, A. J. and Dodd, F. H. (1984) *J. Dairy Res.* 51:481-512; Bramley, A. J. (1987) *Animal Health Nutrition* 42:12-16; Watts, J. L. (1988) *J. Dairy Sci.* 71:1616-1624); it is the predominant organism isolated from mammary glands during the non-lactating period (Bramley, A. J. (1984) *Br. Vet. J.* 140:328-335; Bramley and Dodd (1984) *J. Dairy Res.* 51:481-512; Oliver, S. P. (1988) *Am. J. Vet. Res.* 49:1789-1793).

Mastitis resulting from infection with *S. uberis* is commonly subclinical, characterized by apparently normal milk with an increase in somatic cell counts due to the influx of leukocytes. The chemical composition of milk is changed due to suppression of secretion with the transfer of sodium chloride and bicarbonate from blood to milk, causing a shift of pH to a more alkaline level. *S. uberis* mastitis may also take the form of an acute clinical condition, with obvious signs of disease such as clots or discoloration of the milk and swelling or hardness of the mammary gland. Some cases of the clinical disease can be severe and pyrexia may be present. For a review of the clinical manifestations of *S. uberis* mastitis, see, Bramley (1991) Mastitis: physiology or pathology. p. 3-9. In C. Burvenich, G. Vandeputte-van Messom, and A. W. Hill (ed.), *New insights into the pathogenesis of mastitis*. Rijksuniversiteit Gent, Belgium; and Schalm et al. (1971) The mastitis complex-A brief summary. p. 1-3. In *Bovine Mastitis*. Lea & Febiger, Philadelphia Conventional antibacterial control methods such as teat dipping and antibiotic therapy are effective in the control of many types of contagious mastitis, but the environmental organisms typically found in all dairy barns are often resistant to such measures. Vaccination is therefore an attractive strategy to prevent infections of the mammary glands, and has been shown to be beneficial in the case of some contagious mastitis pathogens.

The literature is limited regarding vaccination studies with *S. dysgalactiae* and *S. uberis*, and variable results have been observed. In some cases, immunization has resulted in increased sensitivity to the specific organism and in other cases strain-specific protection has been obtained.

For example, previous studies have shown that primary infection with *S. uberis* can considerably reduce the rate of infection following a second challenge with the same strain (Hill, A. W. (1988) *Res. Vet. Sci.* 44:386-387). Local vaccination with killed *S. uberis* protects the bovine mammary gland against intramammary challenge with the homologous strain (Finch et al. (1994) *Infect. Immun.* 62:3599-3603). Similarly, subcutaneous vaccination with live *S. uberis* has been shown to cause a dramatic modification of the pathogenesis of mastitis with the same strain (Hill et al. (1994) *FEMS Immunol. Med. Microbiol.* 8:109-118). Animals vaccinated in this way shed fewer bacteria in their milk and many quarters remain free of infection.

Nonetheless, vaccination with live or attenuated bacteria can pose risks to the recipient. Further, it is clear that conventional killed vaccines are in general largely ineffective against *S. uberis* and *S. agalactiae*, either due to lack of protective antigens on in vitro-grown cells or masking of these antigens by molecular mimicry.

The current lack of existing mastitis vaccines against *S. agalactiae* or the contagious *streptococcus* strains is due at least in part to a lack of knowledge regarding the virulence determinants and protective antigens produced by those organisms which are involved in invasion and protection of the mammary gland (Collins et al. (1988) *J. Dairy Res.* 55:25-32; Leigh et al. (1990) *Res. Vet. Sci.* 49: 85-87; Marshall et al. (1986) *J. Dairy Res.* 53: 507-514).

*S. dysgalactiae* is known to bind several extracellular and plasma-derived proteins such as fibronectin, fibrinogen, collagen, alpha-II-macroglobulin, IgG, albumin and other compounds. The organism also produces hyaluronidase and fibrinolysin and is capable of adhering to and invading bovine mammary epithelial cells. However, the exact roles of the bacterial components responsible for these phenotypes in pathogenesis is not known.

Similarly, the pathogenesis of *S. uberis* infection is poorly understood. Furthermore, the influence of *S. uberis* virulence factors on host defense mechanisms and mammary gland physiology is not well defined. Known virulence factors associated with *S. uberis* include a hyaluronic acid capsule (Hill, A. W. (1988) *Res. Vet. Sci.* 45:400-404), hyaluronidase (Schaufuss et al. (1989) *Zentralbl. Bakteriol. Ser. A* 271:46-53), R-like protein (Groschup, M. H. and Timoney, J. F. (1993) *Res. Vet. Sci.* 54:124-126), and a cohemolysin, the CAMP factor, also known as *UBERIS* factor (Skalka, B. and Smola, J. (1981) *Zentralbl. Bakteriol. Ser. A* 249:190-194), R-like protein, plasminogen activator and CAMP factor. However, very little is known of their roles in pathogenicity.

The use of virulence determinants from *Streptococcus* as immunogenic agents has been proposed. For example, the CAMP factor of *S. uberis* has been shown to protect vertebrate subjects from infection by that organism (Jiang, U.S. Pat. No. 5,863,543).

They antigen of the group B *Streptococci* strain A909 (ATCC No. 27591) is a component of the c protein marker complex, which additionally comprises an α and β subunit (Boyle, U.S. Pat. No. 5,721,339). Subsets of serotype Ia, II, and virtually all serotype Ib cells of group B *streptococci*, have been reported to express components of the c protein. Use of the γ subunit as an immunogenic agent against infections by Lancefield Group B *Streptococcus* infection has been proposed. However, its use to prevent or treat bacterial infections in animals, including mastitis in cattle, has not been studied.

A GapC plasmin binding protein from a strain of Group A *Streptococcus* has previously been identified and characterized, and its use in thrombolytic therapies has been described (Boyle, et al., U.S. Pat. No. 5,237,050; Boyle, et al., U.S. Pat. No. 5,328,996). However, the use of GapC as an immungenic agent to treat or prevent mastitis was neither described nor suggested.

The group A streptococcal M protein is considered to be one of the major virulence factors of this organism by virtue of its ability to impede attack by human phagocytes (Lancefield, R. C. (1962) *J. Immunol.* 89:307-313). The bacteria persist in the infected tissue until antibodies are produced against the M molecule. Type-specific antibodies to the M protein are able to reverse the antiphagocytic effect of the molecule and allow efficient clearance of the invading organism.

M proteins are one of the key virulence factors of *Streptococcus pyogenes*, due to their involvement in mediating resistance to phagocytosis (Kehoe, M. A. (1991) *Vaccine* 9:797-806) and their ability to induce potentially harmful host immune responses via their superantigenicity and their capacity to induce host-cross-reactive antibody responses (Bisno, A. L. (1991) *New Engl. J. Med.* 325:783-793; Froude et al. (1989) *Curr. Top. Microbiol Immunol.* 145:5-26; Stollerman, G. H. (1991) *Clin. Immunol. Immunopathol.* 61:131-142).

However, obstacles exist to using intact M proteins as vaccines. The protein's opsonic epitopes are extremely type-specific, resulting in narrow, type-specific protection. Further, some M proteins appear to contain epitopes that cross react with tissues of the immunized subject, causing a harmful autoimmune response (See e.g., Dale, J. L. and Beached, G. H. (1982) *J. Exp. Med* 156:1165-1176; Dale, J. L. and Beached, G. H. (1985) *J. Exp. Med.* 161:113-122; Baird, R. W., Bronze, M. S., Drabs, W., Hill, H. R., Veasey, L. G. and Dale, J. L. (1991) *J. Immun.* 146:3132-3137; Bronze, M. S. and Dale, J. L. (1993) *J. Immun* 151:2820-2828; Cunningham, M. W. and Russell, S. M. (1983) *Infect. Immun.* 42:531-538).

An octavalent M protein vaccine has been constructed and was tested for protective immunogenicity against multiple serotypes of group A *streptococci* infection in rabbits. However, the immune response obtained was serotype-specific, conferring protection only against those bacterial strains exhibiting the M protein epitopes present in the chimeric protein (Dale, J. B., Simmons, M., Chiang, E. C., and Chiang, E. Y. (1996) *Vaccine* 14:944-948).

Chimeric proteins containing three different fibronectin binding domains (FNBDs) derived from fibronectin binding proteins of *S. dysgalactiae* and *Staphylococcus aureus* have been expressed on the surface of *Staph. carnosus* cells. In the case of one of these proteins, intranasal immunizations with live recombinant *Staph. carnosus* cells expressing the chimeric protein on their surface resulted in an improved antibody response to a model immunogen present within the chimeric surface protein.

A chimeric Protein G molecule (a type III Fc binding protein specific for the Fc region of all subclasses of IgG antibody molecules) is known, but its use as an immunogenic agent has not been described or suggested (Bjorck, et al. (1992) U.S. Pat. No. 5,108,894).

Until now, the protective capability of GapC multiple epitope fusion proteins has not been studied.

SUMMARY OF THE INVENTION

Accordingly, the present invention provides GapC multiple epitope fusion proteins and polynucleotides encoding the same. In one embodiment, the invention is directed to a multiple epitope fusion polypeptide comprising the general structural formula (I):

$$(A)_x\text{---}(B)_y\text{---}(C)_z \qquad (I)$$

wherein
(I) is a linear amino acid sequence;
B comprises an amino acid sequence containing at least five amino acids which amino acids correspond to an antigenic determinant of a GapC protein;
A and C each comprise an amino acid sequence that is
  (i) different from B,
  (ii) different from the other, and
  (iii) an amino acid sequence containing at least five amino acids, which amino acid sequence corresponds to an antigenic determinant of a GapC protein wherein said antigenic determinant is not adjacent to B in nature;
y is an integer of 1 or more; and
x and z are each independently integers wherein x+z is 1 or more.

In certain embodiments, the multiple epitope fusion polypeptide further comprises a signal sequence and/or a transmembrane sequence. Further, A, B, and/or C of the multiple epitope fusion polypeptide may linked by one or more spacer sequences, wherein the spacers
  (i) are amino acid sequences of from 1 to 1,000 amino acids, inclusive;
  (ii) can be the same or different as A, B, or C; and
  (iii) can be the same or different as each other.

In certain embodiments, A, B, and C each comprise epitopes from one or more species of bacteria, such as from one or more bacterial species of the genus *Streptococcus*, including but not limited to one or more bacterial species selected from the group consisting of *Streptococcus dysgalactiae, Streptococcus agalactiae, Streptococcus uberis, Streptococcus parauberis,* and *Streptococcus iniae*.

In yet another embodiment, A, B, and C each comprise amino acid sequences selected from the group consisting of
  (a) the amino acid sequence shown at about amino acid positions 61 to 81, inclusive, of FIGS. 1 through 5, or any amino acid sequence having at least about 80% identity thereto;
  (b) the amino acid sequences shown at about amino acid positions 102 to 112, inclusive, of FIGS. 1 through 5, or any amino acid sequence having at least about 80% identity thereto;
  (c) the amino acid sequences shown at about amino acid positions 165 to 172, inclusive, of FIGS. 1 through 5, or any amino acid sequence having at least about 80% identity thereto;

(d) the amino acid sequences shown at about amino acid positions 248 to 271, inclusive, of Figures through 5, or any amino acid sequence having at least about 80% identity thereto; and (e) the amino acid sequences shown at about amino acid positions 286 to 305, inclusive, of FIGS. 1 through 5, or any amino acid sequence having at least about 80% identity thereto.

In another embodiment, the multiple epitope fusion polypeptide comprises the amino acid sequence depicted in FIG. 6 (SEQ ID NO:22).

In yet further embodiments, the invention is directed to polynucleotide sequences encoding the multiple epitope fusion polypeptide sequence described above or compliments thereof, as well as recombinant vectors comprising the polynucleotide, host cells comprising the recombinant vectors and methods of recombinantly producing the polypeptides.

In another embodiment, the invention is directed to a vaccine composition comprising a pharmaceutically acceptable vehicle and a multiple epitope fusion polypeptide as described above. In certain embodiments, the vaccine compositions comprise an adjuvant.

In still a further embodiment, the invention is directed to a method of producing a vaccine composition comprising the steps of (1) providing the multiple epitope fusion polypeptide; and (2) combining the polypeptide with a pharmaceutically acceptable vehicle.

In another embodiment, the invention is directed to a method of treating or preventing a bacterial infection in a vertebrate subject comprising administering to the subject a therapeutically effective amount of a vaccine composition as described above.

In certain embodiments, the bacterial infection is a streptococcal infection. Further, the bacterial infection may cause mastitis.

In yet another embodiment, the invention is directed to a method of treating or preventing a bacterial infection in a vertebrate subject comprising administering to the subject a therapeutically effective amount of a polynucleotide as described herein.

In certain embodiments, the bacterial infection is a streptococcal infection. Further, the bacterial infection may cause mastitis.

In further embodiments, the invention is directed to antibodies directed against the above multiple epitope fusion polypeptides. The antibodies may be polyclonal or monoclonal.

In another embodiment, the invention is directed to a method of detecting *Streptococcus* antibodies in a biological sample, comprising:

(a) reacting said biological sample with a multiple epitope fusion polypeptide under conditions which allow said *Streptococcus* antibodies, when present in the biological sample, to bind to said sequence to form an antibody/antigen complex; and (b) detecting the presence or absence of said complex, and thereby detecting the presence or absence of *Streptococcus* antibodies in said sample.

In still a further embodiment, the invention is directed to an immunodiagnostic test kit for detecting *Streptococcus* infection. The test kit comprises a multiple epitope fusion polypeptide as described herein and instructions for conducting the immunodiagnostic test.

These and other embodiments of the subject invention will readily occur to those of skill in the art in view of the disclosure herein.

BRIEF DESCRIPTION OF THE FIGURES

FIGS. 1A-1B depict the isolated nucleotide sequence and deduced amino acid sequence of the gapC gene for *S. dysgalactiae* (SEQ ID NO:11 and SEQ ID NO:12). In the figure, the asterisk represents a stop codon, and the underlined regions represent nucleotide sequences complementary to the primers used to isolate the genes from the bacterial chromosomes.

FIGS. 2A-2B depict the isolated nucleotide sequence and deduced amino acid sequence of the gapC gene for *S. agalactiae* (SEQ ID NO:13 and SEQ ID NO:14). In the figure, the asterisk represents a stop codon, and the underlined regions represent nucleotide sequences complementary to the primers used to isolate the genes from the bacterial chromosomes.

FIGS. 3A-3B depict the isolated nucleotide sequence and deduced amino acid sequence of the gapC gene for *S. uberis* (SEQ ID NO:15) and SEQ ID NO:16). In the figure, the asterisk represents a stop codon, and the underlined regions represent nucleotide sequences complementary to the primers used to isolate the genes from the bacterial chromosomes.

FIGS. 4A-4B depict the isolated nucleotide sequence and deduced amino acid sequence of the gapC gene for *S. parauberis* (SEQ ID NO:17 and SEQ ID NO:18). In the figure, the asterisk represents a stop codon, and the underlined regions represent nucleotide sequences complementary to the primers used to isolate the genes from the bacterial chromosomes.

FIGS. 5A-5B depict the isolated nucleotide sequence and deduced amino acid sequence of the gapC gene for *S. iniae* (SEQ ID NO:19 and SEQ ID NO:20). In the figure, the asterisk represents a stop codon, and the underlined regions represent nucleotide sequences complementary to the primers used to isolate the genes from the bacterial chromosomes.

FIG. 6 depicts the nucleotide sequence (SEQ ID NO:21) and deduced amino acid sequence (SEQ ID NO:22) of the GapC multiple epitope fusion protein of the present invention.

FIGS. 7A-7E show a DNA alignment chart created by PileUp and displayed by Pretty software (a component of the GCG Wisconsin Package, version 10, provided by the SeqWeb sequence analysis package, version 1.1, of the Canadian Bioinformatics Resource). The figure depicts the isolated nucleotide sequences of the gapC genes from *S. dysgalactiae* (DysGapC, Check 9344) (SEQ ID NO:11); *S. agalactiae* (AgalGapC. Check 2895) (SEQ ID NO:13); *S. uberis* (UberGapC, Check 5966) (SEQ ID NO:15); *S. parauberis* (PUberGapC, Check 9672) (SEQ ID NO:17); and *S. iniae* (SiniGapC, Check 990) (SEQ ID NO:19). The previously known sequences of *S. equisimilis* (SeqGapC, Check 5841 ) (SEQ ID NO:25), *S. pyogenes* (SpyGapC, Check 4037) (SEQ ID NO:23), and a bovine GAPDH protein (BovGapC, check 5059) (SEQ ID NO:27) are also included. The length and weight parameters were the same for all sequences (1018 and 1.00, respectively). The parameters used in the DNA sequence comparison were as follows: Plurality—2.00; Threshold—1; AveWeight—1.00; AveMatch—1.00; AvMisMatch—0.00; Symbol comparison table—pileupdna.cmp; CompCheck—6876; GapWeight—5; GapLengthWeight—1; PileUp MSF—1018; Type—N;

Check—3804. In the figure, dashes represent identical nucleotides; dots represent gaps introduced by the software used to generate the alignment chart, and tildes represent regions not included in the overall alignment due to differences in the length of the gene sequences.

FIGS. 8A-8C show an amino acid sequence alignment chart created by PileUp and displayed by Pretty (as above) that depicts the alignment of PolyGap4 (SEQ ID NO:22), the multiple epitope fusion polypeptide of the present invention, with the deduced amino acid sequences of the native GapC proteins isolated from S. dysgalactiae (DysGape, Check 6731) (SEQ ID NO:12), S. agalactiae (AgalGapC, Check 1229) (SEQ ID NO:14), S. uberis (UberGapC, Check 8229) (SEQ ID NO:16), S. parauberis (PUberGapC, Check 8889) (SEQ IID NO:18), and S. iniae (JniaeGapC, check 8785) (SEQ ID NO:20). The previously known sequences of S. equisimilis (SeqGapC, Check 8252) (SEQ ID NO:26), S. pyogenes (SpyGapC, Check 6626) (SEQ ID NO:24) and a bovine GAPDH protein (BovGapC, Check 8479) (SEQ ID NO:28) are also included. In the figure, dashes represent identical amino acid residues; dots represent gaps introduced by the PileUp software, and tildes represent regions not included in the overall alignment due to differences in the length of the gene sequences.

Figure 9:
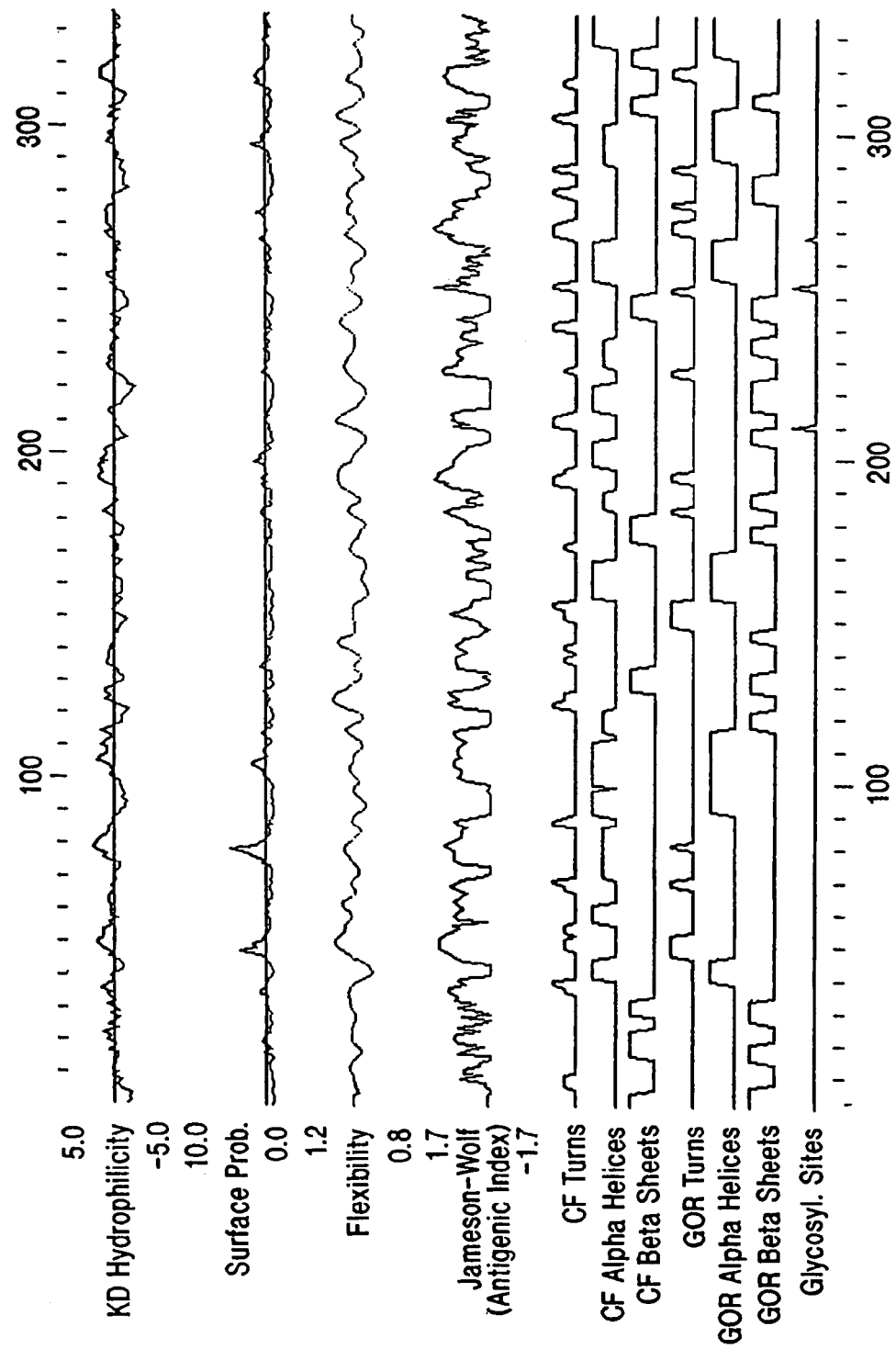

FIG. 9 shows a Kyte-Doolittle hydropathy plot, averaged over a window of 7, an Emini surface probability plot, a Karplus-Schulz chain flexibility plot, a Jameson-Wolf antigenic index plot, and both Chou-Fasman and Garnier-Osguthorpe-Robson secondary structure plots for the GapC protein isolated from S. dysgal.

Figure 10:
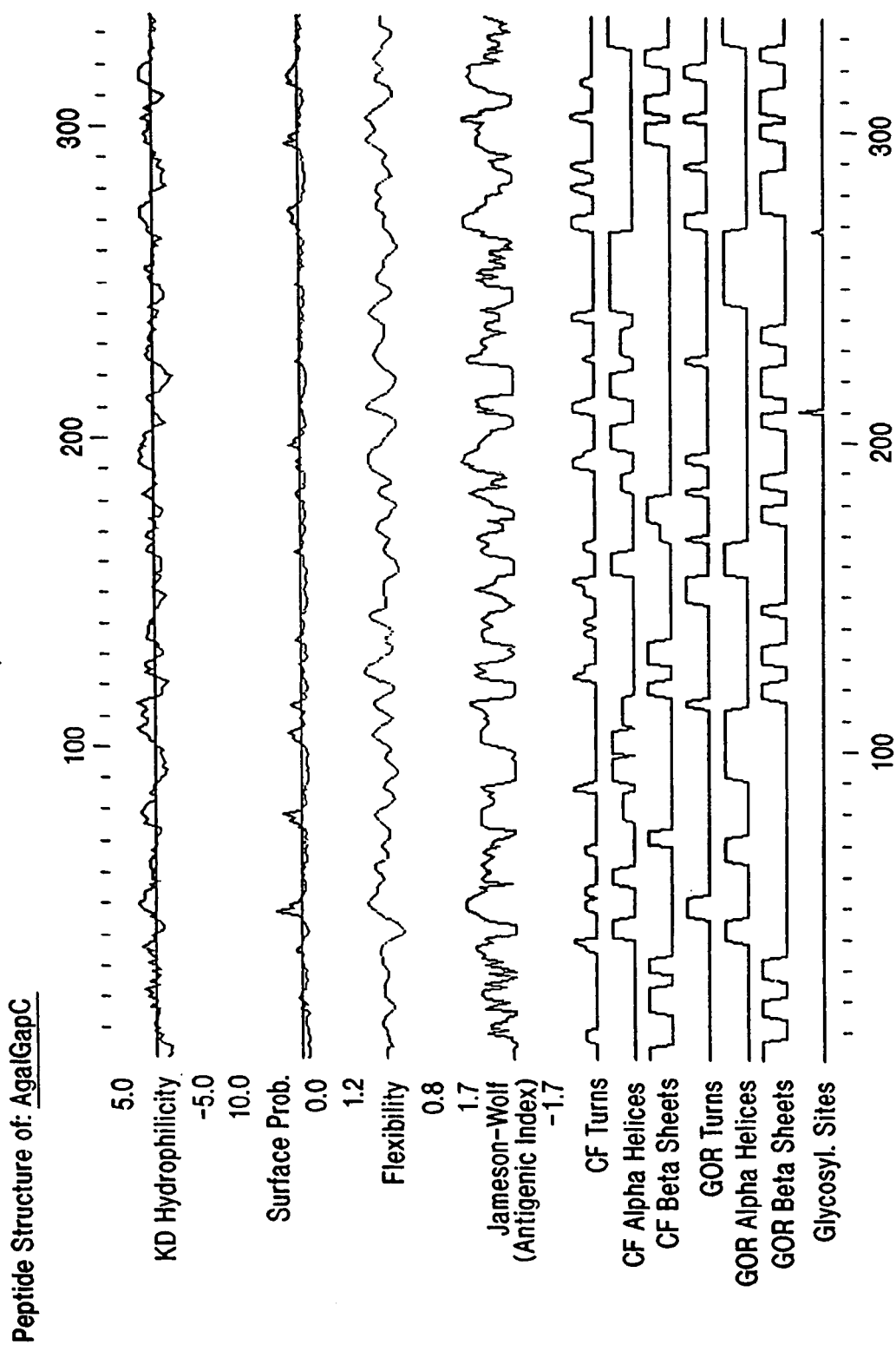
Figure 11:
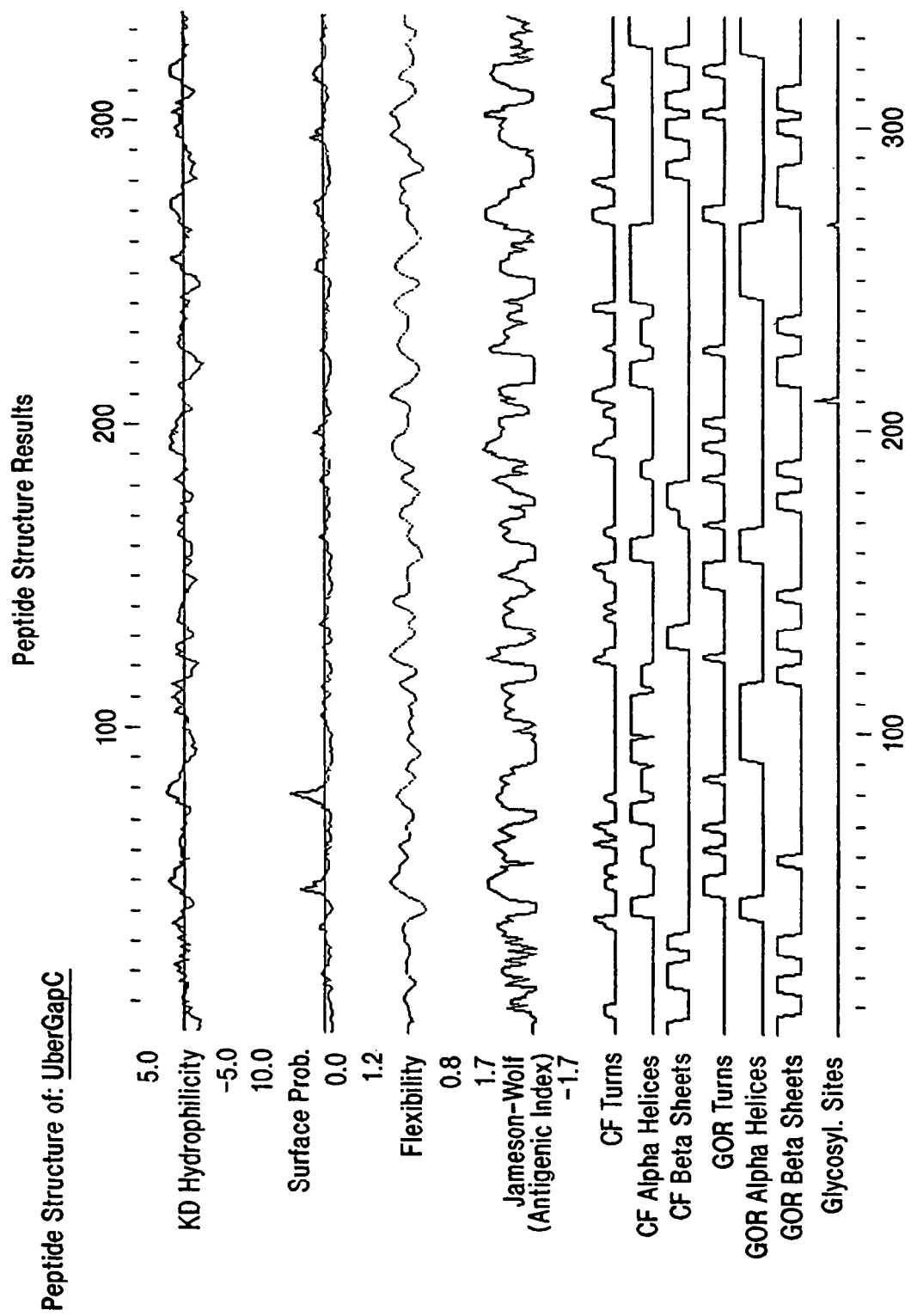

FIG. 10 shows a Kyte-Doolittle hydropathy plot, averaged over a window of 7, an Emini surface probability plot, a Karplus-Schulz chain flexibility plot, a Jameson-Wolf antigenic index plot, and both Chou-Fasman and Garnier-Osguthorpe-Robson secondary structure plots for the GapC protein isolated from S. agal FIG. 11 shows a Kyte-Doolittle hydropathy plot, averaged over a window of 7, an Emini surface probability plot, a Karplus-Schulz chain flexibility plot, a Jameson-Wolf antigenic index plot, and both Chou-Fasman and Garnier-Osguthorpe-Robson secondary structure plots for the GapC protein isolated from S. uberis.

Figure 12:
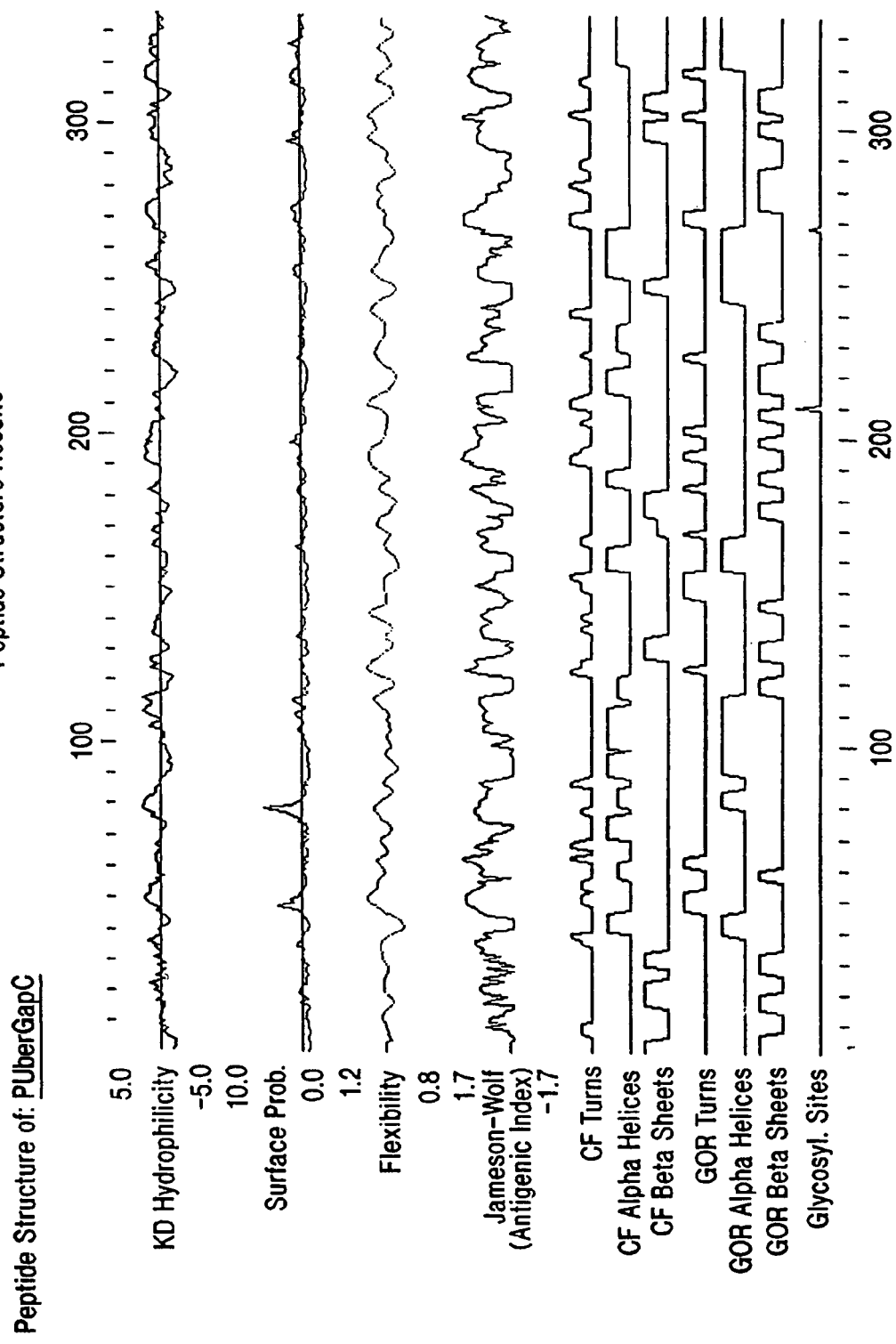

FIG. 12 shows a Kyte-Doolittle hydropathy plot, averaged over a window of 7, an Emini surface probability plot, a Karplus-Schulz chain flexibility plot, a Jameson-Wolf antigenic index plot, and both thou-Fasman and Garnier-Osguthorpe-Robson secondary structure plots for the GapC protein isolated from S. parauberis.

Figure 13:
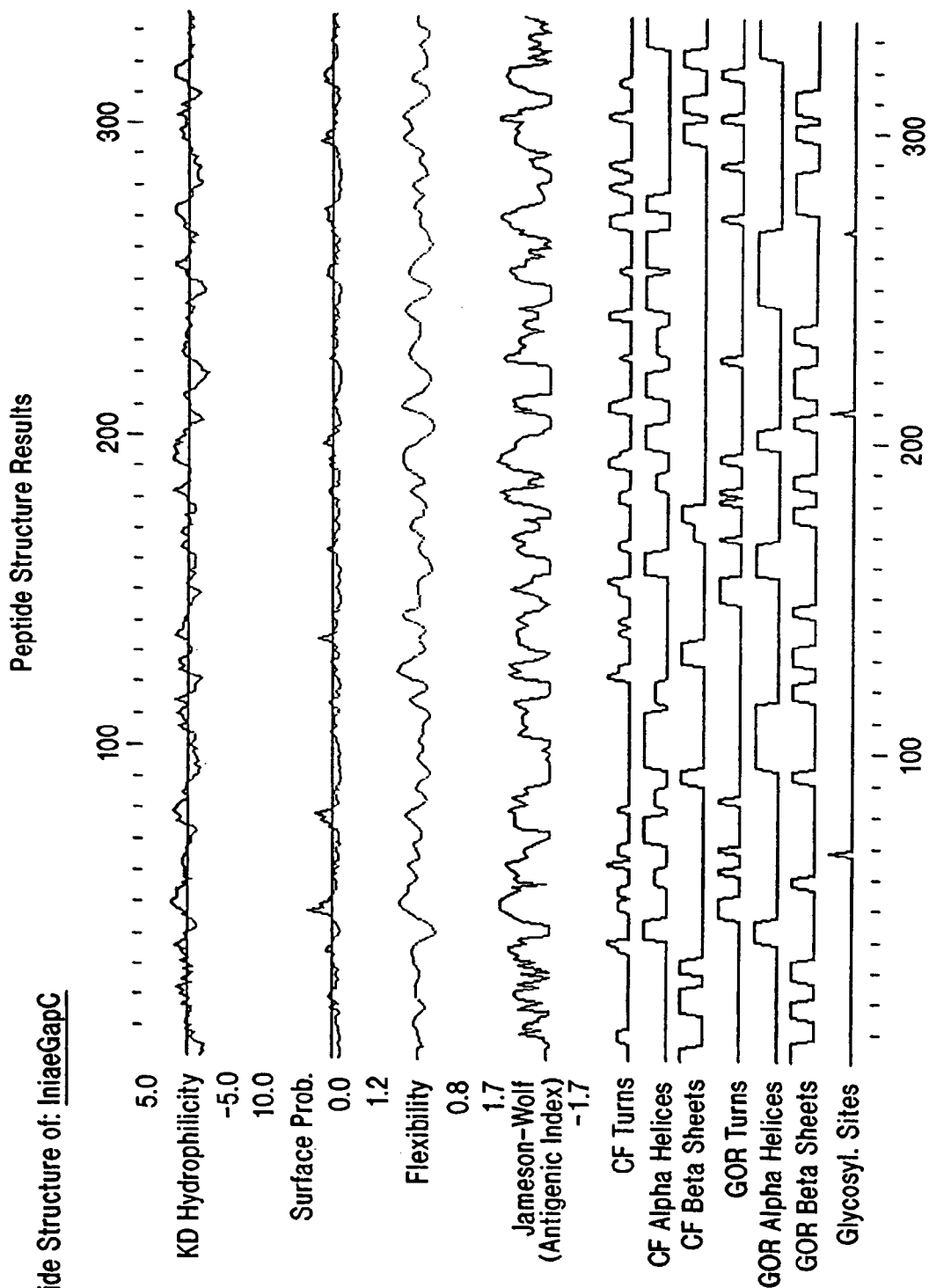

FIG. 13 shows a Kyte-Doolittle hydropathy plot, averaged over a window of 7, an Emini surface probability plot, a Karplus-Schulz chain flexibility plot, a Jameson-Wolf antigenic index plot, and both Chou-Fasman and Garnier-Osguthorpe-Robson secondary structure plots for the GapC protein isolated from S. iniae.

Figure 14:
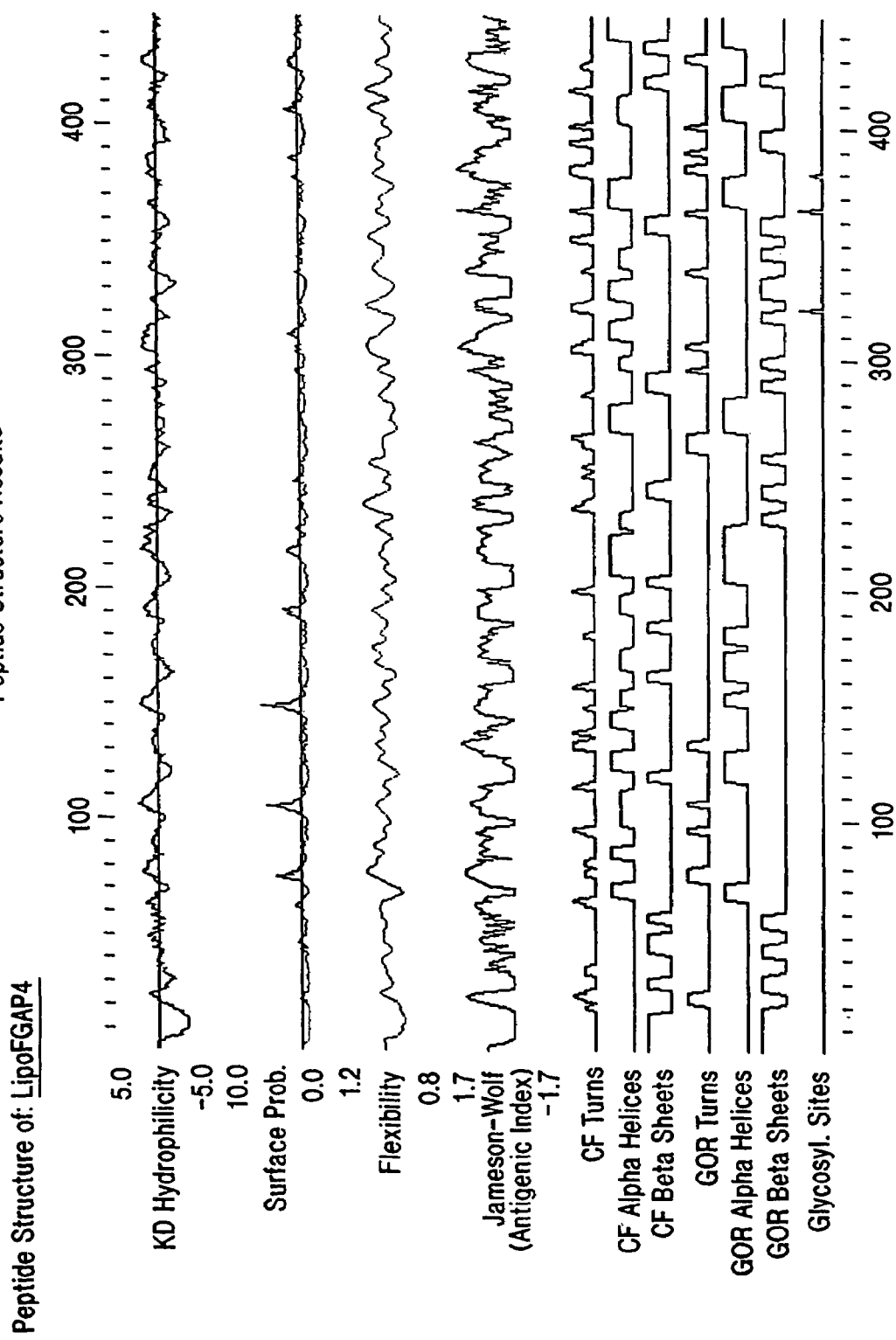

FIG. 14 shows a Kyte-Doolittle hydropathy plot, averaged over a window of 7, an Emini surface probability plot, a Karplus-Schulz chain flexibility plot, a Jameson-Wolf antigenic index plot, and both Chou-Fasman and Garnier-Osguthorpe-Robson secondary structure plots for LipoF-GAP4 (SEQ ID NO:22), the chimeric GapC protein.

Figure 15:
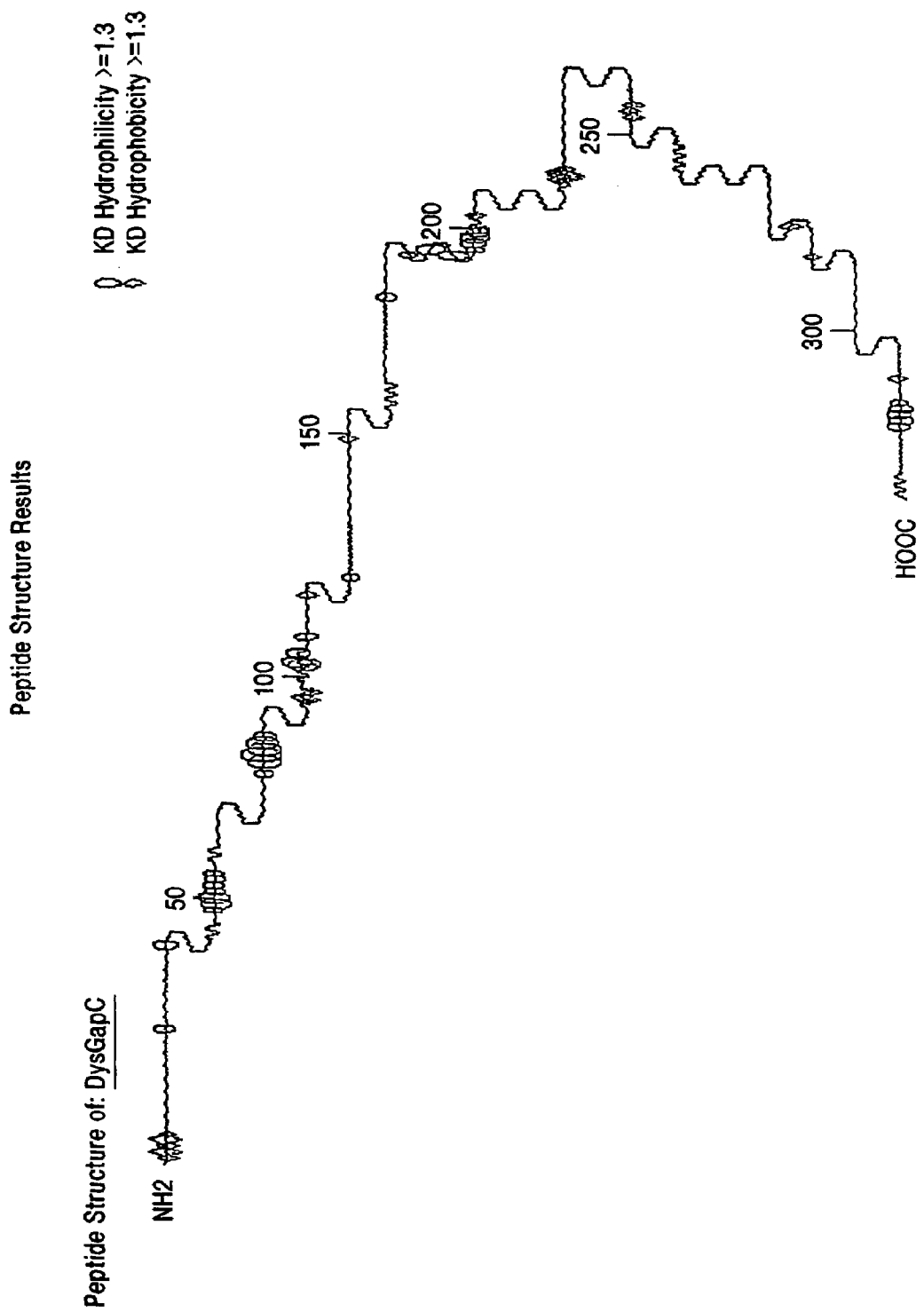

FIG. 15 is a diagrammatic representation of the Chou-Fasman secondary structure plot for the GapC protein isolated from S. dysgal.

Figure 16:
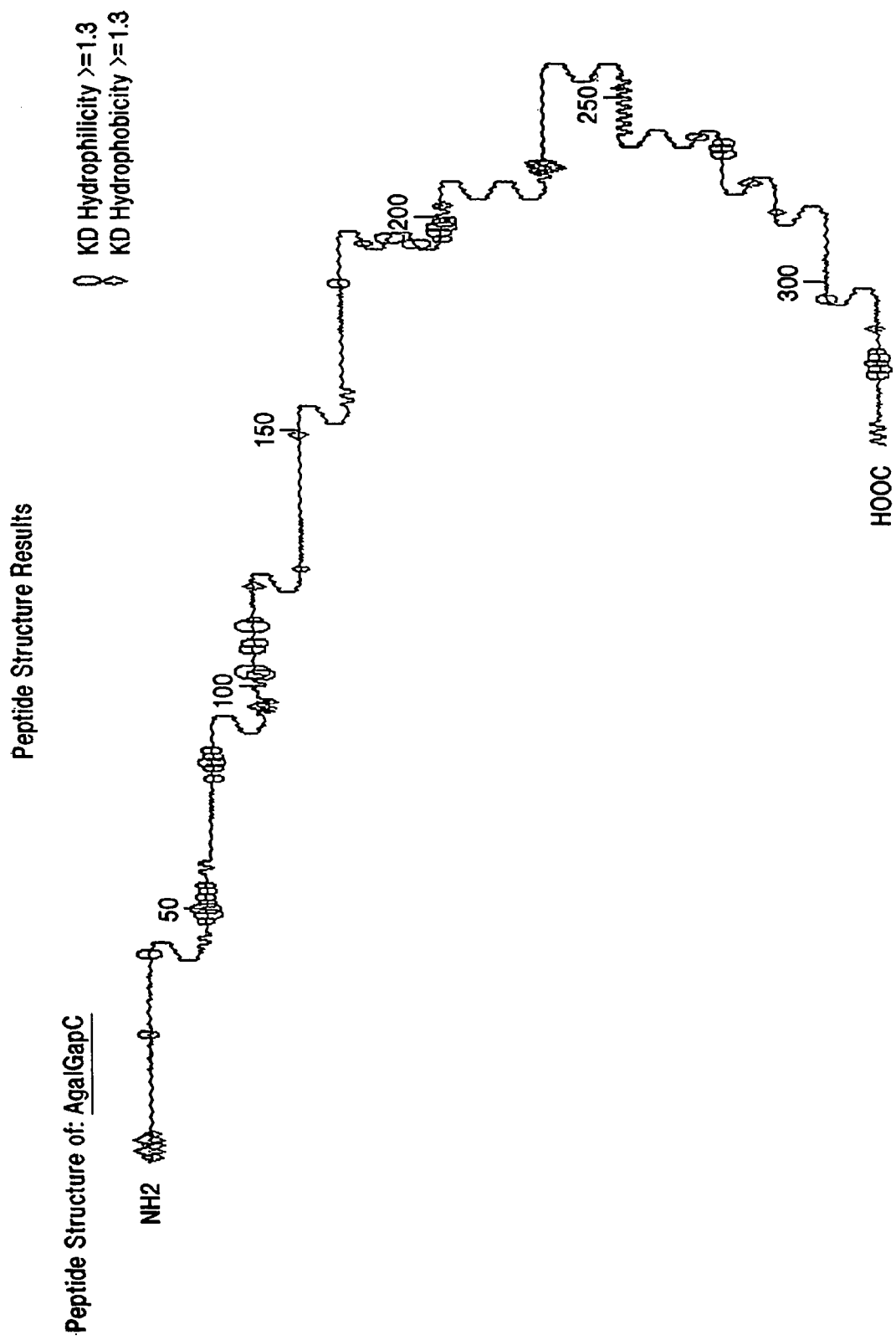
Figure 17:
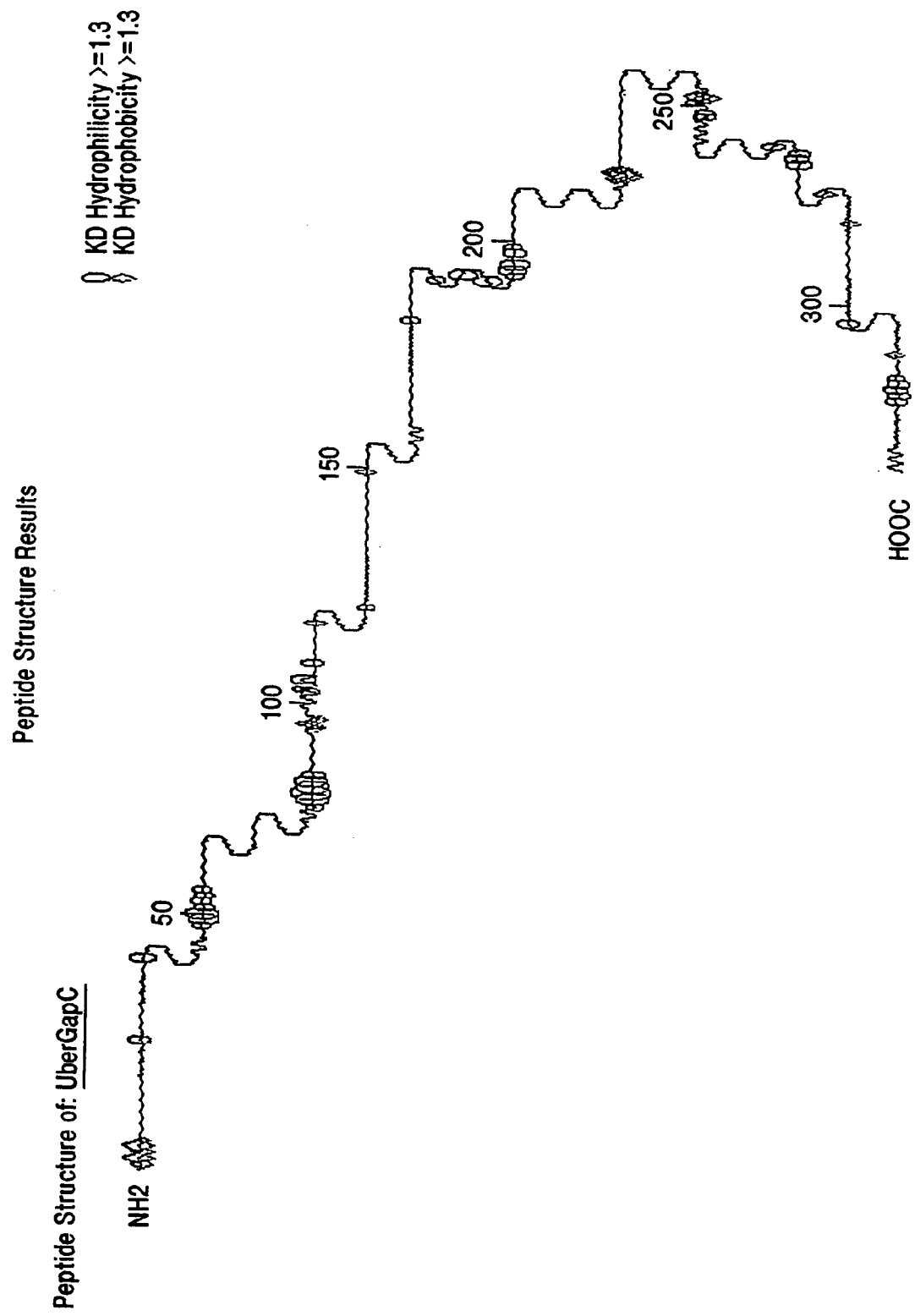

FIG. 16 is a diagrammatic representation of the Chou-Fasman secondary structure plot for the GapC protein isolated from S. agal FIG. 17 is a diagrammatic representation of the Chou-Fasman secondary structure plot for the GapC protein isolated from S. uberis.

Figure 18:
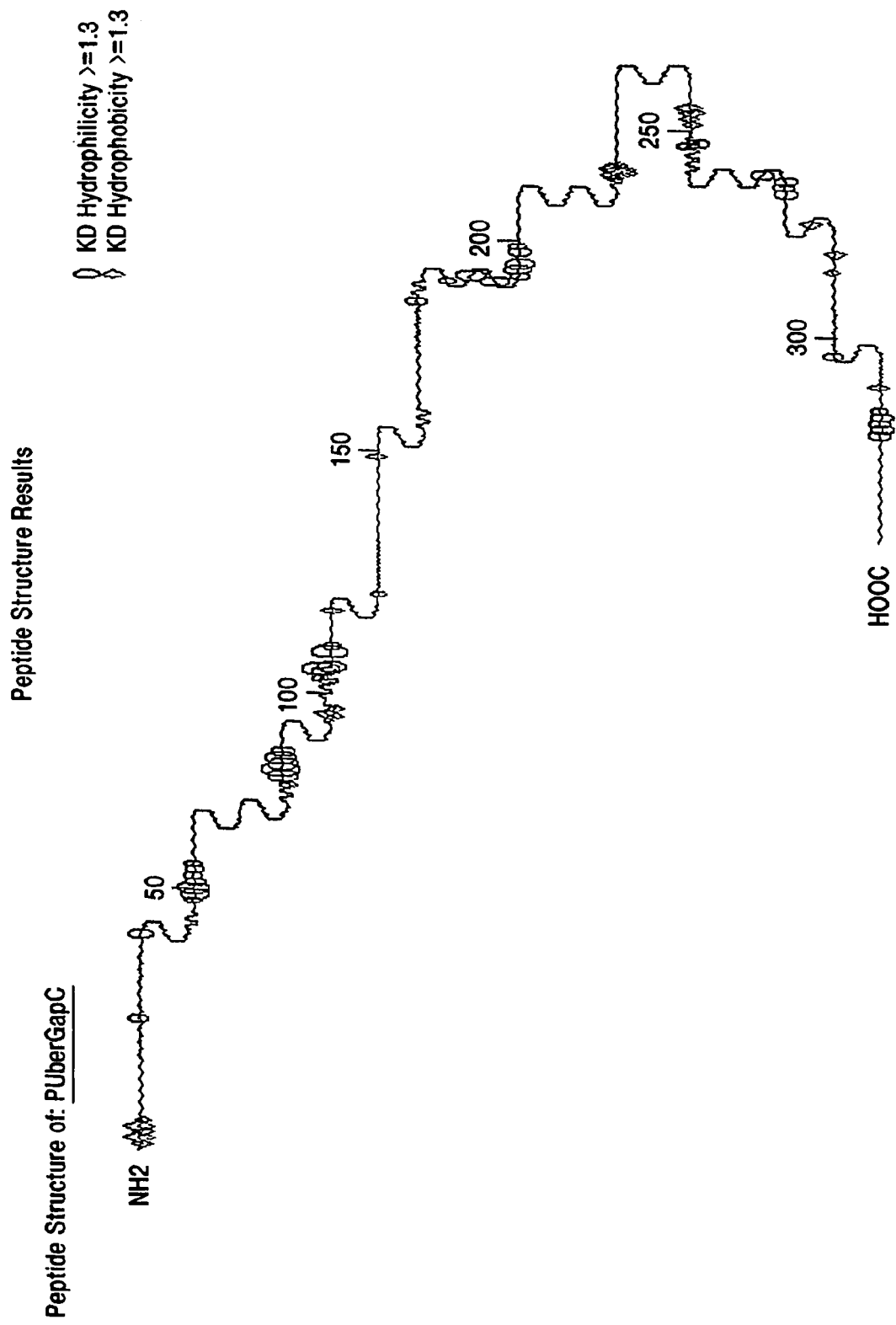

FIG. 18 is a diagrammatic representation of the Chou-Fasman secondary structure plot for the GapC protein isolated from S. parauberis.

Figure 19:
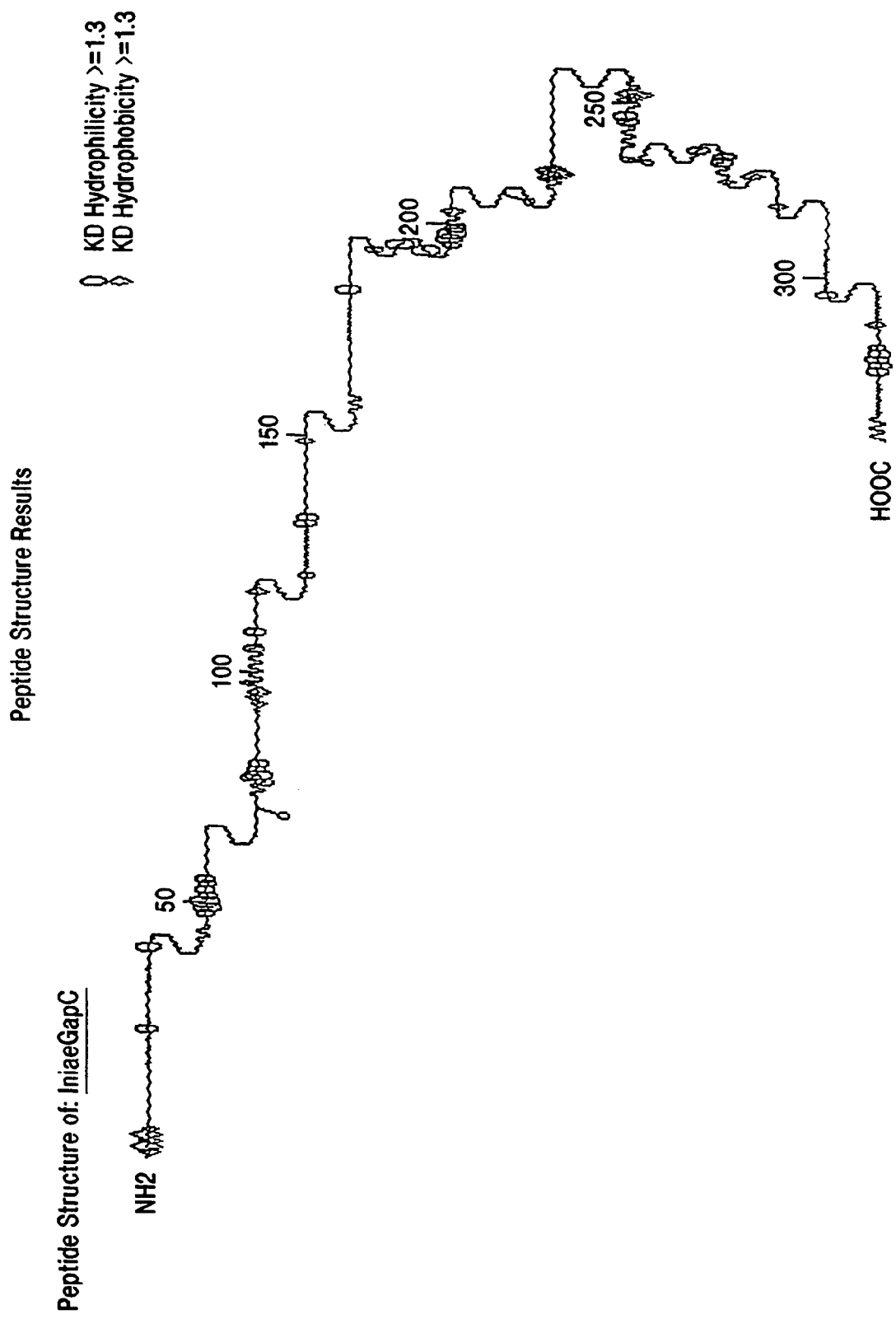

FIG. 19 is a diagrammatic representation of the Chou-Fasman secondary structure plot for the GapC protein isolated from and S. iniae.

Figure 20:
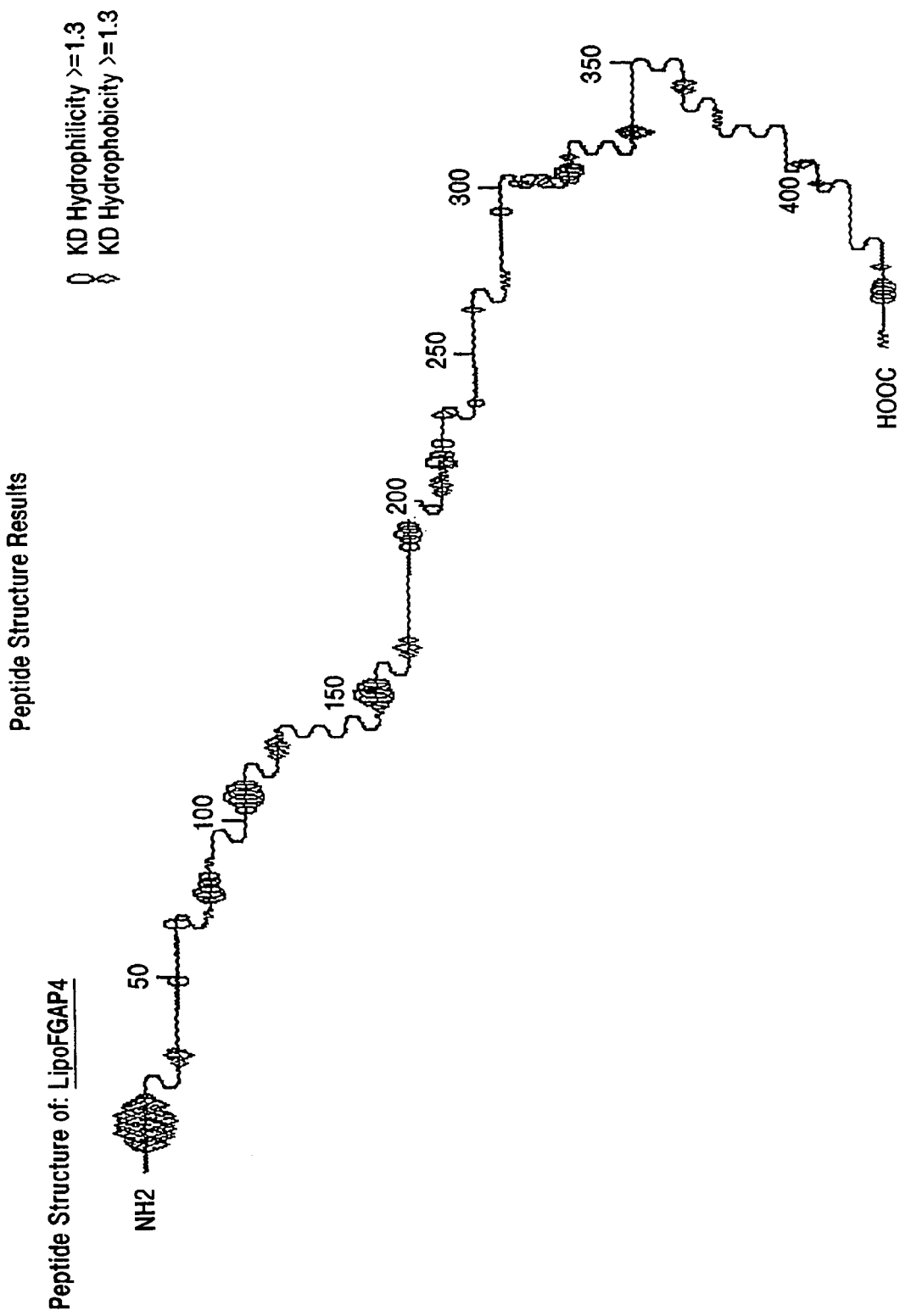

FIG. 20 is a diagrammatic representation of the Chou-Fasman secondary structure plot for LipoFGAP4 (SEQ ID NO:22), the chimeric GapC protein.

Figure 21:
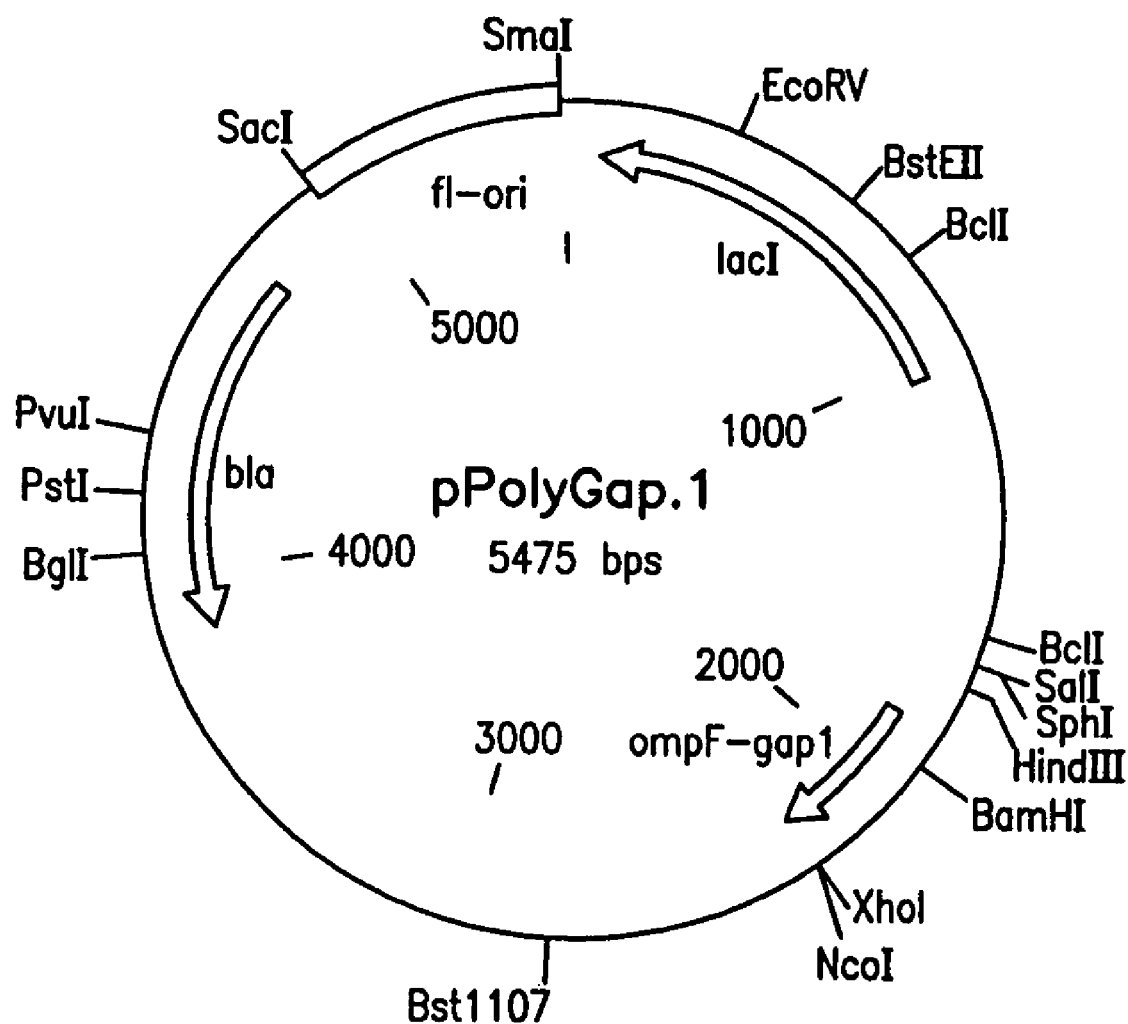
Figure 22:
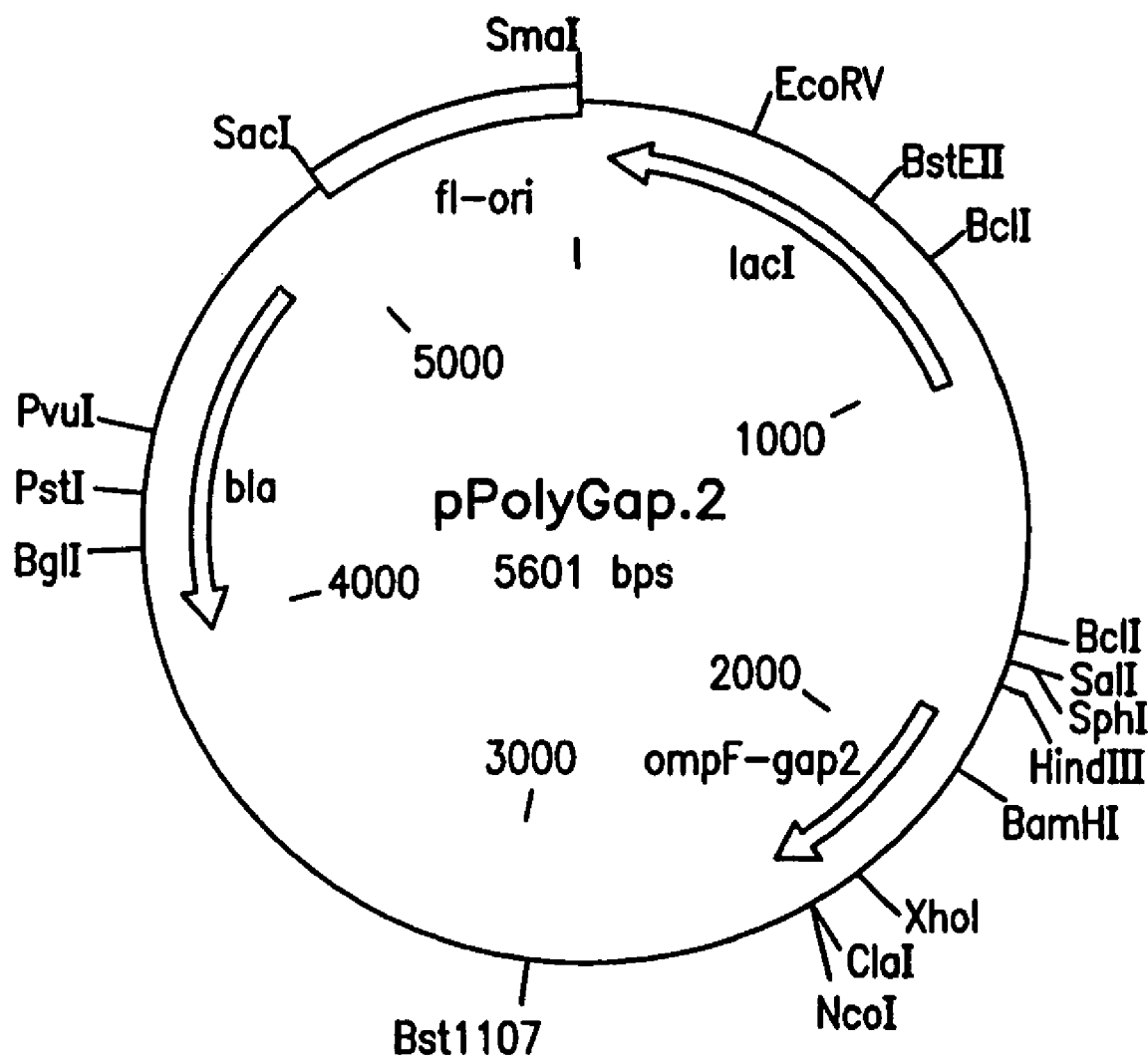
Figure 23:
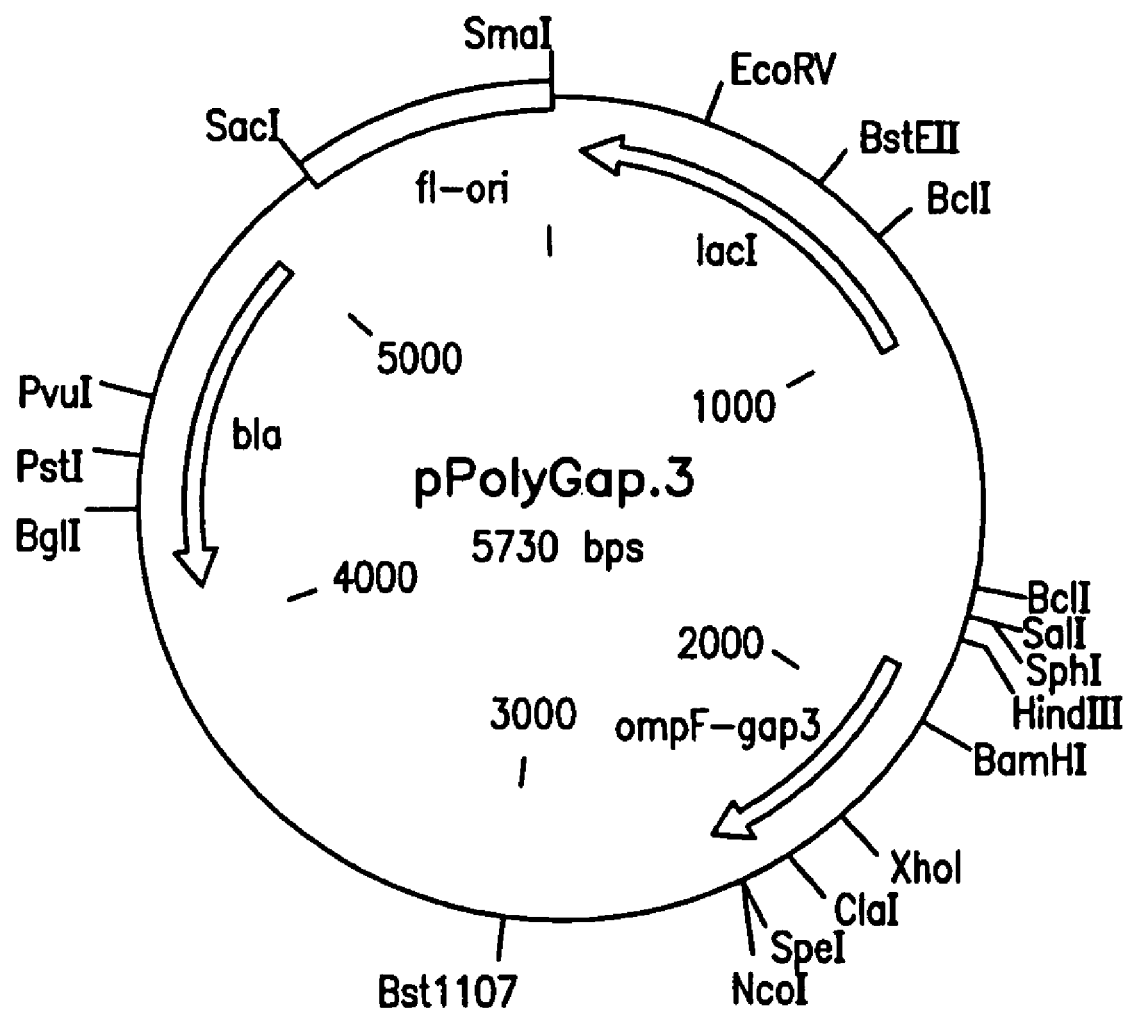
Figure 24:
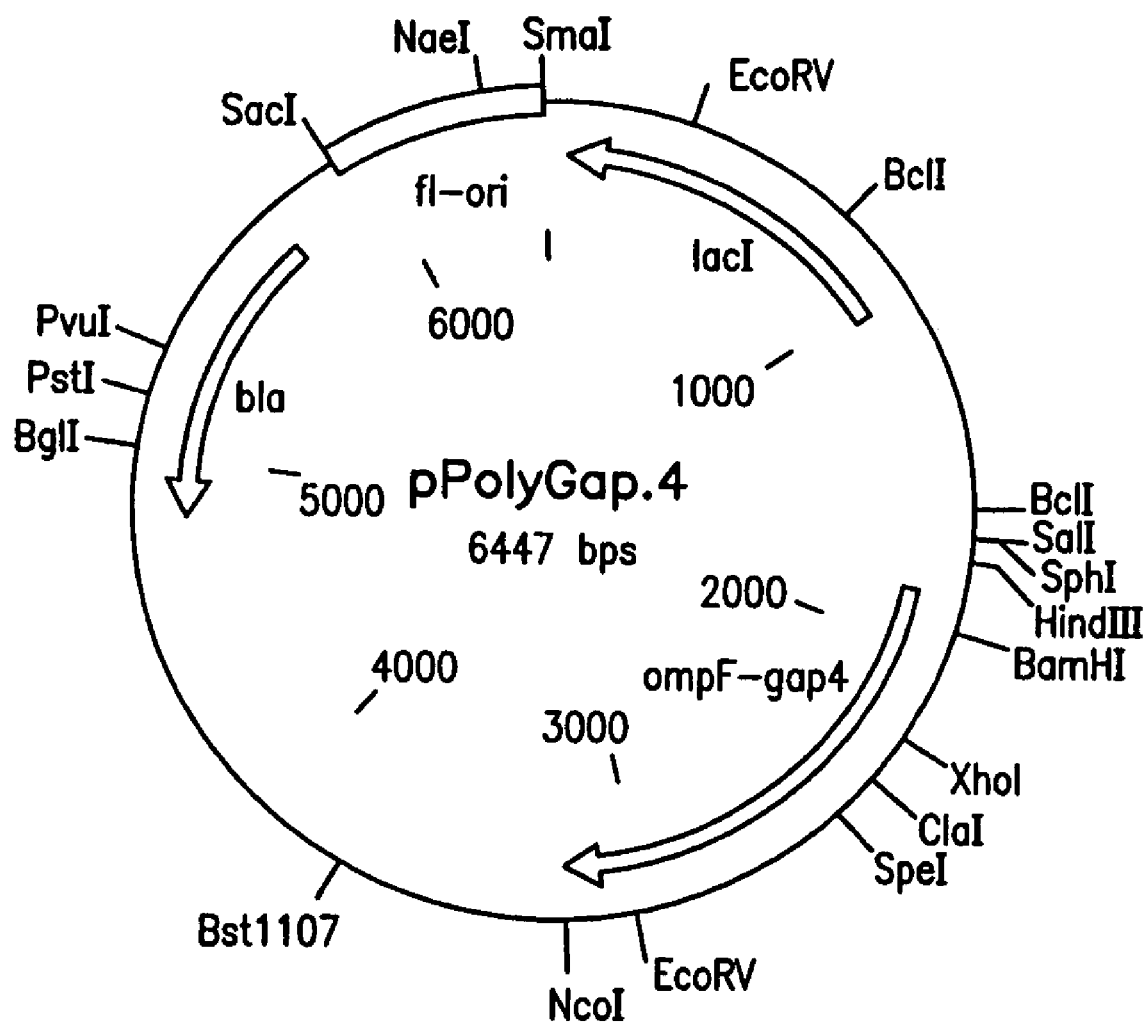
Figure 25:
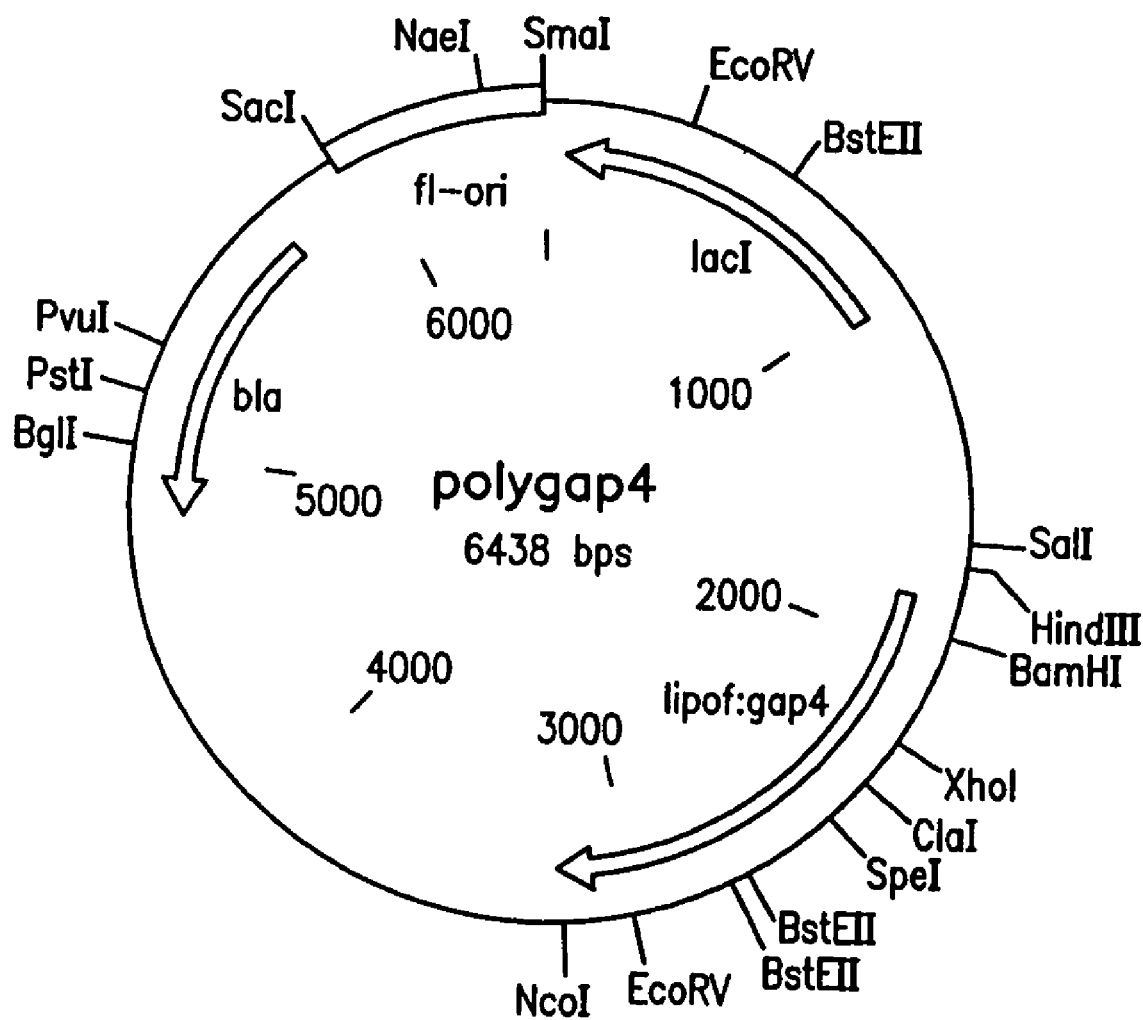

FIG. 21 is a diagram of plasmid pPolyGap.1.
FIG. 22 is a diagram of plasmid pPolyGap.2.
FIG. 23 is a diagram of plasmid pPolyGap.3.
FIG. 24 is a diagram of plasmid pPolyGap.4
FIG. 25 is a diagram of plasmid polygap4.

DETAILED DESCRIPTION

The practice of the present invention will employ, unless otherwise indicated, conventional techniques of molecular biology, microbiology, recombinant DNA technology, and immunology, which are within the skill of the art. Such techniques are explained fully in the literature. See, e.g., Sambrook, Fritsch & Maniatis, *Molecular Cloning: A Laboratory Manual*, Vols. I, II and III, Second Edition (1989); Perbal, B., *A Practical Guide to Molecular Cloning* (1984); the series, *Methods In Enzymology* (S. Colowick and N. Kaplan eds., Academic Press, Inc.); and *Handbook of Experimental Immunology*, Vols. I-IV (D. M. Weir and C. C. Blackwell eds., 1986, Blackwell Scientific Publications).

All publications, patents and patent applications cited herein, whether supra or infra, are hereby incorporated by reference in their entirety.

The following amino acid abbreviations are used throughout the text:

Alanine: Ala (A) Arginine: Arg (R)
Asparagine: Asn (N) Aspartic acid: Asp (D)
Cysteine: Cys (C) Glutamine: Gln (Q)
Glutamic acid: Glu (E) Glycine: Gly (G)
Histidine: His (H) Isoleucine: Ile (I)
Leucine: Leu (L) Lysine: Lys (K)
Methionine: Met (M) Phenylalanine: Phe (F)
Proline: Pro (P) Serine: Ser (S)
Threonine: Thr (T) Tryptophan: Trp (W)
Tyrosine: Tyr (Y) Valine: Val (V)

A. DEFINITIONS

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "a *Streptococcus* GapC protein" includes a mixture of two or more such proteins, and the like.

The terms "GapC protein" and "GapC plasmin binding protein" (used interchangeably herein) or a nucleotide sequence encoding the same, intends a protein or a nucleotide sequence, respectively, which is derived from a GapC gene found in a variety of *Streptococcus* species, including, without limitation certain strains of group A *streptococci* (Lottenbery, R., et al., (1987) *Infect. Immun.*55:1914-1918). The nucleotide sequence of representative *Streptococcus* gapC genes, and the corresponding amino acid sequence of the GapC proteins encoded by these genes, are depicted in the Figures. In particular, FIGS. 1 through 5 depict the isolated nucleotide sequences and isolated amino acid sequences of *S. dysgalactiae* (SEQ ID NO:11 and SEQ ID NO: 12, respectively), *S. agalactiae*(SEQ ID NO:13 and SEQ ID NO:14, respectively), *S. uberis* (SEQ ID NO:15 and SEQ ID NO:16, respectively), *S. parauberis* (SEQ ID NO:17 and SEQ ID NO:18, respectively,), and *S. iniae* (SEQ ID NO:19 and SEQ ID NO:20, respectively). However, a GapC protein as defined herein is not limited to the depicted sequences as subtypes of each of these *Streptococcus* species are known and variations in GapC proteins will occur between them.

Representative gapC genes, derived from *S. dysgalactiae, S. agalactiae, S. uberis*, and *S. parauberis*, are found in the plasmids pET15bgapC, pMF521c, pMF521a, pMF521d, and pMF521e, respectively.

Furthermore, the derived protein or nucleotide sequences need not be physically derived from the gene described above, but may be generated in any manner, including for example, chemical synthesis, isolation (e.g., from *S. dysgalactiae* ) or by recombinant production, based on the information provided herein. Additionally, the term intends proteins having amino acid sequences substantially homologous (as defined below) to contiguous amino acid sequences encoded by the genes, which display immunological and/or plasmin-binding activity.

Thus, the terms intend full-length, as well as immunogenic, truncated and partial sequences, and active analogs and precursor forms of the proteins. Also included in the term are nucleotide fragments of the gene that include at least about 8 contiguous base pairs, more preferably at least about 10-20 contiguous base pairs, and most preferably at least about 25 to 50, or more, contiguous base pairs of the gene, or any integers between these values. Such fragments are useful as probes and in diagnostic methods, discussed more fully below.

The terms also include those forms possessing, as well as lacking, a signal sequence, if such is present, as well as the nucleic acid sequences coding therefore. Additionally, the term intends forms of the GapC proteins which lack a membrane anchor region, and nucleic acid sequences encoding proteins with such deletions. Such deletions may be desirable in systems that do not provide for secretion of the protein. Furthermore, the plasmin-binding domains of the proteins, may or may not be present. Thus, for example, if the GapC plasmin-binding protein will be used to purify plasmin, the plasmin-binding domain will generally be retained. If the protein is to be used in vaccine compositions, immunogenic epitopes which may or may not include the plasmin-binding domain, will be present.

The terms also include proteins in neutral form or in the form of basic or acid addition salts depending on the mode of preparation. Such acid addition salts may involve free amino groups and basic salts may be formed with free carboxyls. Pharmaceutically acceptable basic and acid addition salts are discussed further below. In addition, the proteins may be modified by combination with other biological materials such as lipids (both those occurring naturally with the molecule or other lipids that do not destroy immunological activity) and saccharides, or by side chain modification, such as acetylation of amino groups, phosphorylation of hydroxyl side chains, oxidation of sulfhydryl groups, glycosylation of amino acid residues, as well as other modifications of the encoded primary sequence.

The term therefore intends deletions, additions and substitutions to the sequence, so long as the polypeptide functions to produce an immunological response as defined herein. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine threonine, tyrosine. Phenylalanine, tryptophan, and tyrosine are sometimes classified as aromatic amino acids. For example, it is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the reference molecule, but possessing minor amino acid substitutions that do not substantially affect the immunogenicity and/or plasmin-binding affinity of the protein, are therefore within the definition of the reference polypeptide.

For example, the polypeptide of interest may include up to about 5-10 conservative or non-conservative amino acid substitutions, or even up to about 15-25 or 20-50 conservative or non-conservative amino acid substitutions, or any integer between these values, so long as the desired function of the molecule remains intact.

In this regard, GapC proteins isolated from *streptococci* exhibit several variable regions in their amino acid sequences, located at amino acid positions 62 to 81; 102 to 112; 165 to 172; 248 to 271; and 286 to 305. These regions, which in *S. dysgalactiae, S. agalactiae, S. uberis, S. parauberis* and *S. iniae* exhibit from 1 to 9 amino acid substitutions, are likely to be amenable to variation without substantially affecting immunogenic or enzymatic function.

Similarly, substitutions occurring in the transmembrane binding domain, if present, and the signal sequence, if present, normally will not affect immunogenicity. One of skill in the art may readily determine other regions of the molecule of interest that can tolerate change by reference to the protein structure plots shown in FIGS. 9 to 20 herein.

The term "streptococcal GapC protein" intends a GapC plasmin-binding protein, as defined above, derived from a streptococcal species that produces the same, including, but not limited to *S. dysgalactiae, S. agalactiae, S. uberis, S. parauberis*, and *S. iniae*. For example, a "*S. dysgalactiae* GapC protein" is a GapC plasmin-binding protein as defined above, derived from *S. dysgalactiae*. Similarly, an "*S. agalactiae* GapC protein" intends a gapC binding protein derived from *S. agalactiae*.

"Wild type" or "native" proteins or polypeptides refer to proteins or polypeptides isolated from the source in which the proteins naturally occur. "Recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

An "isolated" protein or polypeptide is a protein or polypeptide molecule separate and discrete from the whole organism with which the molecule is found in nature; or a protein or polypeptide devoid, in whole or part, of sequences normally associated with it in nature; or a sequence, as it exists in nature, but having heterologous sequences (as defined below) in association therewith.

The term "functionally equivalent" intends that the amino acid sequence of a GapC plasmin-binding protein is one that will elicit a substantially equivalent or enhanced immunological response, as defined above, as compared to the response elicited by a GapC plasmin-binding protein having identity with the reference GapC plasmin-binding protein, or an immunogenic portion thereof.

The term "epitope" refers to the site on an antigen or hapten to which specific B cells and/or T cells respond. The term is also used interchangeably with "antigenic determinant" or "antigenic determinant site." Antibodies that recognize the same epitope can be identified in a simple immunoassay showing the ability of one antibody to block the binding of another antibody to a target antigen. Epitopes may include 3 to 5 amino acids, more preferably 5 to 10 amino acids, up to the full length of the reference molecule.

The term "multiple epitope" protein or polypeptide specifies a sequence of amino acids comprising an epitope as defined herein, which contains at least one epitope repeated two or more times within a linear molecule. The repeating sequence need not be directly connected to itself, is not repeated in nature in the same manner and, further, may be present within a larger sequence which includes other amino acids that are not repeated. For the purposes of this invention, the epitope sequence may either be an exact copy of a wild-type epitope sequence, or a sequence which is "functionally equivalent" as defined herein. refers to a multiple epitope protein or polypeptide as defined herein that is produced by recombinant or synthetic methods.

A "fusion" or "chimeric" protein or polypeptide is one in which amino acid sequences from more than one source are joined. Such molecules may be produced synthetically or recombinantly, as described further herein (see the section entitled "Production of GapC Plasmin-Binding Proteins" infra). Hence, the term "multiple epitope fusion protein or polypeptide" refers to a multiple epitope protein or polypeptide as defined herein which is made by either synthetic or recombinant means.

In this regard, a multiple epitope fusion protein comprising the variable regions in the amino acid sequences of the GapC proteins referred to above may be produced. The amino acid sequence for a representative GapC multiple epitope fusion protein, and a corresponding polynucleotide coding sequence, is depicted in FIGS. 6A-6C herein (SEQ ID NO:22). Methods for recombinantly producing the protein, including a method for constructing the polyGap4 plasmid containing the chimeric coding sequence (diagramed in FIG. 25) and a method for expressing the protein from the polyGap4 plasmid, are described in Examples 4 and 5 infra.

The terms "immunogenic" protein or polypeptide refer to an amino acid sequence which elicits an immunological response as described herein. An "immunogenic" protein or polypeptide, as used herein, includes the full-length sequence of the GapC plasmin-binding protein in question, with or without the signal sequence, membrane anchor domain and/or plasmin-binding domain, analogs thereof, or immunogenic fragments thereof. By "immunogenic fragment" is meant a fragment of a GapC plasmin-binding protein which includes one or more epitopes and thus elicits the immunological response described above. Such fragments can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1986) *Molec. Immunol.* 23:709-715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., *Epitope Mapping Protocols*, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., *Proc. Natl. Acad. Sci USA* (1981) 78:3824-3828 for determining antigenicity profiles, and the Kyte-Doolittle technique, Kyte et al., *J. Mol. Biol.* (1982) 157:105-132 for hydropathy plots. FIGS. 9 to 20 herein depict Kyte-Doolittle profiles for representative proteins encompassed by the invention.

Immunogenic fragments, for purposes of the present invention, will usually include at least about 3 amino acids, preferably at least about 5 amino acids, more preferably at least about 10-15 amino acids, and most preferably 25 or more amino acids, of the parent GapC plasmin-binding-binding protein molecule. There is no critical upper limit to the length of the fragment, which may comprise nearly the full-length of the protein sequence, or even a fusion protein comprising two or more epitopes of GapC.

An "immunogenic composition" is a composition that comprises an antigenic molecule where administration of the composition to a subject results in the development in the subject of a humoral and/or a cellular immune response to the antigenic molecule of interest.

By "subunit vaccine composition" is meant a composition containing at least one immunogenic polypeptide, but not all antigens, derived from or homologous to an antigen from a pathogen of interest. Such a composition is substantially free of intact pathogen cells or particles, or the lysate of such cells or particles. Thus, a "subunit vaccine composition" is prepared from at least partially purified (preferably substantially purified) immunogenic polypeptides from the pathogen, or recombinant analogs thereof. A subunit vaccine composition can comprise the subunit antigen or antigens of interest substantially free of other antigens or polypeptides from the pathogen.

By "pharmaceutically acceptable" or "pharmacologically acceptable" is meant a material which is not biologically or otherwise undesirable, i.e., the material may be administered to an individual in a formulation or composition without causing any undesirable biological effects or interacting in a deleterious manner with any of the components of the composition in which it is contained.

An "immunological response" to a composition or vaccine is the development in the host of a cellular and/or antibody-mediated immune response to the composition or vaccine of interest. Usually, an "immunological response" includes but is not limited to one or more of the following effects: the production of antibodies, B cells, helper T cells, suppressor T cells, and/or cytotoxic T cells and/or γδ T cells, directed specifically to an antigen or antigens included in the composition or vaccine of interest. Preferably, the host will display either a therapeutic or protective immunological response such that resistance of the mammary gland to new infection will be enhanced and/or the clinical severity of the disease reduced. Such protection will be demonstrated by either a reduction or lack of symptoms normally displayed by an infected host and/or a quicker recovery time.

By "nucleic acid immunization" is meant the introduction of a nucleic acid molecule encoding one or more selected antigens into a host cell, for the in vivo expression of an antigen, antigens, an epitope, or epitopes. The nucleic acid molecule can be introduced directly into a recipient subject, such as by injection, inhalation, oral, intranasal and mucosal administration, or the like, or can be introduced ex vivo, into cells which have been removed from the host. In the latter case, the transformed cells are reintroduced into the subject where an immune response can be mounted against the antigen encoded by the nucleic acid molecule.

The term "treatment" as used herein refers to either (1) the prevention of infection or reinfection (prophylaxis), or (2) the reduction or elimination of symptoms of the disease of interest (therapy).

By "mastitis" is meant an inflammation of the mammary gland in mammals, including in cows, ewes, goats, sows, mares, and the like, caused by the presence of pathogenic microorganisms, such as S. uberis. The infection manifests itself by the infiltration of phagocytic cells in the gland. Generally, 4 clinical types of mastitis are recognized: (1) peracute, associated with swelling, heat, pain, and abnormal secretion in the gland and accompanied by fever and other signs of systemic disturbance, such as marked depression, rapid weak pulse, sunken eyes, weakness and complete anorexia; (2) acute, with changes in the gland similar to those above but where fever, anorexia and depression are slight to moderate; (3) subacute, where no systemic changes are displayed and the changes in the gland and its secretion are less marked: and (4) subclinical, where the inflammatory reaction is detectable only by standard tests for mastitis.

Standard tests for the detection of mastitis include but are not limited to, the California Mastitis Test, the Wisconsin Mastitis Test, the Nagase test, the electronic cell count and somatic cell counts used to detect a persistently high white blood cell content in milk. In general, a somatic cell count of about 300,000 to about 500,000 cells per ml or higher, in milk will indicate the presence of infection. Thus, a vaccine is considered effective in the treatment and/or prevention of mastitis when, for example, the somatic cell count in milk is retained below about 500,000 cells per ml. For a discussion of mastitis and the diagnosis thereof, see, e.g., *The Merck Veterinary Manual: A Handbook of Diagnosis, Therapy, and Disease Prevention and Control for the Veterinarian*, Merck and Co., Rahway, N.J., 1991.

By the terms "vertebrate," "subject," and "vertebrate subject" are meant any member of the subphylum Chordata, including, without limitation, mammals such as cattle, sheep, pigs, goats, horses, and humans; domestic animals such as dogs and cats; and birds, including domestic, wild and game birds such as cocks and hens including chickens, turkeys and other gallinaceous birds; and fish. The term does not denote a particular age. Thus, both adult and newborn animals, as well as fetuses, are intended to be covered.

A "nucleic acid" molecule can include, but is not limited to, procaryotic sequences, eucaryotic MRNA, cDNA from eucaryotic MRNA, genomic DNA sequences from eucaryotic (e.g., mammalian) DNA, and even synthetic DNA sequences. The term also captures sequences that include any of the known base analogs of DNA and RNA.

An "isolated" nucleic acid molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences (as defined below) in association therewith. The term "isolated" in the context of a polynucleotide intends that the polynucleotide is isolated from the chromosome with which it is normally associated, and is isolated from the complete genomic sequence in which it normally occurs.

"Purified polynucleotide" refers to a polynucleotide of interest or fragment thereof which is essentially free, e.g., contains less than about 50%, preferably less than about 70%, and more preferably less than about 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

A "coding sequence" or a "nucleotide sequence encoding" a particular protein, is a nucleotide sequence which is transcribed and translated into a polypeptide in vitro or in vivo when placed under the control of appropriate regulatory elements. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic MRNA, genomic DNA sequences from eucaryotic (e.g., mammalian) DNA, and even synthetic DNA sequences. A transcription termination sequence will usually be located 3' to the coding sequence. A "complementary" sequence is one in which the nitrogenous base at a given nucleotide position is the complement of the nitrogenous base appearing at the same position in the reference sequence. To illustrate, the complement of adenosine is tyrosine, and vice versa; similarly, cytosine is complementary to guanine, and vice versa; hence, the complement of the reference sequence 5'-ATGCTGA-3' would be 5'-TACGACT-3'.

A "wild-type" or "native" sequence, as used herein, refers to polypeptide encoding sequences that are essentially as they are found in nature, e.g., the *S. dysgalactiae* GapC protein encoding sequences depicted in FIGS. 1A-1B (SEQ ID NO:12).

"Recombinant" as used herein to describe a nucleic acid molecule means a polynucleotide of genomic, cDNA, semi-synthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting procaryotic microorganisms or eucaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

"Homology" refers to the percent identity between two polynucleotide or two polypeptide moieties. Two DNA, or two polypeptide sequences are "substantially homologous" to each other when the sequences exhibit at least about 80%-85%, preferably at least about 90%, and most preferably at least about 95%-98% sequence identity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman (1981) *Advances in Appl. Math.* 2:482-489 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions as defined for that particular system. Defining appropriate hybridization conditions is within the skill of the art. See, e.g., Sambrook et al., supra; *DNA Cloning*, supra; *Nucleic Acid Hybridization*, supra.

By the term "degenerate variant" is intended a polynucleotide containing changes in the nucleic acid sequence thereof, that encodes a polypeptide having the same amino acid sequence as the polypeptide encoded by the polynucleotide from which the degenerate variant is derived.

Techniques for determining amino acid sequence "similarity" are well known in the art. In general, "similarity" means the exact amino acid to amino acid comparison of two or more polypeptides at the appropriate place, where amino acids are identical or possess similar chemical and/or physical properties such as charge or hydrophobicity. A so-termed "percent similarity" then can be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded thereby, and comparing this to a second amino acid sequence. In general, "identity" refers to an exact nucleotide to nucleotide or amino acid to amino acid correspondence of two polynucleotides or polypeptide sequences, respectively.

A "heterologous" region of a DNA construct is an identifiable segment of DNA within or attached to another DNA molecule that is not found in association with the other molecule in nature. Thus, when the heterologous region encodes a bacterial gene, the gene will usually be flanked by DNA that does not flank the bacterial gene in the genome of the source bacteria. Another example of the heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

A "vector" is a replicon, such as a plasmid, phage, or cosmid, to which another DNA segment may be attached so as to bring about the replication of the attached segment. A vector is capable of transferring gene sequences to target cells (e.g., bacterial plasmid vectors, viral vectors, non-viral vectors, particulate carriers, and liposomes).

Typically, the terms "vector construct," "expression vector," "gene expression vector," "gene delivery vector," "gene transfer vector," and "expression cassette" all refer to an assembly which is capable of directing the expression of a sequence or gene of interest. Thus, the terms include cloning and expression vehicles, as well as viral vectors.

These assemblies include a promoter which is operably linked to the sequences or gene(s) of interest. Other control elements may be present as well. The expression cassettes described herein may be contained within a plasmid construct. In addition to the components of the expression cassette, the plasmid construct may also include a bacterial origin of replication, one or more selectable markers, a signal which allows the plasmid construct to exist as single-stranded DNA (e.g., a M13 origin of replication), a multiple cloning site, and a "mammalian" origin of replication (e.g., a SV40 or adenovirus origin of replication).

DNA "control elements" refers collectively to transcription promoters, transcription enhancer elements, transcription termination sequences, polyadenylation sequences (located 3' to the translation stop codon), sequences for optimization of initiation of translation (located 5' to the coding sequence), translation termination sequences, upstream regulatory domains, ribosome binding sites and the like, which collectively provide for the transcription and translation of a coding sequence in a host cell. See e.g., McCaughan et al. (1995) *PNAS USA* 92:5431-5435; Kochetov et al (1998) *FEBS Letts.* 440:351-355. Not all of these control sequences need always be present in a recombinant vector so long as the desired gene is capable of being transcribed and translated.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence. Similarly, "control elements compatible with expression in a subject" are those which are capable of effecting the expression of the coding sequence in that subject.

A control element, such as a promoter, "directs the transcription" of a coding sequence in a cell when RNA polymerase will bind the promoter and transcribe the coding sequence into MRNA, which is then translated into the polypeptide encoded by the coding sequence.

A "host cell" is a cell which has been transformed, or is capable of transformation, by an exogenous nucleic acid molecule.

A cell has been "transformed" by exogenous DNA when such exogenous DNA has been introduced inside the cell membrane. Exogenous DNA may or may not be integrated (covalently linked) into chromosomal DNA making up the genome of the cell. In procaryotes and yeasts, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cells containing the exogenous DNA.

As used herein, a "biological sample" refers to a sample of tissue or fluid isolated from a subject, including but not limited to, for example, blood, plasma, serum, fecal matter, urine, bone marrow, bile, spinal fluid, lymph fluid, samples of the skin, external secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components.

As used herein, the terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. The term "fluorescer" refers to a substance or a portion thereof which is capable of exhibiting fluorescence in the detectable range. Particular examples of labels which may be used under the invention include fluorescein, rhodamine, dansyl, umbelliferone, Texas red, luminol, NADPH and α-β-galactosidase.

MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

General Overview of the Invention

Central to the present invention is the discovery that the GapC protein is capable of eliciting an immune response in a vertebrate subject. Experiments performed in support of the present invention have demonstrated that immunization of dairy cattle with the GapC protein of *S. dysgalactiae* conferred protection against experimental infection with this organism, and furthermore, conferred cross-protection against infection by *S. uberis*.

GapC is produced by a number of different *streptococcus* species. With the exception of several localized variable regions, the amino acid sequences of the GapC proteins produced by those strains are highly conserved. Therefore, it is desirable to construct multiple epitope GapC fusion proteins comprising antigenic determinants taken from both the highly conserved regions of GapC, and the unique regions of GapC proteins from several streptococcal species. Experiments performed in support of the present invention have demonstrated that such a protein is capable of eliciting broad immunity against a variety of streptococcal infections while providing the additional economic advantage of minimizing the number of antigens present in the final formulation, and concomitantly reducing the cost of producing that formulation.

The GapC multiple epitope fusion proteins of the present invention are described by the general structural formula $(A)_x$—$(B)_y$—$(C)_z$ representing a linear amino acid sequence. B is an amino acid sequence of at least five and not more than 1,000 amino acids of an antigenic determinant from a GapC protein, and y is an integer of 2 or more. A and C are each different from B, as well as being different from each other, and are independently an amino acid sequence of an antigenic determinant containing at least five and not more than 1,000 amino acids not immediately adjacent to B in nature. x and z are each independently an integer of 0 or more, wherein at least one of x and z is 1 or more.

Typically, A, B, and C are antigenic determinants from the GapC proteins of one or more bacterial species. In a preferred embodiment, A, B, and C are amino acid sequences comprising one or more antigenic determinants from the GapC protein of one or more of the following species of streptococcus: *S. dysgalactiae; S. agalactiae; S. uberis; S. parauberis*, and *S. iniae*.

In this regard, FIGS. 9 through 13 show plots of the following for the streptococcal GapC proteins employed by the present invention: Kyte-Doolittle hydrophathy, averaged over a window of 7; surface probability according to Emini; chain flexibility according to Karplus-Schulz; antigenicity index according to Jameson-Wolf; secondary structure according to Garnier-Osguthorpe-Robson; secondary structure according to Chou-Fasman; and predicted glycosylation sites. FIGS. 15 through 19 show plots of secondary structure according to Chou-Fasman for the aforementioned proteins.

One of skill in the art can readily use the information presented in FIGS. 9 through 13 and 15 to 19 in view of the teachings of the present specification to identify antigenic regions which may be employed in constructing the chimeric protein of the present invention.

Most preferably, A, B, and/or C include one or more variable regions of the GapC proteins from more than one streptococcus species. In this regard, FIGS. 8A-8C show an amino acid sequence alignment which illustrates regions of homology and variability that exist among GapC proteins from S. dysgalactiae (SEQ IID NO:12). S. agalactiae (SEQ ID NO:14) S. uberis (SEQ ID NO:16) S. parauberis (SEQ ID NO:18) and S. iniae (SEQ ID NO:20). Amino acid sequences for the GapC proteins of S. pyogenes (SEQ ID NO:24). and S. equisimilis (SEQ ID NO:26) are also included. In particular, several variable regions are located at amino acid positions 62 to 81; 102 to 112; 165to 172; 248 to 271; and 286 to 305.

The multiple epitope fusion protein of the present invention may also include spacer sequences interposed between A, B, and/or C. The spacer sequences are typically amino acid sequences of from 1 to 1,000 amino acids, may be the same or different as A, B, or C, and may be the same or different at each other.

The present invention may also include a signal sequence and/or a transmembrane sequence. Examples of suitable signal sequences include the E. coli LipoF signal sequence, and the OmpF signal sequence. Examples of suitable transmembrane sequences include those associated with LipoF and OmpF.

An especially preferred embodiment of the present invention is the multiple epitope fusion protein Gap4. The amino acid sequence of Gap4 (SEQ ID NO:22), a representative multiple epitope GapC fusion protein, is shown in FIGS. 6A-6C, as is the polynucleotide sequence which encodes it (SEQ ID NO:21). Gap4 is a 47.905 kDa chimeric protein of 448 amino acids. Residues 1 to 27 are identical to amino acid residues 1 to 27 of the E. coli LipoF signal sequence. Residues 28 to 123 are identical to residues 1 to 96 of the S. dysgalactiae GapC protein. Residues 124 (leucine) and 125 (glutamic acid) are spacer amino acids. They are followed by residues 126 to 165, which are identical to residues 56 to 95 of S. parauberis as well as to the same residues of S. uberis. Residue 166 (isoleucine) is a spacer amino acid. Residues 167 to 208 are identical to residues 55 to 96 of the S. agalactiae GapC protein. Residues 209 (threonine) and 210 (serine) are spacer amino acids. Residues 211 to 448 are identical to residues 99 to 336 of the S. dysgalactiae GapC protein.

As expressed, Gap4 has a cysteine residue present at the amino terminal end of the mature protein. The LipoF signal sequence and cysteine residue are present to ensure that the chimeric molecule is efficiently secreted from the bacterial host cell and becomes bound to the host cell membrane via the lipid-moiety. The protein may then be extracted from the cell surface via differential solubilization with a detergent such as Sarkosyl or TritonX-100® (see Example 5 infra).

The GapC chimeric proteins of the present invention or antigenic fragments thereof can be provided in subunit vaccine compositions. In addition to use in vaccine compositions, the proteins or antibodies thereto can be used as diagnostic reagents to detect the presence of infection in a vertebrate subject. Similarly, the genes encoding the proteins can be cloned and used to design probes to detect and isolate homologous genes in other bacterial strains. For example, fragments comprising at least about 15-20 nucleotides, more preferably at least about 20-50 nucleotides, and most preferably about 60-100 nucleotides, or any integer between these values, will find use in these embodiments.

The vaccine compositions of the present invention can be used to treat or prevent a wide variety of bacterial infections in vertebrate subjects. For example, vaccine compositions including GapC multiple epitope fusion proteins comprising antigenic determinants from S. dysgalactiae, S. uberis, S. parauberis, S. iniae, and/or group B streptococci (GBS) such as S. agalactiae, can be used to treat streptococcal infections in vertebrate subjects that are caused by these or other species. In particular, S. uberis and S. agalactiae are common bacterial pathogens associated with mastitis in bovine, equine, ovine and goat species. Additionally, group B streptococci, such as S. agalactiae, are known to cause numerous other infections in vertebrates, including septicemia, meningitis, bacteremia, impetigo, arthritis, urinary tract infections, abscesses, spontaneous abortion etc. Hence, vaccine compositions containing chimeric GapC proteins will find use in treating and/or preventing a wide variety of streptococcal infections.

Similarly, GapC multiple epitope fusion proteins comprising antigenic determinants derived from other bacterial genera such as Staphylococcus, Mycobacterium, Escherichia, Pseudomonas, Nocardia, Pasteurella, Clostridium and Mycoplasma will find use for treating bacterial infections caused by species belonging to those genera. Thus, it is readily apparent that chimeric GapC proteins can be used to treat and/or prevent a wide variety of bacterial infections in numerous species.

The GapC multiple epitope fusion proteins of the present invention can be used in vaccine compositions either alone or in combination with other bacterial, fungal, viral or protozoal antigens. These other antigens can be provided separately or even as fusion proteins comprising the GapC chimeric protein fused to one or more of these antigens. For example, other immunogenic proteins from S. uberis, such as the CAMP factor, hyaluronic acid capsule, hyaluronidase, R-like protein and plasminogen activator, can be administered with the chimeric GapC protein. Additionally, immunogenic proteins from other organisms involved in mastitis, such as from the genera Staphylococcus, Corynebacterium, Pseudomonas, Nocardia, Clostridium, Mycobacterium, Mycoplasma, Pasteurella, Prototheca, other streptococci, coliform bacteria, as well as yeast, can be administered along with the GapC fusion proteins described herein to provide a broad spectrum of protection. Thus, for example, immunogenic proteins from Staphylococcus aureus, Str. agalactiae, Str. dysgalactiae, Str. zooepidemicus, Corynebacterium pyogenes, Pseudomonas aeruginosa, Nocardia asteroides, Clostridium perfringens, Escherichia coli, Enterobacter aerogenes and Klebsiella spp. can be provided along with the GapC plasmin-binding proteins of the present invention.

Production of GapC Multiple Epitope Fusion Proteins

The above-described chimeric proteins and active fragments and analogs derived from the same, can be produced by recombinant methods as described herein. These recombinant products can take the form of partial protein sequences, full-length sequences, precursor forms that include signal sequences, or mature forms without signals.

The GapC plasmin-binding protein DNA sequences used to construct the chimeric proteins of the present invention can be isolated by a variety of methods known to those of skill in the art. See, e.g., Sambrook et al., supra. Methods for isolating, cloning and sequencing the gene sequences encoding GapC proteins from *S. dysgalactiae, S. agalactiae, S. uberis, S. parauberis*, and *S. iniae* are detailed in Examples 1, 2 and 3, infra.

After isolating and cloning the desired GapC protein sequences, polynucleotide sequences encoding the chimeric proteins are constructed using standard recombinant techniques including PCR amplification, restriction endonuclease digestion and ligation. See, e.g., Sambrook et al., supra. Methods for constructing Gap4, an especially preferred embodiment of the present invention, are detailed in Example 4, infra.

Alternatively, the DNA sequences encoding the proteins of interest can be prepared synthetically rather than cloned. The DNA sequences can be designed with the appropriate codons for the particular amino acid sequence. In general, one will select preferred codons for the intended host if the sequence will be used for expression. The complete sequence is assembled from overlapping oligonucleotides prepared by standard methods and assembled into a complete coding sequence. See, e.g., Edge (1981) *Nature* 292: 756; Nambair et al. (1984) *Science* 223:1299; Jay et al. (1984) *J. Biol. Chem.* 259:6311.

Once coding sequences for the desired proteins have been prepared, they can be cloned into any suitable vector or replicon. Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (*Bacillus*), pIJ61 (*Streptomyces*), pUC6 (*Streptomyces*), YIp5 (*Saccharomyces*), YCp19 (*Saccharomyces*) and bovine papilloma virus (mammalian cells). See, Sambrook et al., supra; *DNA Cloning*, supra; B. Perbal, supra.

The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence may or may not contain a signal peptide or leader sequence. If a signal sequence is included, it can either be the native, homologous sequence, or a heterologous sequence. For example, the LipoF signal sequence is added to the amino-terminal region of the chimeric protein Gap4 to permit secretion of the protein after expression. See Examples 4E and 5, infra. Leader sequences can be removed by the host in post-translational processing. See, e.g., U.S. Pat. Nos. 4,431,739; 4,425,437; 4,338,397.

Other regulatory sequences which allow for regulation of expression of the protein sequences relative to the growth of the host cell may also be desirable. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases it may be necessary to modify the coding sequence so that it may be attached to the control sequences with the appropriate orientation; i.e., to maintain the proper reading frame. It may also be desirable to produce mutants or analogs of the GapC plasmin-binding protein. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are described in, e.g., Sambrook et al., supra; *DNA Cloning*, supra; *Nucleic Acid Hybridization*, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Madin-Darby bovine kidney ("MDBK") cells, as well as others. Similarly, bacterial hosts such as *E. coli, Bacillus subtilis*, and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromycesfragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodopterafrugiperda*, and *Trichoplusia ni*.

Depending on the expression system and host selected, the proteins of the present invention are produced by culturing host cells transformed by an expression vector described above under conditions whereby the protein of interest is expressed. The protein is then isolated from the host cells and purified. If the expression system secretes the protein into the growth media, the protein can be purified directly from the media. If the protein is not secreted, it is isolated from cell lysates. The selection of the appropriate growth conditions and recovery methods are within the skill of the art.

The proteins of the present invention may also be produced by chemical synthesis such as solid phase peptide synthesis, using known amino acid sequences or amino acid sequences derived from the DNA sequence of the genes of interest. Such methods are known to those skilled in the art. See, e.g., J. M. Stewart and J. D. Young, *Solid Phase Peptide Synthesis*, 2nd Ed., Pierce Chemical Co., Rockford, Ill. (1984) and G. Barany and R. B. Merrifield, *The Peptides: Analysis, Synthesis, Biology*, editors E. Gross and J. Meienhofer, Vol. 2, Academic Press, New York, (1980), pp. 3-254, for solid phase peptide synthesis techniques; and M. Bodansky, *Principles of peptide Synthesis*, Springer-Verlag, Berlin (1984) and E. Gross and J. Meienhofer, Eds., *The Peptides: Analysis, Synthesis, Biology*, supra, Vol. 1, for classical solution synthesis. Chemical synthesis of peptides may be preferable if a small fragment of the antigen in question is capable of raising an immunological response in the subject of interest.

The chimeric GapC plasmin-binding proteins of the present invention, or their fragments, can be used to produce antibodies, both polyclonal and monoclonal. If polyclonal antibodies are desired, a selected mammal, (e.g., mouse, rabbit, goat, horse, etc.) is immunized with an antigen of the present invention, or its fragment, or a mutated antigen. Serum from the immunized animal is collected and treated according to known procedures. See, e.g., Jurgens et al. (1985) *J. Chrom.* 348:363-370. If serum containing polyclonal antibodies is used, the polyclonal antibodies can be purified by immunoaffinity chromatography, using known procedures.

Monoclonal antibodies to the chimeric GapC plasmin-binding proteins and to the fragments thereof, can also be readily produced by one skilled in the art. The general methodology for making monoclonal antibodies by using hybridoma technology is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al., *Hybridoma Techniques* (1980); Hammerling et al., *Monoclonal Antibodies and T-cell Hybridomas* (1981); Kennett et al., *Monoclonal Antibodies* (1980); see also U.S. Pat. Nos. 4,341,761; 4,399,121; 4,427,783; 4,444,887; 4,452,570; 4,466,917; 4,472,500, 4,491,632; and 4,493,890. Panels of monoclonal antibodies produced against the chimeric GapC plasmin-binding proteins, or fragments thereof, can be screened for various properties; i.e., for isotype, epitope, affinity, etc. Monoclonal antibodies are useful in purification, using immunoaffinity techniques, of the individual antigens which they are directed against. Both polyclonal and monoclonal antibodies can also be used for passive immunization or can be combined with subunit vaccine preparations to enhance the immune response. Polyclonal and monoclonal antibodies are also useful for diagnostic purposes.

Vaccine Formulations and Administration

The GapC multiple epitope fusion proteins of the present invention can be formulated into vaccine compositions, either alone or in combination with other antigens, for use in immunizing subjects as described below. Methods of preparing such formulations are described in, e.g., *Remington's Pharmaceutical Sciences*, Mack Publishing Company, Easton, Pa., 18 Edition, 1990. Typically, the vaccines of the present invention are prepared as injectables, either as liquid solutions or suspensions. Solid forms suitable for solution in or suspension in liquid vehicles prior to injection may also be prepared. The preparation may also be emulsified or the active ingredient encapsulated in liposome vehicles. The active immunogenic ingredient is generally mixed with a compatible pharmaceutical vehicle, such as, for example, water, saline, dextrose, glycerol, ethanol, or the like, and combinations thereof. In addition, if desired, the vehicle may contain minor amounts of auxiliary substances such as wetting or emulsifying agents and pH buffering agents.

Adjuvants which enhance the effectiveness of the vaccine may also be added to the formulation. Adjuvants may include for example, muramyl dipeptides, avridine, aluminum hydroxide, dimethyldioctadecyl ammonium bromide (DDA), oils, oil-in-water emulsions, saponins, cytokines, and other substances known in the art.

The chimeric GapC plasmin-binding protein may be linked to a carrier in order to increase the immunogenicity thereof. Suitable carriers include large, slowly metabolized macromolecules such as proteins, including serum albumins, keyhole limpet hemocyanin, immunoglobulin molecules, thyroglobulin, ovalbumin, and other proteins well known to those skilled in the art; polysaccharides, such as sepharose, agarose, cellulose, cellulose beads and the like; polymeric amino acids such as polyglutamic acid, polylysine, and the like; amino acid copolymers; and inactive virus particles.

The chimeric GapC plasmin-binding proteins may be used in their native form or their functional group content may be modified by, for example, succinylation of lysine residues or reaction with Cys-thiolactone. A sulfhydryl group may also be incorporated into the carrier (or antigen) by, for example, reaction of amino functions with 2-iminothiolane or the N-hydroxysuccinimide ester of 3-(4-dithiopyridyl propionate. Suitable carriers may also be modified to incorporate spacer arms (such as hexamethylene diamine or other bifunctional molecules of similar size) for attachment of peptides.

Other suitable carriers for the chimeric GapC plasmin-binding proteins of the present invention include VP6 polypeptides of rotaviruses, or functional fragments thereof, as disclosed in U.S. Pat. No. 5,071,651, incorporated herein by reference. Also useful is a fusion product of a viral protein and the subject chimeric proteins made by methods disclosed in U.S. Pat. No. 4,722,840. Still other suitable carriers include cells, such as lymphocytes, since presentation in this form mimics the natural mode of presentation in the subject, which gives rise to the immunized state. Alternatively, the proteins of the present invention may be coupled to erythrocytes, preferably the subject's own erythrocytes. Methods of coupling peptides to proteins or cells are known to those of skill in the art.

Furthermore, the chimeric GapC plasmin-binding proteins (or complexes thereof) may be formulated into vaccine compositions in either neutral or salt forms. Pharmaceutically acceptable salts include the acid addition salts (formed with the free amino groups of the active polypeptides) and which are formed with inorganic acids such as, for example, hydrochloric or phosphoric acids, or such organic acids as acetic, oxalic, tartaric, mandelic, and the like. Salts formed from free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Vaccine formulations will contain a "therapeutically effective amount" of the active ingredient, that is, an amount capable of eliciting an immune response in a subject to which the composition is administered. In the treatment and prevention of mastitis, for example, a "therapeutically effective amount" would preferably be an amount that enhances resistance of the mammary gland to new infection and/or reduces the clinical severity of the disease. Such protection will be demonstrated by either a reduction or lack of symptoms normally displayed by an infected host, a quicker recovery time and/or a lowered somatic cell count in milk from the infected quarter. For example, the ability of the composition to retain or bring the somatic cell count (SCC) in milk below about 500,000 cells per ml, the threshold value set by the International Dairy Federation, above which, animals are considered to have clinical mastitis, will be indicative of a therapeutic effect.

The exact amount is readily determined by one skilled in the art using standard tests. The chimeric GapC plasmin-binding protein concentration will typically range from about 1% to about 95% (w/w) of the composition, or even higher or lower if appropriate. With the present vaccine formulations, 5 to 500 µg of active ingredient per ml of injected solution should be adequate to raise an immunological response when a dose of 1 to 3 ml per animal is administered.

To immunize a subject, the vaccine is generally administered parenterally, usually by intramuscular injection. Other modes of administration, however, such as sub-cutaneous, intraperitoneal and intravenous injection, are also acceptable. The quantity to be administered depends on the animal to be treated, the capacity of the animal's immune system to synthesize antibodies, and the degree of protection desired. Effective dosages can be readily established by one of ordinary skill in the art through routine trials establishing dose response curves. The subject is immunized by administration of the vaccine in at least one dose, and preferably two doses. Moreover, the animal may be administered as many doses as is required to maintain a state of immunity to infection.

Additional vaccine formulations which are suitable for other modes of administration include suppositories and, in some cases, aerosol, intranasal, oral formulations, and sustained release formulations. For suppositories, the vehicle composition will include traditional binders and carriers, such as, polyalkaline glycols, or triglycerides. Such suppositories may be formed from mixtures containing the active ingredient in the range of about 0.5% to about 10% (w/w), preferably about 1% to about 2%. Oral vehicles include such normally employed excipients as, for example, pharmaceutical grades of mannitol, lactose, starch, magnesium, stearate, sodium saccharin cellulose, magnesium carbonate, and the like. These oral vaccine compositions may be taken in the form of solutions, suspensions, tablets, pills, capsules, sustained release formulations, or powders, and contain from about 10% to about 95% of the active ingredient, preferably about 25% to about 70%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Controlled or sustained release formulations are made by incorporating the protein into carriers or vehicles such as liposomes, nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures. The chimeric GapC plasmin-binding proteins can also be delivered using implanted mini-pumps, well known in the art.

The chimeric GapC plasmin-binding proteins of the instant invention can also be administered via a carrier virus which expresses the same. Carrier viruses which will find use with the instant invention include but are not limited to the vaccinia and other pox viruses, adenovirus, and herpes virus. By way of example, vaccinia virus recombinants expressing the novel proteins can be constructed as follows. The DNA encoding the particular protein is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the instant protein into the viral genome. The resulting TK recombinant can be selected by culturing the cells in the presence of 5-bromodeoxyuridine and picking viral plaques resistant thereto.

An alternative route of administration involves gene therapy or nucleic acid immunization. Thus, nucleotide sequences (and accompanying regulatory elements) encoding the subject chimeric GapC plasmin-binding proteins can be administered directly to a subject for in vivo translation thereof. Alternatively, gene transfer can be accomplished by transfecting the subject's cells or tissues ex vivo and reintroducing the transformed material into the host. DNA can be directly introduced into the host organism, i.e., by injection (see International Publication No. WO/90/11092; and Wolff et al. (1990) *Science* 247:1465-1468). Liposome-mediated gene transfer can also be accomplished using known methods. See, e.g., Hazinski et al. (1991) *Am. J. Respir. Cell Mol. Biol.* 4:206-209; Brigham et al. (1989) *Am. J. Med. Sci.* 298:278-281; Canonico et al. (1991) *Clin. Res.* 39:219A; and Nabel et al. (1990) *Science* 249:1285-1288. Targeting agents, such as antibodies directed against surface antigens expressed on specific cell types, can be covalently conjugated to the liposomal surface so that the nucleic acid can be delivered to specific tissues and cells susceptible to infection.

Diagnostic Assays

As explained above, the chimeric GapC plasmin-binding proteins of the present invention may also be used as diagnostics to detect the presence of reactive antibodies of streptococcus, for example *S. dysgalactiae*, in a biological sample in order to determine the presence of *streptococcus* infection. For example, the presence of antibodies reactive with chimeric GapC plasmin-binding proteins can be detected using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassays; immunoelectrophoresis; immunoprecipitation, etc. The reactions generally include revealing labels such as fluorescent, chemiluminescent, radioactive, enzymatic labels or dye molecules, or other methods for detecting the formation of a complex between the antigen and the antibody or antibodies reacted therewith.

The aforementioned assays generally involve separation of unbound antibody in a liquid phase from a solid phase support to which antigen-antibody complexes are bound. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

Typically, a solid support is first reacted with a solid phase component (e.g., one or more chimeric GapC plasmin-binding proteins) under suitable binding conditions such that the component is sufficiently immobilized to the support. Sometimes, immobilization of the antigen to the support can be enhanced by first coupling the antigen to a protein with better binding properties. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other molecules that can be used to bind the antigens to the support include polysaccharides, polylactic acids, polyglycolic acids, polymeric amino acids, amino acid copolymers, and the like. Such molecules and methods of coupling these molecules to the antigens, are well known to those of ordinary skill in the art. See, e.g., Brinkley, M. A. *Bioconjugate Chem.* (1992) 3:2 et al., *J. Appl. Biochem.* (1984) 6:56-63; and Anjaneyulu and Staros, *International J. of peptide and Protein Res.* (1987) 30:117-124.

After reacting the solid support with the solid phase component, any non-immobilized solid-phase components are removed from the support by washing, and the support-bound component is then contacted with a biological sample suspected of containing ligand moieties (e.g., antibodies toward the immobilized antigens) under suitable binding conditions. After washing to remove any non-bound ligand, a secondary binder moiety is added under suitable binding conditions, wherein the secondary binder is capable of associating selectively with the bound ligand. The presence of the secondary binder can then be detected using techniques well known in the art.

More particularly, an ELISA method can be used, wherein the wells of a microtiter plate are coated with a chimeric GapC plasmin-binding protein. A biological sample containing or suspected of containing anti-chimeric GapC plasmin-binding protein immunoglobulin molecules is then added to the coated wells. After a period of incubation sufficient to allow antibody binding to the immobilized antigen, the plate(s) can be washed to remove unbound moieties and a detectably labeled secondary binding molecule added. The secondary binding molecule is allowed to react with any captured sample antibodies, the plate washed and the presence of the secondary binding molecule detected using methods well known in the art.

Thus, in one particular embodiment, the presence of bound anti-chimeric GapC plasmin-binding antigen ligands from a biological sample can be readily detected using a secondary binder comprising an antibody directed against the antibody ligands. A number of anti-bovine immunoglobulin (Ig) molecules are known in the art which can be readily conjugated to a detectable enzyme label, such as horseradish peroxidase, alkaline phosphatase or urease, using methods known to those of skill in the art. An appropriate enzyme substrate is then used to generate a detectable signal. In other related embodiments, competitive-type ELISA techniques can be practiced using methods known to those skilled in the art.

Assays can also be conducted in solution, such that the chimeric GapC plasmin-binding proteins and antibodies specific for those proteins form complexes under precipitating conditions. In one particular embodiment, chimeric GapC plasmin-binding proteins can be attached to a solid phase particle (e.g., an agarose bead or the like) using coupling techniques known in the art, such as by direct chemical or indirect coupling. The antigen-coated particle is then contacted under suitable binding conditions with a biological sample suspected of containing antibodies for the chimeric GapC plasmin-binding proteins. Cross-linking between bound antibodies causes the formation of particle-antigen-antibody complex aggregates which can be precipitated and separated from the sample using washing and/or centrifugation. The reaction mixture can be analyzed to determine the presence or absence of antibody-antigen complexes using any of a number of standard methods, such as those immunodiagnostic methods described above.

In yet a further embodiment, an immunoaffinity matrix can be provided, wherein a polyclonal population of antibodies from a biological sample suspected of containing anti-chimeric GapC plasmin-binding molecules is immobilized to a substrate. In this regard, an initial affinity purification of the sample can be carried out using immobilized antigens. The resultant sample preparation will thus only contain anti-*streptococcus* moieties, avoiding potential non-specific binding properties in the affinity support. A number of methods of immobilizing immunoglobulins (either intact or in specific fragments) at high yield and good retention of antigen binding activity are known in the art. Not being limited by any particular method, immobilized protein A or protein G can be used to immobilize immunoglobulins.

Accordingly, once the immunoglobulin molecules have been immobilized to provide an immunoaffinity matrix, labeled chimeric GapC plasmin-binding proteins are contacted with the bound antibodies under suitable binding conditions. After any non-specifically bound antigen has been washed from the immunoaffinity support, the presence of bound antigen can be determined by assaying for label using methods known in the art.

Additionally, antibodies raised to the chimeric GapC plasmin-binding proteins, rather than the chimeric GapC plasmin-binding proteins themselves, can be used in the above-described assays in order to detect the presence of antibodies to the proteins in a given sample. These assays are performed essentially as described above and are well known to those of skill in the art.

The above-described assay reagents, including the chimeric GapC plasmin-binding proteins, or antibodies thereto, can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

Deposits of Strains Useful in Practicing the Invention

A deposit of biologically pure cultures of the following strains was made with the American Type Culture Collection, 10801 University Boulevard, Manassas, Va., under the provisions of the Budapest Treaty. The accession number indicated was assigned after successful viability testing, and the requisite fees were paid. The designated deposits will be maintained for a period of thirty (30) years from the date of deposit, or for five (5) years after the last request for the deposit, whichever is longer. Should a culture become nonviable or be inadvertently destroyed, or, in the case of plasmid-containing strains, lose its plasmid, it will be replaced with a viable culture(s) of the same taxonomic description.

Should there be a discrepancy between the sequence presented in the present application and the sequence of the gene of interest in the deposited plasmid due to routine sequencing errors, the sequence in the deposited plasmid controls.

| Bacterial Strain | Plasmid | Deposit Date | ATCC No. |
| --- | --- | --- | --- |
| XLI Blue MRF | pPolyGap.1 | May 31, 2000 | PTA-1981 |
| XLI Blue MRF | pPolyGap.2 | May 31, 2000 | PTA-1974 |
| XLI Blue MRF | pPolyGap.3 | May 31, 2000 | PTA-1979 |
| XLI Blue MRF | pPolyGap.4 | May 31, 2000 | PTA-1980 |
| XLI Blue MRF | polygap4 | May 31, 2000 | PTA-1978 |

Below are examples of specific embodiments for carrying out the present invention. The examples are offered for illustrative purposes only, and are not intended to limit the scope of the present invention in any way.

C. EXPERIMENTAL

EXAMPLE 1

Preparation of Chromosomal DNA

A clinical *S. dysgalactiae* isolate from a case of bovine mastitis (ATCC Accession No. ATCC43078) was obtained from the American Type Culture Collection (10801 University Boulevard, Manassas, Va. 20110-2209), and was used as a source of DNA. The organism was routinely grown on TSA sheep blood agar plates (PML Microbiologicals, Mississauga, Ontario) at 37° C. for 18 hours, or in Todd-Hewitt broth (Oxoid Ltd., Hampshire, England) supplemented with 0.3% yeast extract (THB-YE) at 37° C., 5% $CO_2$.

Chromosomal DNA was prepared from *S. dysgalactiae* grown in 100 ml of THB-YE supplemented with 20 mM glycine for approximately 6 hours, until an $A_{600}$ of 0.8 to 1.0 was reached. Cells were harvested and re-suspended in 50 mM EDTA, 50 mM Tris-HCl, 0.5% Tween-20® (Sigma, St. Louis, Mo.) and supplemented with RNase A (200 mg/ml), proteinase K (20 mg/ml), lysozyme (100 mg/ml) and mutanolysin (100 mg/ml). (all enzymes purchased from SIGMA, St. Louis, Mo.). Following bacterial lysis for 30 minutes at 37° C. with vigorous shaking, guanidine hydrochloride and Tween-2®, pH 5.5, were mixed with the lysate to give a final concentration of 0.8 M and 5%, respectively. This mixture was incubated at 50° C. for 30 minutes. The chromosomal DNA was then purified using a Qiagen genomic-tip 100 g (Qiagen, Santa Clarita, Calif.) and precipitated using 0.7 volumes of isopropanol. The resulting pellet was washed in 70% ethanol and re-suspended in 0.5 ml 10 mM Tris-HCl, pH 8.8.

Chromosomal DNA from *S. agalactiae, S. uberis* and, *S. parauberis* was isolated essentially as described above, from strains designated ATCC 27541, 9927, and 13386, respectively. Chromosomal DNA from *S. iniae* was also isolated as above from a strain designated 9117 obtained from Mount Sinai Hospital, University of Toronto, Canada.

EXAMPLE 2

Amplification and Cloning of gapC Genes from *S. dysgalactiae, S. uberis, S. parauberis, S. agalactiae* and *S. iniae*

The polynucleotide sequences encoding GapC from *S. dysgalactiae, S. uberis, S. parauberis, S. agalactiae* and *S. iniae* were initially isolated from chromosomal DNA by PCR amplification. The primers used to PCR-amplify the gapC genes from all species were gapC1 (SEQ ID NO:1) and gapC1r (SEQ ID NO:2), shown in Table 1. In the table, underlining denotes nucleotides added to the original sequences (i.e., nucleotides added to the 5' end of the original sense strand sequence and to the 3' end of the original anti-sense strand sequence, respectively, of the gapC coding region being amplified), and bolding indicates the location of restriction endonuclease recognition sites.

PCR was carried out using Vent DNA polymerase (New England Biolabs, Mississauga, ON, Canada). A reaction mixture containing 0.2 μg of genomic DNA, 1 pM of each of the preceding primers, 100 pM each of dATP, dTTP, dCTP and dGTP, 10 mM Tris HCL, pH9; 1.5mM $MgCl_2$, 50 mM HCL, 1.5 units Taq DNA polymerase (Pharmacia, Quebec, Canada) was incubated for 40 amplification cycles of 40 seconds at 94° C., 40 seconds at 55° C., and 1 minute, 20 seconds at 72° C., and then for a single cycle of 10 minutes at 72° C.

The resulting PCR reaction products were then digested with NdeI and BamHI. In the case of the *S. dysgalactiae* gapC product, the fragment was cloned directly into the same sites of pET15b (Novagen, Madison, Wis.) after the plasmid was digested with the same enzymes. The resulting construct was denominated pET15bgapC. In the case of the *S. agalactiae, S. uberis, S. parauberis* and *S. iniae* sequences, each was first cloned into pPCR-Script using the cloning protocol described in the PCR-Script Amp Cloning Kit (Stratagene, La Jolla, Calif.), subsequently excised using NdeI and BamHI, and finally re-cloned into the corresponding sites of pET15b using conventional cloning protocols (see e.g., Sambrook et al., supra).

The plasmids containing the *S. agalactiae, S. uberis, S. parauberis* and *S. iniae* sequences were designated pMF521c-inv, pMF521a-inv, pMF521d-inv, and pMF521e-inv, respectively.

TABLE 1

Sequence Identification Numbers and Corresponding Nucleotide and Amino Acid Sequences

| SEQ ID NO. | Name | Nucleotide Sequence (5' to 3') |
|---|---|---|
| 1 | gapC1 | GG CGG CGG CAT ATG GTA GTT AAA GTT GGT ATT AAC GG |
| 2 | gapC1r | GC GGA TCC TTA TTT AGC GAT TTT TGC AAA GTA CTC |
| 3 | Gap-1 | AAA AAA GGA TCC GGT ATG GTA GTT AAA GTT GG |
| 4 | Gap-2 | AAA AAA CCA TGG TTA CTC GAG TGC TTC CAG AAC GAT TTC |
| 5 | Gap-3 | AAA AAA CTC GAG GGT ACT GTA GAA GTT AAA G |

TABLE 1-continued

Sequence Identification Numbers and Corresponding
Nucleotide and Amino Acid Sequences

| SEQ ID NO. | Name | Nucleotide Sequence (5' to 3') |
|---|---|---|
| 6 | Gap-4 | AAA AAA CCA TGG TTA ATC GAT TTC AAG AAC GAT TTC AAC ACC GTC |
| 7 | Gap-5 | AAA AAA ATC GAT GGT ACT GTT GAA GTT AAA GAA G |
| 8 | Gap-6 | AAA AAA CCA TGG TTA ACT AGT TGC TTC AAG AAC GAT TTC TAC GCC |
| 9 | Gap-7 | AAA AAA ACT AGT TTC TTT GCT AAA AAA GAA GCT GC |
| 10 | Gap-8 | AAA AAA CCA TGG CTA TTA TTA TTT AGC GAT TTT TGC AAA ATA CTC |
| 11 | *Streptococcus dysgalactiae* gapC gene | (see FIG. 1) |
| 12 | *Streptococcus dysgalactiae* GapC protein | |
| 13 | *Streptococcus agalactiae* gapC gene | (see FIG. 2) |
| 14 | *Streptococcus agalactiae* GapC protein | |
| 15 | *Streptococcus uberis* gapC gene | (see FIG. 3) |
| 16 | *Streptococcus uberis* GapC protein | |
| 17 | *Streptococcus parauberis* gapC gene | (see FIG. 4) |
| 18 | *Streptococcus parauberis* GapC protein | |
| 19 | *Streptococcus iniae* gapC gene | (see FIG. 5) |
| 20 | *Streptococcus iniae* GapC protein | |
| 21 | Gap4 chimeric gapC gene | (see FIG. 6) |
| 22 | Gap4 chimeric GapC protein | |

EXAMPLE 3

Sequencing of gapC Genes

The genes isolated and cloned in the preceding examples were sequenced using fluorescence tag terminators on an ABI 373 DNA automatic sequencer (Applied Biosystems, Emeryville, Calif.) at the Plant Biotechnology Institute (PBI, Saskatoon, Saskatchewan, Canada).

The nucleotide sequences so determined, and the corresponding amino acid sequences deduced therefrom, are shown in FIGS. 1 through 5.

EXAMPLE 4

Construction of a Chimeric gapC Gene

A chimeric gapC gene composed of sequences from *S. dysgalactiae*, *S. parauberis*, and *S. agalactiae* was constructed in a three-step process using pAA556, a standard tac-inducible expression plasmid derived from the plasmid pGH432 that contains the signal sequence from the *E. Coli* ompF gene.

The partial gapC gene sequences used to construct the chimeric gene were prepared by PCR amplification of selected polynucleotide sequences from the genomic gapC genes isolated above, using the primers Gap-1 through Gap-8. The primer sequences are depicted in Table 1.

After assembly, the chimeric gene, sans the ompF signal sequence, was then excised from pAA556 and inserted into the plasmid pAA555, a pGH432 derivative that is a standard tac-inducible expression plasmid containing the signal sequence from the *E. coli* ompF gene.

A. Construction of pPolyGap.1

In the first step, the first 288 bases of the *S. dysgalactiae* gapC gene were PCR amplified using the primers Gap-1 and Gap-2.

PCR amplification was carried out as follows: 1.6 µg of template DNA was combined in a reaction mixture containing 20 pM each of primer Gap-1 (SEQ ID NO:3) and Gap-2 (SEQ ID NO:4). 200 µm each of dATP, dCTP, dGTP and dTTP, 2.5 mM MgSO$_4$, PCR Buffer (10 mM Tris-HCl, pH 8.3, 50 mM KCl), and 1 unit Taq DNA polymerase (Pharmacia, Quebec, Canada). The mix was amplified for 1 cycle of 1 minute at 95° C., then for 29 cycles of 1 minute at 95° C., 1 minute at 55° C., and 30 seconds at 72° C., and finally for 1 cycle of 10 minutes at 40° C.

The amplification product was then digested with BamHI and NcoI and inserted into the same sites of an pAA556 vector. The resulting plasmid construct, designated pPolyGap.1, is illustrated in FIG. 21.

B. Construction of pPolyGap.2

A PCR product representing bases 170-285 of the *S. parauberis* gapC gene was then obtained using the primers Gap-3 (SEQ ID NO:5) and Gap-4 (SEQ ID NO:6). This product codes for an amino acid sequence identical to the corresponding amino acid sequence found in the *S. uberis* gapC gene. PCR amplification was carried out essentially as above, except using 2 µg of template DNA.

The *S. parauberis* PCR product and the pPolyGap1plasmid were both digested with Xho1 and Nco1, and the PCR product was ligated into the corresponding sites in the vector. This construct, called pPolyGap.2, is illustrated in FIG. 22.

C. Construction of pPolyGap.3

Nucleotides 166-288 of the *S. agalactiae* gapC gene were amplified using PCR primers Gap-5 (SEQ ID NO:7) and Gap-6 (SEQ ID NO:8) as in Example 4B above.

The PCR product obtained was digested with ClaI and NcoI, then inserted into the same sites of pPolyGap2 immediately downstream of the *S. parauberis* sequence. pPolyGap3 is diagramed in FIG. 23.

D. Construction of pPolyGap.4

The final step in constructing the chimeric gene involved the insertion of the remaining *S. dysgalactiae* gapC sequence (nucleotides 295-1011) in-frame and immediately downstream of the *S. agalactiae* sequence.

The *S. dysgalactiae* sequence was first PCR amplified using the primers Gap-7 (SEQ ID NO:9) and Gap-8 (SEQ ID NO:10) as in Example 4A above. The amplification product was then digested with the enzyme GamHi/NcoI, as was the pPolyGap.3 vector, and the fragment was then ligated into the corresponding vector sites.

This final step resulted in the plasmid pPolyGap.4 containing the complete gapC chimeric gene construct comprising an *S. dysgalactiae* gapC backbone with unique sequences from *S. parauberis* as well as *S. agalactiae*. See FIG. 24.

E. Cloning of the Chimeric gapC Gene into pAA55: Construction of PolyGap.4

The chimeric gapC gene constructed in the preceding steps was excised from pAA556 by digestion with BamHl and NcoI and inserted into the plasmid pAA555 digested with the same enzymes. pAA555 is identical to pAA556 except that the former plasmid contains the LipoF signal sequence, and provides for the addition of a cysteine at the amino terminal end of the mature GapC protein. The N-terminal cysteine was added to insure the chimeric protein's efficient secretion of from the cell and binding to the membrane via the lipid-moiety. The coding sequence of the PolyGap4 plasmid construct is shown in FIGS. 6A-6C.

EXAMPLE 5

Expression and Isolation of the Chimeric GapC Protein

PolyGap4 is used to transform *E. coli* J5 in the presence of polyethlene glycol (Kurien and Scofield (1995) *BioTechniques* 18:1023-1026).

The transformed cells carrying pPolyGap4 are grown to logarithmic phase in LB media at 37° C. with shaking. Expression of the chimeric GapC protein is then induced by adding IPTG to a final concentration of 1 mM and incubating the cells at 37° C. for an additional 4 hours.

The chimeric GapC protein is then extracted from the cell surface by differential solubilization. The cells are collected by centrifugation and re-suspended in a volume of resuspension buffer (0.85% NaCl solution containing 0.6% sarkosyl) equal to ⅒th the original culture volume. The suspension is incubated at room temperature for 30 minutes with gentle shaking. The cells are collected by centrifuation and the supernatant containing the chimeric GapC protein is passed through a 0.2 µm membrane filter. Aliquots of the sterile supernatant are analyzed by SDS-PAGE and Western blots using a rabbit anti-GapC polyclonal antibody.

EXAMPLE 6

Immunization of Animals with the Chimeric GapC Protein

Vaccines were formulated in such a fashion that they contained 100 µg/ml of purified chimeric GapC protein in the oil-based adjuvant VSA3 (VIDO, Saskatoon, Saskatchewan, Canada). VSA3 is a combination of Emulsigen Plus™ (MVP Laboratories, Ralston, Nebr.) and dimethyldioctadecyl ammonium bromide (Kodak, Rochester, N.Y.).

Non-lactating Holstein cows with no history of *S. dysgalactiae* infection are obtained. Two weeks prior to vaccination, all animals are treated with 300 mg of Cephapirin per quarter (Cepha-dry™, Ayerst Laboratories, Montreal, Canada), in order to resolve any pre-existing udder infection prior to the vaccination step.

Groups of experimental animals are immunized subcutaneously with two doses of vaccines containing the chimeric GapC protein or a placebo with a three-week interval between immunizations. Ten days to two weeks following the second immunization, animals are exposed to 500-1,000 colony forming units of *S. dysgalactiae* delivered into three quarters with an udder infusion cannula. The fourth quarter on each animal serves as an un-infective control.

All animals are examined daily for clinical signs of disease and samples from all udder quarters are collected on each day. Samples are observed for consistency and antibody titre, somatic cell counts, and bacterial numbers are determined.

EXAMPLE 7

Determination of Antibodies Specific for the Chimeric GapC Protein

GapC-specific antibodies in bovine serum are measured using an enzyrne-linked immunosorbent assay (ELISA). Briefly, microtitre plates (NUNC, Naperville, Ill.) are coated by adding 0.1 microgram per well purified chimeric protein in 50 mM sodium carbonate buffer, pH 9.6, incubated overnight at 4° C. The liquid is removed and the wells are blocked with 3% bovine serum albumin for 1 hr at 37° C. Serial dilutions of bovine serum (from 1:4 to 1:64,000) are added to the wells and incubated for 2 hours at room temperature. The wells are aspirated, washed and incubated with 100 µl of alkaline phosphatase-conjugated goat anti-bovine IgG (Kirkgaard & Perry Laboratories Inc., Gaithersburg, Md.) for 1 hr at room temperature. The wells are washed again, and 100 µl of p-nitrophenol phosphate (Sigma, St. Louis, Mo.) is added as a substrate to detect alkaline phosphatase activity. The absorbance at 405 nanometers is recorded, following 1 hr incubation with the substrate at room temperature.

EXAMPLE 8

Bacterial Colonization

Bacteria are enumerated by spreading serial dilutions ($10^0$ to $10^{-6}$) directly onto TSA sheep blood agar plates followed by overnight incubation at 37° C., 5% $CO_2$. Colonization is defined as >500 cfu/ml of the challenge organism recovered.

To confirm that the bacteria recovered from milk secretions are *S. dysgalactiae*, selected colonies recovered from each animal are tested using an API strep-20 test (bioMerieux SA, Hazelwood, Mo.) according to the manufacturer's instructions. This test identifies *Streptococcus* species according to an analytical profile compiled on the basis of enzymatic activity and sugar fermentation, using either an analytical profile index or identification software.

The relationship between anti-GapC titer and bacterial colonization is also determined.

EXAMPLE 9

Determination of Inflammatory Response

Inflammatory response is measured as a function of mammary gland somatic cell count i.e., lymphocytes, neutrophils, and monocytes). Somatic cell counts are measured using standard techniques recommended by Agriculture and AgriFood Canada (IDF50B (1985): Milk and Milk Products—Methods of Sampling in a Coulter counter). Samples are read within 48 hours of collection and fixation, at days 1 through 7 post challenge.

The numbers of somatic cells present in the gland are determined on each day post challenge.

Although preferred embodiments of the subject invention have been described in some detail, it is understood that obvious variations can be made without departing from the spirit and the scope of the invention as defined by the appended claims.

What is claimed is:

1. A method of detecting *Streptococcus* antibodies in a biological sample, comprising:
   (a) reacting said biological sample with a multiple epitope fusion polypeptide comprising more than one *Streptococcus* GapC epitope from more than one *Streptococcus* species, under conditions which allow said *Streptococcus* antibodies, when present in the biological sample, to bind to said sequence to form an antibody/antigen complex, wherein said fusion protein comprises epitopes that correspond to:
   (i) the amino acid sequences shown at amino acid positions 62 to 81, inclusive, of SEQ ID NOS: 12, 14, 16, 18 and 20;
   (ii) the amino acid sequences shown at about amino acid positions 102 to 112, inclusive, of SEQ ID NOS: 12, 14, 16, 18 and 20;
   (iii) the amino acid sequences shown at about amino acid positions 165 to 172, inclusive, of SEQ ID NOS: 12, 14, 16, 18 and 20;
   (iv) the amino acid sequences shown at about amino acid positions 248 to 271, inclusive, of SEQ ID NOS: 12, 14, 16, 18 and 20; and
   (v) the amino acid sequences shown at about amino acid positions 286 to 305, inclusive, of SEQ ID NOS: 12, 14, 16, 18 and 20; and
   (b) detecting the presence or absence of said complex, and thereby detecting the presence or absence of *Streptococcus* antibodies in said sample.

2. The method of claim 1, wherein said multiple epitope fusion polypeptide comprises a GapC epitope from more than one *Streptococcus* species selected from the group consisting of *Streptococcus dysgalactiae*, *Streptococcus agalactiae*, *Streptococcus uberis*, *Streptococcus parauberis*, and *Streptococcus iniae*.

3. The method of claim 2, wherein said multiple epitope fusion polypeptide comprises GapC epitopes from *Streptococcus dysgalactiae*, *Streptococcus agalactiae* and *Streptococcus parauberis*.

4. The method of claim 3, wherein the GapC epitopes in said multiple epitope fusion polypeptide are separated by a spacer amino acid sequence.

5. The method of claim 1, wherein said multiple epitope fusion polypeptide comprises an amino acid sequence having at least 80% sequence identity to the contiguous sequence of amino acids depicted at positions 28-448 of the amino acid sequence depicted in SEQ ID NO:22.

6. The method of claim 1, wherein said multiple epitope fusion polypeptide comprises an amino acid sequence having at least 90% sequence identity to the contiguous sequence of amino acids depicted at positions 28-448 of the amino acid sequence depicted in SEQ ID NO:22.

7. The method of claim 1, wherein said multiple epitope fusion polypeptide comprises an amino acid sequence having at least 95% sequence identity to the contiguous sequence of amino acids depicted at positions 28-448 of the amino acid sequence depicted in SEQ ID NO:22.

8. The method of claim 1, wherein said multiple epitope fusion polypeptide comprises the amino acid sequence of SEQ ID NO:22.

9. The method of claim 5, wherein said multiple epitope fusion polypeptide further comprises a signal sequence.

10. The method of claim 8, wherein said multiple epitope fusion polypeptide further comprises a signal sequence.

11. The method of claim 9, wherein said signal sequence comprises the amino acid sequence depicted at positions 1-27 of SEQ ID NO:22.

12. The method of claim 10, wherein said signal sequence comprises the amino acid sequence depicted at positions 1-27 of SEQ ID NO:22.

* * * * *